United States Patent
Wu et al.

(10) Patent No.: US 12,370,242 B2
(45) Date of Patent: Jul. 29, 2025

(54) FORMULATIONS OF PEGYLATED ARGININE DEIMINASE

(71) Applicant: Polaris Group, Grand Cayman (KY)

(72) Inventors: Bor-Wen Wu, San Diego, CA (US); James Thomson, San Diego, CA (US); Wen-Chin Tsai, La Jolla, CA (US)

(73) Assignee: POLARIS GROUP, Grand Cayman (KY)

( * ) Notice: Subject to any disclaimer, the term of this patent is extended or adjusted under 35 U.S.C. 154(b) by 0 days.

(21) Appl. No.: 15/802,166

(22) Filed: Nov. 2, 2017

(65) Prior Publication Data

US 2018/0296652 A1    Oct. 18, 2018

Related U.S. Application Data

(60) Provisional application No. 62/416,607, filed on Nov. 2, 2016.

(51) Int. Cl.
| | | |
|---|---|---|
| *A61K 38/50* | (2006.01) | |
| *A61K 9/00* | (2006.01) | |
| *A61K 47/60* | (2017.01) | |
| *C12N 9/78* | (2006.01) | |
| *C12N 9/96* | (2006.01) | |

(52) U.S. Cl.
CPC ............ *A61K 38/50* (2013.01); *A61K 9/0019* (2013.01); *A61K 47/60* (2017.08); *C12N 9/78* (2013.01); *C12N 9/96* (2013.01); *C12Y 305/03006* (2013.01)

(58) Field of Classification Search
CPC ........... A61K 38/50; A61K 45/06; C12N 9/78
See application file for complete search history.

(56) References Cited

U.S. PATENT DOCUMENTS

| | | | |
|---|---|---|---|
| 5,372,942 A | 12/1994 | Mcgarrity et al. | |
| 5,474,928 A | 12/1995 | Takaku et al. | |
| 5,804,183 A | 9/1998 | Filpula et al. | |
| 6,132,713 A | 10/2000 | Fiipula et al. | |
| 6,180,387 B1 | 1/2001 | Biswas et al. | |
| 6,183,738 B1 | 2/2001 | Clark | |
| 6,635,462 B1 | 10/2003 | Ensor et al. | |
| 7,204,980 B2 | 4/2007 | Clark | |
| 7,323,167 B2 | 1/2008 | Clark et al. | |
| 7,413,735 B2 | 8/2008 | Min et al. | |
| 9,333,268 B2 | 5/2016 | Bomalaski et al. | |
| 9,731,028 B2 | 8/2017 | Bomalaski et al. | |
| 9,789,170 B2 | 10/2017 | Showalter et al. | |
| 10,463,721 B2 | 11/2019 | Wu et al. | |
| 2003/0215429 A1 | 11/2003 | de Simone | |
| 2004/0096437 A1 | 5/2004 | Min et al. | |
| 2004/0258675 A1 | 12/2004 | Ensor et al. | |
| 2005/0129706 A1 | 6/2005 | Clark | |
| 2006/0002915 A1 | 1/2006 | Min et al. | |
| 2007/0198198 A1 | 8/2007 | Burczynski et al. | |
| 2007/0212311 A1 | 9/2007 | Burne et al. | |
| 2009/0238813 A1 | 9/2009 | Georgiou et al. | |
| 2010/0197944 A1 | 8/2010 | Palle et al. | |
| 2010/0303893 A1 | 12/2010 | Luo et al. | |
| 2011/0111403 A1 | 5/2011 | Petrauskene et al. | |
| 2011/0301189 A1 | 12/2011 | Khattar et al. | |
| 2012/0015049 A1 | 1/2012 | Zhang | |
| 2012/0148559 A1 | 6/2012 | Georgiou et al. | |
| 2013/0022625 A1 | 1/2013 | Igawa et al. | |
| 2013/0052179 A1 | 2/2013 | Huang et al. | |
| 2014/0348814 A1 | 11/2014 | Almassy et al. | |
| 2015/0071920 A1 * | 3/2015 | Larson | A61K 47/24 424/133.1 |
| 2015/0132278 A1 | 5/2015 | Bomalaski et al. | |
| 2015/0231272 A1 | 8/2015 | Bomalaski et al. | |
| 2016/0074487 A1 | 3/2016 | Showalter et al. | |
| 2017/0000862 A1 * | 1/2017 | Wu | C12Y 305/03006 |
| 2018/0010114 A1 | 1/2018 | Brin et al. | |
| 2018/0154008 A1 | 6/2018 | Bomalaski et al. | |

FOREIGN PATENT DOCUMENTS

| | | |
|---|---|---|
| CN | 105339003 A | 2/2016 |
| EP | 1987838 B1 | 1/2016 |
| JP | 2001-524836 | 12/2001 |
| JP | 2006-515281 | 5/2006 |
| JP | 2009-523433 | 6/2006 |
| KR | 10-2004-0004449 | 1/2004 |
| WO | WO 1998/051784 A1 | 11/1998 |
| WO | WO 2001/083774 A2 | 11/2001 |
| WO | WO 2002/044360 A2 | 6/2002 |
| WO | 03009817 A2 | 2/2003 |
| WO | WO 2004/046309 A2 | 6/2004 |
| WO | 2006015512 A1 | 2/2006 |
| WO | WO 2006/023665 A2 | 3/2006 |
| WO | WO 2007/108505 A1 | 9/2007 |
| WO | WO 2008/121615 A2 | 10/2008 |
| WO | WO 2011/090088 A1 | 7/2011 |
| WO | WO 2013/151568 A1 | 10/2013 |
| WO | WO 2014/151982 A2 | 9/2014 |
| WO | WO-2014184352 A1 * | 11/2014 ............... A61K 9/19 |
| WO | 2015143006 A1 | 9/2015 |
| WO | WO 2016/044376 A1 | 3/2016 |
| WO | WO 2018/085551 A2 | 5/2018 |

OTHER PUBLICATIONS

Nireesha et al, "Lyophilization/Freeze Drying—An Review", International Journal of Novel Trends in Pharmaceutical Sciences, vol. 3 No. 4, Oct. 2013 (Year: 2013).*

Al-Hussein et al., "Investigation of histidine stabilizing effects on LDH during freeze-drying", J of Pharmaceutical Sciences, vol. 102, Issue 3, p. 813-826, Mar. 2013 (Year: 2013).*

(Continued)

*Primary Examiner* — Ruth A Davis
(74) *Attorney, Agent, or Firm* — George Likourezos; Carter, DeLuca & Farrell LLP

(57) ABSTRACT

Provided are lyophilized formulations comprising pegylated arginine deiminase (ADI-PEG) and related reconstituted liquid compositions and methods of using the compositions for arginine depletion therapies, including for the treatment of various cancers.

20 Claims, 6 Drawing Sheets
Specification includes a Sequence Listing.

(56) References Cited

OTHER PUBLICATIONS

Graziano, "How does sucrose stabilize the native state of globular proteins?", International Journal of Biological Macromolecules 50 (2012) 230-235 (Year: 2012).*

Wang et al., "Impact of Sucrose level on Storage Stability of Proteins in Freeze-Dried Solids: I. Correlation of Protein-Sugar Interaction With Native Structure Preservation", Journal of Pharmaceutical Sciences, vol. 98, No. 9, Sep. 2009; DOI 10.1002/jps. 21621 (Year: 2008).*

Nandhakumar et al., Lyophillization formulation development with novel excipients for Pegylated therapeutic proteins: A case study, Journal of Pharmacy Research 2011,4(12),4754-4759 (Year: 2011).*

Office Action for U.S. Appl. No. 14/214,040, mailed Aug. 18, 2017, 25 pages.

Office Action for U.S. Appl. No. 14/214,040, mailed Mar. 30, 2018, 15 pages.

Office Action for U.S. Appl. No. 14/214,040, mailed Nov. 1, 2018, 28 pages.

Inada, et al., "Modification of Proteins with Polyethylene Glycol Derivatives." Methods In Enzymology (1994); 242: 65-90, 26 pages.

Rashotte, et al., "Daily Cycles in Body Temperature, Metabolic Rate, and Substrate Utilization in Pigeons: Influence of Amount and Timing of Food Consumption." Physiology & Behavior (1995); 57 (4): 731-746.

Schummer, et al., "The Proton Gradient Across Mycoplasma Membranes." Current Microbiology (1981); 5: 371-374.

Scopes and Smith, "Analysis of Proteins". In: Current Protocols in Molecular Biology (2006); John Wiley & Sons, Inc., Ch. 10, 10.0.1-10.0.22, Supplement 76, 22 pages.

[Author Unknown] UniProtKB/TrEMBL Submission A7LHN6_9MOLU (Sep. 11, 2007), retrieved from the Internet Jun. 12, 2018, 1 page, http://uniprot.org/uniprot/A7LHN6.txt?version=1.

[Author Unknown] UniProtKB/TrEMBL Submission A5YRS4_9MOLU (Jul. 10, 2007), retrieved from the Internet Jun. 12, 2018, 1 page, http://uniprot.org/uniprot/A5YRS4.txt?version=1.

[Author Unknown] UniProtKB/TrEMBL Submission D4XVN8_9MOLU (Jun. 15, 2010), retrieved from the Internet Jun. 12, 2018, 1 page, http://uniprot.org/uniprot/ D4XVN8.txt?version=1.

[Author Unknown] UniProtKB/TrEMBL Submission F9UJU2_9MOLU (Oct. 19, 2011), retrieved from the Internet Jun. 12, 2018, 1 page, http://uniprot.org/uniprot/ F9UJU2.txt?version=1.

Zalipsky and Lee, Polyethylene Glycol Chemistry: Biotechnical and Biomedical Applications, J. M. Harris, ed., Plenum Press, NY, Chapter 21, pp. 347-370 (1992).

Invitation to Pay Additional Fees for International Application No. PCT/US2014/026766, mailed Jul. 21, 2014, 3 pages.

Extended European Search Report for European Application No. 15842576.9, dated Jun. 18, 2018, 8 pages.

[Author Unknown] GenBank: EGV00288.1, "arginine deiminase [Mycoplasma columbinum SF7]" Aug. 8, 2011, 2 pages, downloaded May 2, 2019 at https://www.ncbi.nlm.nih.gov/protein/343128488.

International Search Report and Written Opinion for International Application No. PCT/US2017/059732, mailed May 4, 2018, 9 pages.

"IND 119967 for ADI-PEG 20." Food and Drug Administration, Division of Oncology Products 1, Reference ID: 3404331, Nov. 8, 2013, 3 pages.

"IND 120345 for ADI-PEG 20, Arginine Deiminase (recombinant, E.coli, Phoenix), PEG-20 Conjugate." Food and Drug Administration, Department of Health and Human Services, Reference ID: 3410107, Date of Submission: Nov. 7, 2013 [Date of Receipt: Nov. 8, 2013], 7 pages.

"PEGARGIMINASE. Statement on a Nonproprietary Name Adopted by the USAN Council." Polaris Pharmaceuticals, Inc., Nov. 27, 2013, CAS Registraty No. 1394129-74-8, 2 pages.

Supplementary European Search Report for European Application No. 12873622.0, mailed Oct. 12, 2015, 11 pages.

Extended European Search Report for European Application No. 14769340.2, mailed Jun. 16, 2016, 9 pages.

International Search Report and Written Opinion for International Application No. PCT/US2012/039979, mailed Nov. 5, 2012, 12 pages.

International Preliminary Report on Patentability for International Application No. PCT/US2012/039979, dated Oct. 7, 2014, 8 pages.

International Search Report and Written Opinion for International Application No. PCT/US2015/021189, mailed Jun. 25, 2015, 9 pages.

International Preliminary Report on Patentability for International Application No. PCT/US2015/021189, mailed Sep. 20, 2016, 6 pages.

International Search Report and Written Opinion for International Application No. PCT/US2014/026766, mailed Oct. 24, 2014, 14 pages.

International Preliminary Report on Patentability for International Application No. PCT/US2014/026766, mailed Sep. 15, 2015, 9 pages.

International Search Report and Written Opinion for International Application No. PCT/US2015/050354, mailed Dec. 18, 2015, 7 pages.

International Preliminary Report on Patentability for International Application No. PCT/US2015/050354, mailed Mar. 21, 2017, 6 pages.

Ascierto, P. A. et al., "Pegylated Arginine Deiminase Treatment of Patients with Metastitic Melanoma: Results from Phase I and II Studies," Journal of Clinical Oncology, 23(30):7660-7668 and Erratum p. 4047 (2005).

Avramis, V. I. et al., "Pharmacokinetic/Pharmacodynamic Relationships of Asparaginase Formulations," Clin Pharmacokinet, 44(4):367-393 (2005).

Baxalta US Inc., Westlake Village, CA, Oncaspar, U.S. Food and Drug Administration Product Label, 8 pages, (Revised 2015).

Bi, D. et al., Isolation and identification of mycoplasmas from pigeons, Chinese Journal of Animal Poultry and Infectious Diseases, 19(6):1-5 (1997) [and English translation].

Bowles, T. et al., "Pancreatic Cancer Cell Lines Deficient in Argininosuccinate Synthetase are Sensitive to Arginine Deprivation by Arginine Deiminase," Int. J. Cancer, 128(8):1950-1955 (2008).

Cantor et al., "Therapeutic enzyme deimmunization by combinatorial T-cell epitope removal using neutral drift." Proc Natl Acad Sci USA, Jan. 5, 2011, vol. 108, No. 4, pp. 1272-1277.

CAS Registry search "Pegargiminase", performed Aug. 10, 2017, 3 pages.

Chen, N. et al., "Autophagy and tumorigenesis," FEBS Letters 584:1427-1435 (2010).

Das et al., "Crystal structures of arginine deiminase with covalent reaction intermediates implications for catalytic mechanism." Structure, Apr. 2004, vol. 12, No. 4, pp. 657-667.

Daylami, R. et al., "Abstract 4847: Arginine Deprivation by PEG-ADI Induces Autophagic Cell Death and Enhances the Tumor Suppression Effect of Gemcitabine in Pancreatic Cancer," Cancer Research, 70:4847 (2010).

De Angelis, M., et al., "Arginine Catabolismby Sourdough Lactic Acid Bacteria: Purification and Characterization of the Arginine Deiminase Pathway Enzymes from Lactobacillus sanfranciscensis CB 1." Applied and Environmental Microbiology, vol. 68, No. 12, Dec. 2002, pp. 6193-6201.

De Graaf, et al., "Nonnatural amino acids for site-specific protein conjugation." Bioconjug Chem. (2009); 20(7): 1281-1295.

Delage, B. et al., "Abstract 4445: Pegylated arginine deiminase induces mitochondrial apoptosis and synergizes with cisplatin in ASS1-negative malignant pleural mesothelioma," In: Proceedings of the 101st Annual Meeting of the American Association for Cancer Research, Apr. 17-21, 2010, Washington, DC, Philadelphia, PA: AACR; Cancer Research, 70(8 Suppl):Abstract nr 4445 (2010), 2 pages.

Delage, B. et al., "Arginine Deprivation and Argininosuccinate Synthetase Expression in the Treatment of Cancer," International Journal of Cancer, 126:2762-2772 (2010).

(56) References Cited

OTHER PUBLICATIONS

Doherty, et al., "Site-specific PEGylation of engineered cysteine analogues of recombinant human granulocyte-macrophage colony-stimulating factor." Bioconjug Chem. (2005);16(5): 1291-1298.
Ensor, C. M. et al., "Pegylated Arginine Deiminase (ADI-SS PEG20,000 mw) Inhibits Human Melanomas and Hepatocellular Carcinomas in Vitro and in Vivo," Cancer Research, 62(19):5443-5450 (2002).
Extended European Search Report for European Application No. 15765975.6, dated Oct. 27, 2017, 6 pages.
Fenske, J.D., and Kenny, George E. "Role of arginine deiminase in growth of Mycoplasma hominis." Journal of Bacteriology 126.1 (1976): 501-510.
Feun, et al., "Arginine deprivation in cancer therapy." Curr Opin Clin Nutr Metab Care (2015); 18(1): 78-82.
Feun, L. et al., "Pegylated arginine deiminase: a novel anticancer enzyme agent," Expert Opin. Investig. Drugs., 15(7):815-822 (2006).
Feun, L. et al., "Arginine Deprivation as a Targeted Therapy for Cancer," Current Pharmaceutical Design, 14(11):1049-1057 (2008).
Fu, C. H. et al., "PEG-asparaginase," Expert Opinion Pharmacotherapy, 8(12):1977-1984 (2007).
Gallego, Pablo, et al. "Structural characterization of the enzymes composing the arginine deiminase pathway in Mycoplasma penetrans." PloS One (2012); 7.10: e47886.
Glazer, E. et al., "Phase II Study of Pegylated Arginine Deiminase for Nonresectable and Metastatic Hepatocellular Carcinoma," Journal of Clinical Oncology, 28(13):2220-2226 (2010).
Gong, H. et al., "Arginine Deiminase Inhibits Proliferation of Human Leukemia Cells More Potently than Asparaginase by Inducing Cell Cycle Arrest and Apoptosis," Leukemia, 14:826-829 (2000).
Guo et al., "Protein tolerance to random amino acid change", PNAS USA, 101: 9205-6210 (2004).
Guo, Zisheng, et al. Mycoplasma columbinum Strain SF7 genome translation from Guo et al, Genome Announcements (2013); 1.2: e00157-13, 64 pages.
Guo, Zisheng, et al. "Genome sequence of Mycoplasma columbinum strain SF7." Genome Announcements (2013); 1.2: e00157-13.
Guven, K. et al., "Cisplatin and Carboplatin Combination as Second-Lind Chemotherapy in Dacarbazine-Resistant Melanoma Patients," Melanoma Research, 11:411-415 (2001).
He, W. et al., "Abstract 4703: Lack of Expression of Argininosuccinate Synthetase in Human Cancer Tissue: A Biomarker for Sensitivity to Arginine Depetion with Pegylated Arginine Deiminase," Cancer Research, 70, Proceedings: AACR 101st Annual Meeting 2010—Apr. 17-21, 2010, 2 pages.
Henningham et al., "Structure-informed design of an enzymatically inactive vaccine component for group A *Streptococcus*." MBio, Jul./Aug. 2013, vol. 4, No. 4, pii: e00509-13.
Hernandez, C. et al., "Pegylated Arginase I: A Potential Therapeutic Approach in T-ALL," Blood, 115(25):5214-5221 (2010).
Holtsberg, F. W. et al., "Poly(ethylene glycol) (PEG) Conjugated Arginine Deiminase: Effects of PEG Formulations on its Pharmacological Properties," Journal of Controlled Release, 80:259-271 (2002).
International Pharmaceutical Excipients Council Japan (ed.), Iyakutenkabutsu Jiten [Pharmaceutical Excipient Dictionary] 2007, Yakuji Nippo Limited, Jul. 25, 2007, p. 220-221.
Izzo, F., et al., "Pegylated arginine deiminase treatment of patients with unresectable hepatocellular carcinoma: results from phase I/II studies." J Clin Oncol. (2004); 22(10): 1815-1822.
Kelly, M. P. et al., "Arginine Deiminase PEG20 Inhibits Growth of Small Cell Lung Cancers Lacking Expression of Argininosuccinate Synthetase," British Journal of Cancer, 106(2):324-332 (2012).
Kelly, M., et al., Abstract 4519: Small Cell Lung Cancers Lack Expression of Argininosuccinate Synthase (ASS) and are sensitive to Arginine Deprivation Using Arginine Deiminase-PEG20 (ADI-PEG20), Cancer Research, 70, AACR 101st Annual Meeting, Apr. 17-21, 2010, 2 pages.
Kim, J., et al., "Expression, purification, and characterization of arginine deiminase from *Lactococcus lactis* ssp. *lactis* ATCC7962 in *Escherichia coli* BL21," Protein Expr. Purif. (2007); 53: 9-15, doi:10.1016/j.pep.2006.12.002, 7 pages.
Kim, R. H. et al., "ADI, Autophagy and Apoptosis: Metabolic Stress as a Therapeutic Option for Prostate Cancer," Autophagy, 5(4):567-568 (2009).
Kim, R. H. et al., "Arginine Deiminase as a Novel Therapy for Prostate Cancer Induces Autophagy and Caspase-Independent Apoptosis," Cancer Research, 69(2):700-708 (2009).
Komada, Y., et al., "Apoptoptic Cell Death of Human T Lymphoblastoid Cells Induced by Arginine Deimanse," International Journal of Hematology, 65:129-141 (1997).
Kung, C., et al., "Autophagy in Tumor Suppression and Cancer Therapy," Critical Reviews in Eukaryotic Gene Expression, vol. 21, No. 1, 2011, pp. 71-100.
Matthews, B.W., "Structural and genetic analysis of protein stability", Annu. Rev. Biochem., 62: 139-160 (1993).
NCBI Acc# 4E4J_A from Gallego et al, 2012. Alignment with SEQ ID No. 8, 2 pages.
Ng and Henikoff, "Predicting the Effects of Amino Acid Substitutions on Protein Function", Annu. Rev. Genomics Hum. Genet., 7: 61-80 (2006).
Ni, Y. et al., "Arginine Deiminase, a Potential Anti-Tumor Drug," Cancer Letters 261:1-11 (2008).
Ni et al., "Rapid evolution of arginine deiminase for improved anti-tumor activity," Appl Microbiol Biotechnol., Jan. 11, 2011, vol. 90, No. 1, pp. 193-201.
NLM search https://chem.nlm.nih.gov/chemidplu&/rn/1394129-74-8 and "ADI-PEG 20" performed Aug. 2017, 1 page.
Noh, E-J. et al., "Arginine Deiminase Enhances Dexamethasone-Induced Cytotoxicity in Human T-Lymphoblastic Leukemia CCRF-CEM Cells," Int. J. Cancer, 112:502-508 (2004).
Ohno, T. et al., "Argininosuccinate Synthetase Gene Expression in Leukemias: Potential Diagnostic Marker for Blastic Crisis of Chronic Myelocytic Leukemia," Leukemia Research, 16(5):475-483 (1992).
Ott, P.A. et al., "Phase I/II study of pegylated arginine deiminase (ADI-PEG 20) in patients with advanced melanoma", Invest New Drugs, 31(2): 425-434 (2013).
Park, et al., "Pharmacology of *Escherichia coli*-L-asparaginase polyethylene glycol adduct." Anticancer Res. (1981); 1(6): 373-376.
Phillips, et al, "Targeting arginine-dependent cancers with arginine-degrading enzymes: opportunities and challenges." Cancer Res Treat. (2013); 45(4): 251-262.
Pinheiro, J. P. V. et al., "The best way to use asparaginase in childhood acute lymphatic leukaemia—still to be defined?", British Journal of Haematology, 125:117-127 (2004).
Poteete and Hardy, "Genetic Analysis of Bacteriophage T4 Lysozyme Structure and Function." Journal of Bacteriology, 176(22): 6783-6788 (1994).
Qiu, et al., "Targeting arginine metabolism pathway to treat arginine-dependent cancers." Cancer Lett. (2015); 364(1): 1-7.
Rodriguez, C. O. et al., "Abstract 4848: Pegylated arginine deiminase induces autophagy in canine melanoma and canine osteosarcoma," In: Proceedings of the 101st Annual Meeting of the American Association for Cancer Research, Apr. 17-21, 2010, Washington, DC, Philadelphia, PA: AACR Cancer Research, 70(8 Suppl.):Abstract nr 4848 (2010), 2 pages.
Savaraj, N., et al., "Arginine Deprivation, Autophagy, Apoptosis (AAA) for the Treatment of Melanoma," Current Molecular Medicine 2010, vol. 10, pp. 405-412.
Shen, L., et al., "Drug Evaluation: ADI-PEG-20—a PEGylated Arginine Deiminase for Arginine-Auxotrophic Cancers," Current Opinon in Molecular Therapeutics, 2006, vol. 8, No. 3, pp. 240-248.
Singapore Application No. 11201507354Q, Search Report and Written Opinion mailed Oct. 10, 2016, 16 pages.
Singapore Application No. 201307953-8, Search Report and Written Opinion mailed Jan. 26, 2016, 9 pages.
Sugimura et al., "Polymorphism in genes for the enzyme arginine deiminase among *Mycoplasma* species." Infect. Immun. Jan. 1, 1993, vol. 61, No. 1, pp. 329•331.
Sugimura, K., et al., "Elevated Argininosuccinate Synthetase Activity in Adult T Leukemia Cell Lines," Leukemia Research, vol. 14, No. 10, 1990, pp. 931-934.

(56) References Cited

OTHER PUBLICATIONS

Sugimura, K., et al., "Tumor Growth Inhibitory Activity of a Lymphocyte Blastogenesis Inhibitory Factor," Cancer Research, 50, Jan. 15, 1990, pp. 345-349.

Szlosarek, P., et al., "Abstract 4067: Pegylated Arginine Deiminase (ADI-PEG20) as a Potential Novel Therapy for Argininosuccinate Synthetase-Deficient Acute Myeloid Leukemia," Proceedings of the 102nd Annual Meeting of the American Associate for Cancer Research, Apr. 2-6, 2011, vol. 71, No. 8 (Supp), 2 pages.

Szlosarek, P., et al., "Effect of Inactivation of Argininosuccinate Synthetase on Sensitivity of Lymphomas to Caspase-Dependent Apoptosis Following Treatment with Arginine Deiminase," Journal of Clinical Oncology, vol. 28. No. 15 (May 20 Supp), 2010, 2 pages.

Szlosarek, P., et al., "In Vivo Loss of Expression of Argininosuccinate Synthetase in Malignant Pleural Mesothelioma is a Biomarker for Susceptibility to Arginine Depletion," Cancer Therapy: Preclinical, Clin Cancer Research, vol. 12, No. 23. Dec. 1, 2006, pp. 7123-7131.

Toxnet search "Pegargiminase", search initially performed Aug. 2017 and results accessed Oct. 11, 2017, 2 pages.

UniProtKB Submission F9UJU2_9MOLU, Arginine deiminase; Mycoplasma columbinum SF7 (Jan. 9, 2013). Retrieved from the Internet Jun. 22, 2014: <http://www.uniprot.org/uniprot/F9UJU2.txt?version=6>, 1 page.

UniProtKB/TrEMBL Submission A7LHN6_9MOLU (Jan. 9, 2013) Retrieved from the Internet Jun. 22, 2014: <http://www.uniprot.org/uniprot/A7LHN6.txt?version=28>, 1 page.

USPTO in house BLAST alignment ADI-PEG 20 (the variant of SEQ ID No. 1 herein consisting of the substitutions K112E and P21OS) alignment with SEQ ID No. 8. Performed May 10, 2016.

Venugopal, V. et al., "Histidine-dependent activation of arginine deiminase in clostridium sporogenes: Kinetic evidence on in vivo allosteric interactions," FEBS Letters, 51(1):246-248 (1975).

Wang, M. et al., "Engineering an arginine catabolizing bioconjugate: Biochemical and pharmacological characterization of PEGylated derivatives of arginine deiminase from mycoplasma arthritidis," Bioconjugate Chem., 17:1447-1459 (2006).

Weickmann and Fahrney. "Arginine deiminase from Mycoplasma arthritidis. Evidence for multiple forms." Journal of Biological Chemistry (1977); 252.8: 2615-2620.

Yang, T., et al., "A Randomised Phase II Study of Pegylated Arginine Deiminase (ADI-PEG 20) in Asian Advanced Hepatocellular Carcinoma Patients," British Journal of Cancer, vol. 103, 2010, pp. 954-960.

You, M. et al., "Abstract #3418: Arginine Deprivation and Soluble TRAIL Strikingly Enhance Death in Argininosuccinate Synthetase Negative Melanoma Cells," Proc. Am. Assoc. Cancer Research; Apr. 18-22, 2009, 2 pages.

You, M. et al., "Abstract 61: Enhancing Arginine Deprivation Therapy in Melanoma by Combining with Cisplatin," In: Proceedings of the 101st Annual Meeting of the American Association for Cancer Research, Apr. 17-21, 2010, Washington, DC, Philadelphia, PA: AACR Cancer Research; 70(8 Suppl.):Abstract nr 61, (2010), 2 pages.

You, M., et al., "Abstract 4096: TRAIL Enhances Cytotoxicity of Arginine Depletion Therapy in Argininosuccinate Synthetase-Negative Melanoma Cells Through Interruption of Autophagy Via Activation of Caspases," Proceedings of the 102nd Annual Meeting of the American Association for Cancer Research; Apr. 2-6, 2011, Cancer Research 2011, vol. 71, No. 8 (Supp), 2 pages.

You, M., et al., "The Combination of ADI-PEG20 and TRAIL Effectively Increases Cell Death in Melanoma Cell Lines," Biochemical and Biophysical Research Communications, 394:760-766 (2010).

Zamora, R. et al., "Inducible Nitric Oxide Synthase and Inflammatory Diseases," Molecular Medicine, 6(5):347-360 (2000).

Zeidan, A. et al., "Pegasparaginase: where do we stand?", Expert Opinion Biol. Ther, 9(1):111-119 (2009).

Zlotogorski, A. "Distribution of skin surface pH on the forehead and cheek of adults." Archives of Dermatological Research (1987); 279.6: 398-401.

[Author unknown] UniProt Acc#C4X3Y4, from Ishida et al, 2009, 5 pages.

[Author Unknown], NCBI Protein, Accession No. WP027332948, arginine deiminase [Mycoplasma gallinarum], [online] Jun. 12, 2014 uploaded. (GI:653082428) [Retrieved on May 13, 2019]. Retrieved from the internet:<URL:https://www.ncbi.nlm.nih.gov/protein/653082428?sat=46&satkey=171378155>, 1 page.

Bromberg and Rost, "Correlating protein function and stability through the analysis of single amino acid substitutions." BMC Bioinformatics (2009); 10(8): S8, 9 pages.

Frankel, et al., "Characterization of diphtheria fusion proteins targeted to the human interleukin-3 receptor." Protein Engineering, Design and Selection (2000); 13(8): 575-581.

International Preliminary Report on Patentability for International Application No. PCT/US2017/059732, dated May 7, 2019, 6 pages.

Lale, S.V., et al., "Development of lyophilization cycle and effect of excipients on the stability of catalase during lyophilization." Int J Pharm Investig. (2011); 1(4): 214-221.

Lockard, et al., "Efficacy and Toxicity of the Solvent Polyethylene Glycol 400 in Monkey Model." Epilepsia (1979); 20(1): 77-84.

Pakula and Sauer, "Genetic analysis of protein stability and function." Anna. Rev. Genet. (1989); 23: 289-310.

European Search Report dated May 28, 2020, corresponding to counterpart European Application No. 17866738.2; 7 pages.

English translation of Chinese Office Action issued on Sep. 29, 2021 in counterpart corresponding Chinese Application No. 20178006784.0; 12 pages.

Pak et al., "Formulation Approaches and Strategies for PEGylated Biotherapeutics," Sterile Product Development, (2013), Chapter 4; pp. 61-97.

Taiwanese Office Action and Search Report dated Nov. 5, 2021, corresponding to counterpart Taiwan Application No. 106137994; 6 total pages.

English Translation and Letters Patent for China Patent No. ZL 201780067842.0, Mar. 31, 2023, 3 pages.

English Translation and Letters Patent for Taiwanese Patent No. 1784982, Dec. 1, 2022, 2 pages.

Grant Certificate for European Patent No. 3534963, Apr. 17, 2024, 1 page.

Canadian Office Action for application No. 3,039,796, Apr. 15, 2024, 5 pages.

English translation of Taiwanese Office Action for application No. 111141486, Nov. 6, 2023, 9 pages.

Chinese Office Action for application No. 202310226603.2, Mar. 26, 2025, 10 pages, no translation available.

* cited by examiner

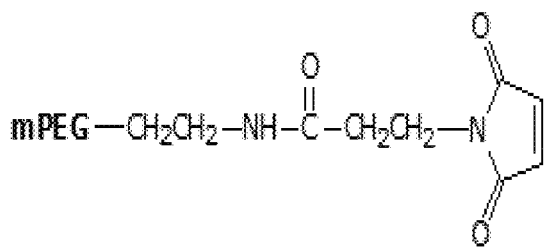

| ITEM CODE | ITEM NUMBER | ITEM DESCRIPTION |
|---|---|---|
| A3073-1 | M-MAL-2000,1g | Methoxy PEG Maleimide, MW 2000 |
| A3073-10 | M-MAL-2000,10g | Methoxy PEG Maleimide, MW 2000 |
| A3014-1 | M-MAL-5000,1g | Methoxy PEG Maleimide, MW 5000 |
| A3014-10 | M-MAL-5000,10g | Methoxy PEG Maleimide, MW 5000 |
| A3045-1 | M-MAL-10K,1g | Methoxy PEG Maleimide, MW 10000 |
| A3045-10 | M-MAL-10K,10g | Methoxy PEG Maleimide, MW 10000 |
| A3002-1 | M-MAL-20K,1g | Methoxy PEG Maleimide, MW 20000 |
| A3002-10 | M-MAL-20K,10g | Methoxy PEG Maleimide, MW 20000 |
| A3046-1 | M-MAL-30K,1g | Methoxy PEG Maleimide, MW 30000 |
| A3046-10 | M-MAL-30K,10g | Methoxy PEG Maleimide, MW 30000 |
| A3042-1 | M-MAL-40K,1g | Methoxy PEG Maleimide, MW 40000 |
| A3042-10 | M-MAL-40K,10g | Methoxy PEG Maleimide, MW 40000 |

FIG. 1A

SUNBRIGHT® MA Series (Maleimide PEGs)

C2 Type

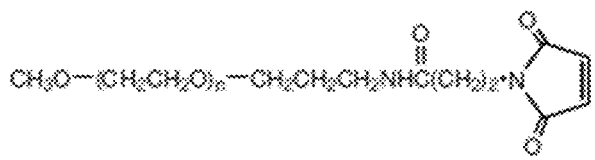

| Product Name | MW |
|---|---|
| SUNBRIGHT ME-020MA | 2,000 |
| SUNBRIGHT ME-050MA | 5,000 |
| SUNBRIGHT ME-100MA New | 10,000 |
| SUNBRIGHT ME-120MA | 12,000 |
| SUNBRIGHT ME-200MA | 20,000 |
| SUNBRIGHT ME-300MA | 30,000 |
| SUNBRIGHT ME-400MA | 40,000 |

C5 Type

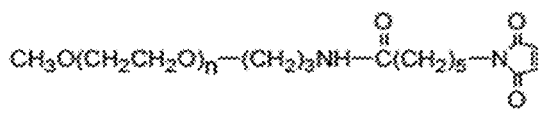

| Product Name | Functional Group | MW |
|---|---|---|
| SUNBRIGHT ME-050MA3 New | | 5,000 |
| SUNBRIGHT ME-120MA3 New | Maleimide | 12,000 |
| SUNBRIGHT ME-200MA3 New | -(CH2)3-NHCO-(CH2)5-Maleimide | 20,000 |
| SUNBRIGHT ME-400MA3 New | | 40,000 |

SUNBRIGHT® IA series (Iodoacetamide-PEG)

| Product Name | MW |
|---|---|
| SUNBRIGHT ME-200IA | 20,000 |
| SUNBRIGHT ME-300IA | 30,000 |
| SUNBRIGHT ME-400IA | 40,000 |

FIG. 1B

FORMULATIONS OF PEGYLATED ARGININE DEIMINASE

CROSS-REFERENCE TO RELATED APPLICATIONS

This application claims priority under 35 U.S.C. § 119(e) to U.S. Application No. 62/416,607, filed Nov. 2, 2016, which is incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is POLA-007_01US_ST25.txt. The text file is about 196 KB, was created on Jul. 2, 2018, and is being submitted electronically via EFS-Web.

BACKGROUND

Technical Field

Embodiments of the present disclosure relate, inter alia, to lyophilized formulations comprising pegylated arginine deiminase (ADI-PEG) and related reconstituted liquid compositions and methods of using the compositions for arginine depletion therapies, including for the treatment of various cancers.

Description of the Related Art

Arginine depletion therapy can be an effective treatment of certain forms of cancer, among other diseases. For instance, pegylated arginine deiminase (ADI-PEG) can be used to deplete the bloodstream supply of arginine by converting it to citrulline and ammonia. ADI-PEG 20 is an exemplary ADI-PEG that is being investigated in the clinic for tumors deficient in the key enzyme argininosuccinate synthetase-1 (ASS1), which is involved in the conversion of citrulline to arginine. ADI-PEG 20 has been well-tolerated and showed promise in clinical studies (see, e.g., Qiu et al., Cancer Lett. 2015 Aug. 1; 364(1):1-7; Phillips et al., Cancer Res Treat. 2013 December; 45(4):251-62; Feun et al., Curr Pharm Des. 2008; 14(11):1049-57; Feun and Savaraj, Expert Opin Investig Drugs. 2006 July; 15(7):815-22; Feun et al., Curr Opin Clin Nutr Metab Care. 2015 January; 18(1):78-82).

Lyophilization, or freeze drying, is a process that removes water from a liquid agent to create a solid powder, or cake. The preparation of lyophilized solid state or formulations represents one approach to optimizing the stability of biopharmaceutical agents. The use of lyophilized formulations can reduce degradative reactions, agitation during transportation, and the effects of temperature fluctuation during storage, among other benefits.

BRIEF SUMMARY

Certain embodiments relate to lyophilized formulations, comprising a pegylated arginine deiminase (ADI-PEG), wherein the lyophilized formulation is sterile, substantially endotoxin-free, and at a pharmaceutically-acceptable pH.

Some embodiments comprise a pharmaceutically-acceptable buffer, for example, a buffer selected from one or more of histidine, sodium citrate, glycyl-glycine, sodium phosphate, Tris, and lysine. In certain embodiments, the buffer is at a concentration of about 0.10 mM to about 200 mM, or about 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5, 5.0, 5.5, 6.0, 6.5. 7.0, 7.5, 8.0, 8.5, 9.0, 9.5, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 125, 130, 135, 140, 145, 150, 155, 160, 165, 170, 175, 180, 185, 190, 195, or 200 mM, including all integers and ranges in between. In particular embodiments, the buffer is at about 1 to about 50 mM, or about 10 to about 30 mM, or about 15 to about 25 mM, or about 20 mM, or about 10 mM.

Some embodiments comprise a pharmaceutically-acceptable excipient, for example, an excipient selected from one or more of a cryoprotectant, a lyoprotectant, a stabilizer, a bulking agent, a tonicity modifier, a surfactant, a pharmaceutical plasticizer, a chelator, and any combination of the foregoing.

In some embodiments, the cryoprotectant is present at about 0.001% to about 20% (wt %), including all integers and ranges in between. In some embodiments, the cryoprotectant is selected from one or more of sucrose, trehalose, ethylene glycol, propylene glycol, glycerol, and any combination of the foregoing.

In some embodiments, the lyoprotectant is present at about 0.001% to about 20% (wt %), including all integers and ranges in between. In some embodiments, the lyoprotectant is selected from one or more of sucrose, trehalose, mannitol, sorbitol, glycerol, and any combination of the foregoing.

In some embodiments, the stabilizer is present at about 0.001% to about 20% (wt %), including all integers and ranges in between. In certain embodiments, the stabilizer is selected from one or more of sucrose, mannitol, lactose, trehalose, maltose, sorbitol, gelatin, albumin, and any combination of the foregoing.

In certain embodiments, the bulking agent is present at about 0.001% to about 20% (wt %), including all integers and ranges in between. In certain embodiments, the bulking agent is selected from one or more of mannitol, sorbitol, lactose, glucose, sucrose, glycine, albumin, dextran 40.

In certain embodiments, the tonicity modifier is present at about 0.001% to about 20% (wt %), including all integers and ranges in between. In particular embodiments, the tonicity modifier is selected from one or more of sodium chloride, sucrose, mannitol, and any combination of the foregoing.

Particular lyophilized formulations comprise a pharmaceutically-acceptable excipient selected from one or more of sucrose, trehalose, dextran, mannitol, proline, glycine, a surfactant, a pharmaceutical plasticizer, a chelator, and any combination of the foregoing.

Certain lyophilized formulations comprise sucrose at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between.

Some lyophilized formulations comprise trehalose at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between.

Certain lyophilized formulations comprise dextran, optionally dextran 40, at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between.

Particular lyophilized formulations comprise mannitol at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between.

Some lyophilized formulations comprise proline at about 0.10 mM to about 200 mM, or about 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5, 5.0, 5.5, 6.0, 6.5. 7.0, 7.5, 8.0, 8.5, 9.0, 9.5, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 125, 130, 135, 140, 145, 150, 155, 160, 165, 170, 175, 180, 185, 190, 195, or 200 mM, or at about 0.001% to about 20%, or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between.

Certain lyophilized formulations comprise glycine at about 0.10 mM to about 200 mM, or about 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5, 5.0, 5.5, 6.0, 6.5. 7.0, 7.5, 8.0, 8.5, 9.0, 9.5, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 125, 130, 135, 140, 145, 150, 155, 160, 165, 170, 175, 180, 185, 190, 195, or 200 mM, or at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between.

Certain lyophilized formulations comprise a surfactant at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between. In some embodiments, the surfactant is selected from one or more of Tween-80, polysorbate 20 (P20), polysorbate 80 (P80), poloxamer 188, and any combination of the foregoing.

Some lyophilized formulations comprise a pharmaceutical plasticizer at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between. In certain embodiments, the pharmaceutical plasticizer is glycerol.

Certain lyophilized formulations comprise a chelator, for example, ethylenediaminetetraacetic acid (EDTA). In some embodiments, the chelator is present at about 0.001% to about 1% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0%, including all integers and ranges in between.

In certain embodiments, the pharmaceutically-acceptable pH is about 5.0 to about 8.0 (±0.01 to ±0.1), or about 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, or 8.0 (±0.01 to ±0.1), including all integers and ranges in between.

In specific embodiments, the buffer is histidine at a concentration of about 1 to about 50 mM, or about 10 to about 30 mM, or about 15 to about 25 mM, or about 20 mM.

Certain of these and related embodiments comprise sucrose at about 1% to about 10%, or about 4% to about 6%, or about 5%. Some embodiments comprise mannitol at about 1% to about 10%, or about 4% to about 6%, or about 5%. Some embodiments comprise dextran, for example, dextran 40, at about 0.1% to about 5%, or about 0.5% to about 2%, or about 1%. Some embodiments comprise dextran, for example, dextran 40, at about 0.1% to about 5%, or about 0.5% to about 2%, or about 1%, and comprising sucrose at about 1% to about 10%, or about 4% to about 6%, or about 5%. Some embodiments comprise trehalose at about 1% to about 10%, or about 4% to about 6%, or about 5%. Some embodiments comprise mannitol at about 1% to about 10%, or about 3% to about 5%, or about 4%, and comprising sucrose at about 0.1% to about 5%, or about 0.5% to about 2%, or about 1%. Some embodiments comprise sucrose at about 1% to about 10%, or about 4% to about 6%, or about 4.8% or 5%, and comprising Tween-80 at about 0.001% to about 0.1%, or about 0.005% to about 0.05%, or about 0.01%. Some embodiments comprise sucrose at about 1% to about 10%, or about 4% to about 6%, or about 4.8% or 5%, comprising Tween-80 at about 0.001% to about 0.1%, or about 0.005% to about 0.05%, or about 0.01%, and comprising glycerol at about 0.01% to about 1.0%, or about 0.1% to about 0.5%, or about 0.25%. In some of these and related embodiments, the pH is about 6.0 to about 6.5 to about 7.2 (±0.1), or at about 6.6 to about 7.0 (±0.1), or about 6.8 (±0.1).

Some embodiments comprise trehalose at about 1% to about 15%, or about 5% to about 12%, or about 10% or 9.5%. Some embodiments comprise trehalose at about 1% to about 15%, or about 5% to about 12%, or about 10% or 9.5%, and comprising proline at about 10 mM to about 40 mM, or about 15 to about 30 mM, or about 20 mM. Some embodiments comprise trehalose at about 5% to about 15%, or about 8% to about 12%, or about 10% or 9.5%, and comprising glycine at about 10 mM to about 40 mM, or about 15 to about 30 mM, or about 20 mM. Some embodiments comprise sucrose at about 1% to about 15%, or about 5% to about 12%, or about 10% or 9.5%. Some embodiments comprise sucrose at about 1% to about 10%, about 4% to about 6%, or about 5% or 4.5%, and comprising trehalose at about 1% to about 10%, about 4% to about 6%, or about 5% or 4.5%. Some embodiments comprise trehalose at about 5% to about 15%, or about 8% to about 12%, or about 10% or 9.5%, and comprising EDTA at about 0.01% to about 0.1%, or about 0.02% to about 0.08%, or about 0.05%. In some of these and related embodiments, the pH is about 6.0 to about 7.2 (±0.1), or at about 6.4 to about 6.8 (±0.1), or about 6.5 (±0.1).

In certain embodiments, the buffer is histidine at about 1 to about 30 mM, or about 5 to about 20 mM, or about 10 mM, comprising glycine at about 1% to about 5%, or about 2% or 1.9%, comprising trehalose at about 0.1% to about 2%, or about 0.5% to about 1.5%, or about 1%, and comprising a surfactant, for example, P20, at about 0.001% to about 0.1%, or about 0.005% to about 0.02%, or about 0.01%. In certain embodiments, the buffer is histidine at about 1 to about 30 mM, or about 5 to about 20 mM, or about 10 mM, comprising sucrose at about 1% to about 15%, or about 5% to about 12%, or about 10% or 8.5%, and comprising trehalose at about 0.1% to about 2%, or about 0.5% to about 1.5%, or about 1%. In certain embodiments, the buffer is histidine at about 1 to about 30 mM, or about 5 to about 20 mM, or about 10 mM, comprising sucrose at about 1% to about 15%, or about 5% to about 12%, or about 10% or 9%. In certain embodiments, the buffer is histidine at about 1 to about 50 mM, or about 10 to about 40 mM, or about 20, 25, 30, or 35 mM, comprising sodium chloride at about 100 to about 150 mM, or about 120, 130, or 140 mM. In some embodiments, the buffer is sodium phosphate at about 100 to about 200 mM, or about 150 mM, comprising sucrose and/or trehalose at about 1% to about 10%, about 4% to about 6%, or about 5% or 4.5%, comprising glycine at about 0.1 to about 1%, or about 0.5%, comprising glycerol at about 0.1 to about 1.0%, or about 0.25%, comprising Tween 80 at about 0.001 to about 0.1%, or about 0.01%, and comprising EDTA at about 0.01 to about 0.1%, or about 0.05%. In certain embodiments, the pH is about 6.0 to about 6.5 to about 7.2 (±0.1), or at about 6.6 to about 7.0 (±0.1), or about 6.8 (±0.1).

In some embodiments, the dry weight of the ADI-PEG is about 50 mg/g to about 150 mg/g. In some embodiments, the ADI-PEG comprises an amino acid sequence that is at least 80, 95, 90, 95, 96, 97, 98, 99, or 100% identical to a sequence in Table A1. In some embodiments, the ADI-PEG is covalently bonded to about 1 to about 21 PEG molecules. In some embodiments, the ADI-PEG comprises one or more water-labile linkers which covalently attach the ADI and PEG. In some embodiments, the ADI-PEG is ADI-PEG 20, wherein the arginine deiminase is covalently bonded to a mass average of about 5±1.0 PEG molecules.

In some embodiments, the ADI-PEG retains at least 80, 85, 90, or 95% of its arginine deiminase (ADI) activity relative to a corresponding ADI-PEG in a non-lyophilized liquid control composition. In some embodiments, the ADI-PEG retains at least 50, 55, 60, 65, 70, 75, 80, 85, 90, 95, or 100% of the (original) PEG molecules (per ADI monomer/protomer), for example, relative to a corresponding ADI-PEG in a non-lyophilized liquid control composition.

Also included are methods of reconstituting a lyophilized formulation described herein, comprising adding a pharmaceutically-acceptable solvent to the lyophilized formulation to form a reconstituted liquid composition.

In some embodiments, the lyophilized formulation is reconstituted to a substantially aggregate-free solution of about 5-20 mg/ml ADI-PEG in a time of less than about five minutes. In some embodiments, the lyophilized formulation is reconstituted to a substantially aggregate-free solution of about 5-20 mg/ml ADI-PEG in a time of less than about one or two minutes.

In some embodiments, the ADI-PEG in the reconstituted liquid composition retains at least 75, 80, 85, 90, or 95% of its arginine deiminase activity, and/or retains at least 50, 55, 60, 65, 70, 75, 80, 85, 90, 95, or 100% of the PEG molecules (per ADI monomer/protomer), relative to a corresponding ADI-PEG in a non-lyophilized liquid control composition. In some embodiments, the ADI-PEG retains at least 75, 80, 85, 90, or 95% of its arginine deiminase activity upon reconstitution after being stored as a lyophilized formulation for about or at least about 1, 2, 3, 4, 5, 6, 7, 8, 9, 10, 11, 12, 13, 14, 15, 16, 17, 18, 19, 20, 21, 22, 23, 24, 36, 48, 60, or 72 months, for example, after being stored at a temperature of about 2-8° C. and/or about room temperature. In some embodiments, the ADI-PEG retains at least 50, 55, 60, 65, 70, 75, 80, 85, 90, 95, or 100% of the (original) PEG molecules (per ADI monomer/protomer) after being stored as a lyophilized formulation for about or at least about 1, 2, 3, 4, 5, 6, 7, 8, 9, 10, 11, 12, 13, 14, 15, 16, 17, 18, 19, 20, 21, 22, 23, 24, 36, 48, 60, or 72 months, for example, after being stored at a temperature of about 2-8° C. and/or about room temperature. In some embodiments, the specific enzyme activity of the ADI-PEG after reconstitution is about 5.0 to about 120 IU/mg, or about 5.5, 6, 6.5, 7, 7.5, 8, 8.5, 9.0, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 35, 40, 45, 50, 55, 55, 60, 65, 70, 75, 80, 85, 90, 95, 100, 105, 110, 115, or 120 IU/mg.

In some embodiments, the ADI-PEG has an osmolality of about 50 mOsm/kg to about 500 mOsm/kg, or about 50, 55, 60, 65, 70, 75, 80, 85, 90, 95, 100, 105, 110, 120, 125, 130, 135, 140, 145, 150, 155, 160, 165, 170, 175, 180, 185, 190, 195, 200, 205, 210, 220, 225, 230, 235, 240, 245, 250, 255, 260, 265, 270, 275, 280, 285, 290, 295, 300, 305, 310, 320, 325, 330, 335, 340, 345, 350, 355, 360, 365, 370, 375, 380, 385, 390, 395, 400, 405, 410, 420, 425, 430, 435, 440, 445, 450, 455, 460, 465, 470, 475, 480, 485, 490, 495, or about 500 mOsm/kg.

In specific embodiments, the solvent is water.

Certain embodiments relate to reconstituted liquid compositions prepared by any of the methods described herein.

Some embodiments include a reconstituted liquid composition, comprising a lyophilized formulation described herein and a pharmaceutically-acceptable solvent. In some embodiments, the ADI-PEG is at a concentration of about 5-20 mg/ml, or about 5, 6, 7, 8, 9, 10, 10.5, 11, 11.5, 12, 12.5, 13, 13.5, 14, 15, 16, 17, 18, 19, or 20 mg/ml, including all integers and ranges in between. In some embodiments, the ADI-PEG in the reconstituted liquid composition retains at least 75, 80, 85, 90, or 95% of its arginine deiminase activity relative to a corresponding ADI-PEG in a non-lyophilized liquid control composition.

In some embodiments, the specific enzyme activity of the ADI-PEG is about 5.0 to about 120 IU/mg, or about 5.5, 6, 6.5, 7, 7.5, 8, 8.5, 9.0, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 35, 40, 45, 50, 55, 55, 60, 65, 70, 75, 80, 85, 90, 95, 100, 105, 110, 115, or 120 IU/mg.

In some embodiments, the ADI-PEG has an osmolality of about 50 mOsm/kg to about 500 mOsm/kg, or about 50, 55, 60, 65, 70, 75, 80, 85, 90, 95, 100, 105, 110, 120, 125, 130, 135, 140, 145, 150, 155, 160, 165, 170, 175, 180, 185, 190, 195, 200, 205, 210, 220, 225, 230, 235, 240, 245, 250, 255, 260, 265, 270, 275, 280, 285, 290, 295, 300, 305, 310, 320, 325, 330, 335, 340, 345, 350, 355, 360, 365, 370, 375, 380, 385, 390, 395, 400, 405, 410, 420, 425, 430, 435, 440, 445, 450, 455, 460, 465, 470, 475, 480, 485, 490, 495, or about 500 mOsm/kg.

In some embodiments, the solvent is water. Certain reconstituted solutions are suitable for injection into a subject.

Also included are methods of treating, ameliorating the symptoms of, or inhibiting the progression of, a cancer in a subject in need thereof, comprising administering to the subject a reconstituted liquid formulation described herein.

In certain embodiments, the cancer is selected from one or more of hepatocellular carcinoma (HCC), melanoma, metastatic melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, B-cell malignancy, breast cancer, ovarian cancer, colorectal cancer, gastric cancer, glioma (e.g., astrocytoma, oligodendroglioma, ependymoma, or a choroid plexus papilloma), glioblastoma multiforme (e.g., giant cell gliobastoma or a gliosarcoma), meningioma, pituitary adenoma, vestibular schwannoma, primary CNS lymphoma, primitive neuroectodermal tumor (medulloblastoma), non-small cell lung cancer (NSCLC), kidney cancer, bladder cancer, uterine cancer, esophageal cancer, brain cancer, head and neck cancers, cervical cancer, testicular cancer, and stomach cancer.

In some embodiments, the cancer exhibits reduced expression of argininosuccinate synthetase-1.

Certain embodiments include one or more patient care kits, comprising a lyophilized formulation described herein, and optionally a pharmaceutically-acceptable solvent. In specific embodiments, the solvent is water.

BRIEF DESCRIPTION OF THE DRAWINGS

FIGS. 1A-1D illustrate a variety of cysteine-reactive PEG molecules that can be conjugated to the ADI polypeptides described herein.

DETAILED DESCRIPTION

Figure 1C:
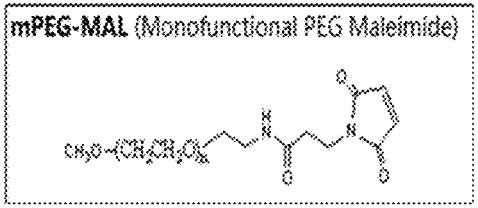
Figure 1C:
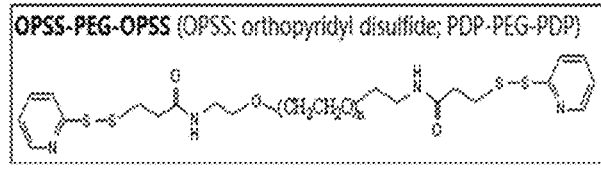
Figure 1C:
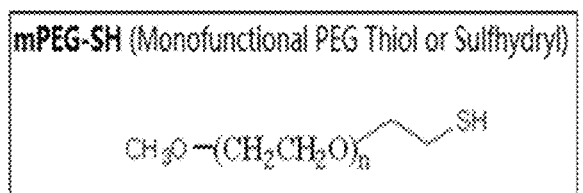
Figure 1C:
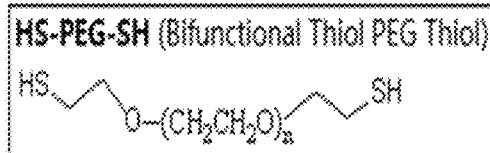
Figure 1C:
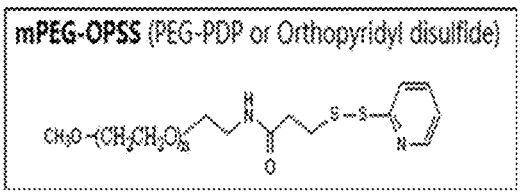
Figure 1C:
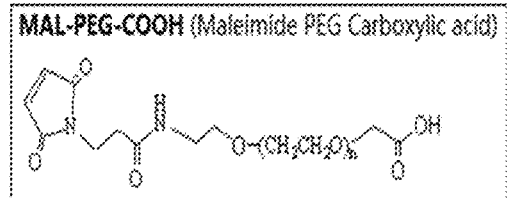
Figure 1C:
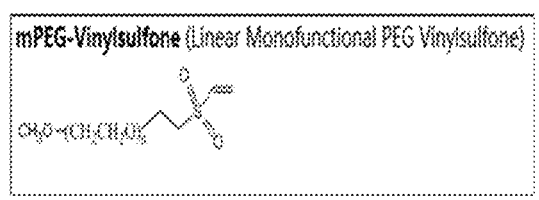
Figure 1C:
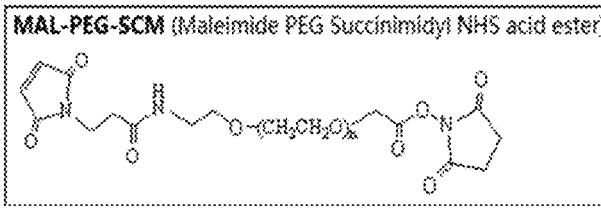
Figure 1C:
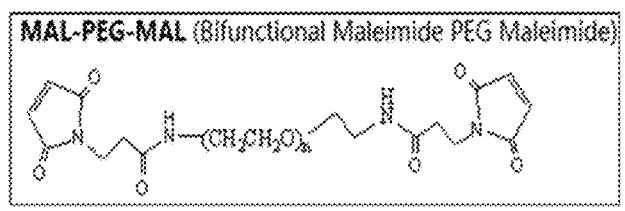
Figure 1C:
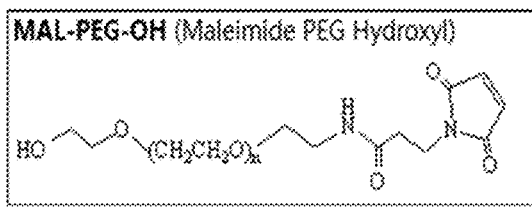
Figure 1C:
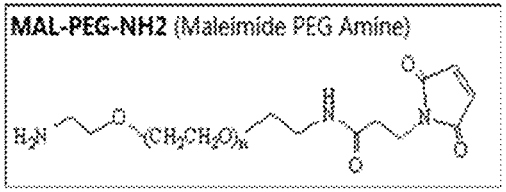
Figure 1C:
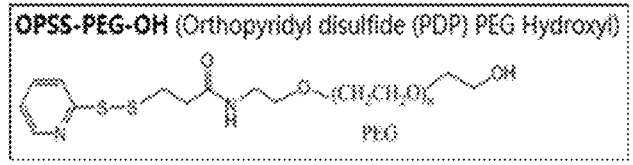
Figure 1C:
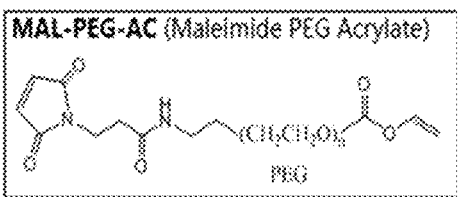
Figure 1C:
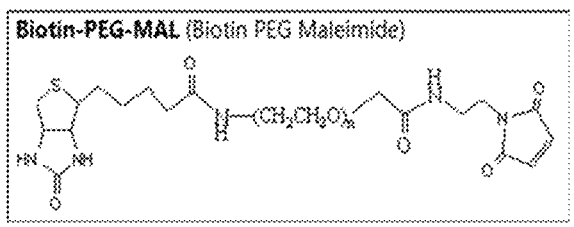
Figure 1C:
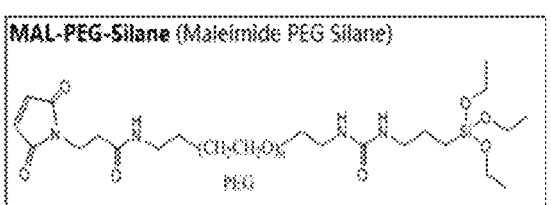
Figure 1C:
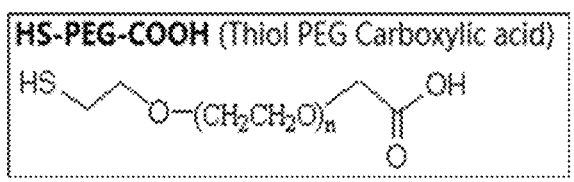
Figure 1C:
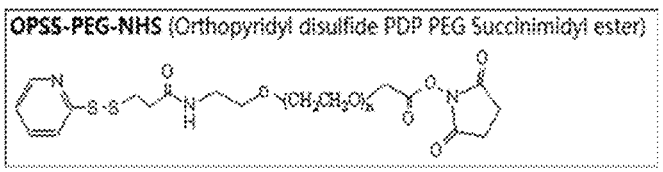
Figure 1C:
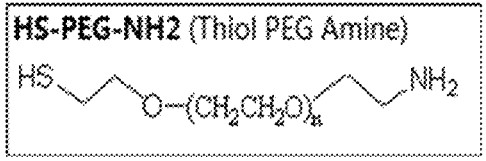
Figure 1C:
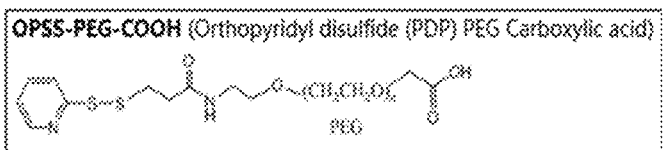
Figure 1C:
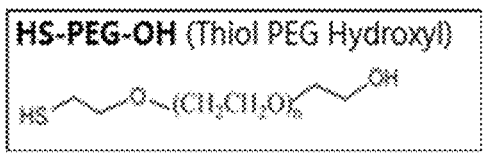
Figure 1C:
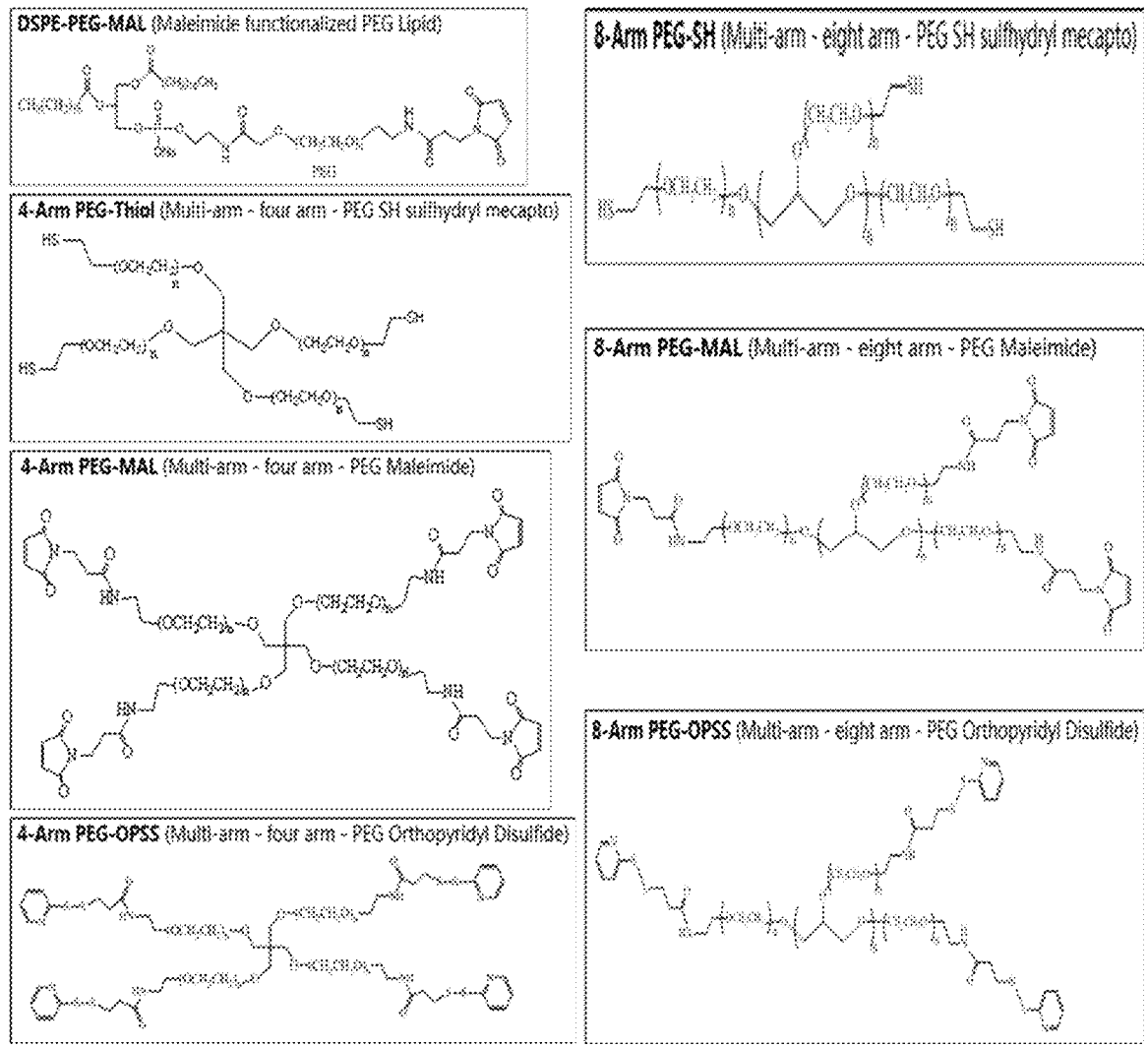

Unless defined otherwise, all technical and scientific terms used herein have the same meaning as commonly understood by those of ordinary skill in the art to which the disclosure belongs. Although any methods, materials, compositions, reagents, cells, similar or equivalent similar or equivalent to those described herein can be used in the practice or testing of the subject matter of the present disclosure, preferred methods and materials are described. All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

The practice of the present disclosure will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., *Current Protocols in Protein Science, Current Protocols in Molecular Biology* or *Current Protocols in Immunology*, John Wiley & Sons, New York, N.Y. (2009); Ausubel et al., *Short Protocols in Molecular Biology*, 3rd ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the e-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

"Biocompatible" refers to materials or compounds which are generally not injurious to biological functions and which will not result in any degree of unacceptable toxicity, including allergenic and disease states.

By "coding sequence" is meant any nucleic acid sequence that contributes to the code for the polypeptide product of a gene. By contrast, the term "non-coding sequence" refers to any nucleic acid sequence that does not directly contribute to the code for the polypeptide product of a gene.

Throughout this disclosure, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "endotoxin free" or "substantially endotoxin free" relates generally to compositions, solvents, and/or vessels that contain at most trace amounts (e.g., amounts having no clinically adverse physiological effects to a subject) of endotoxin, and preferably undetectable amounts of endotoxin. Endotoxins are toxins associated with certain micro-organisms, such as bacteria, typically gram-negative bacteria, although endotoxins may be found in gram-positive bacteria, such as *Listeria monocytogenes*. The most prevalent endotoxins are lipopolysaccharides (LPS) or lipo-oligo-saccharides (LOS) found in the outer membrane of various Gram-negative bacteria, and which represent a central pathogenic feature in the ability of these bacteria to cause disease. Small amounts of endotoxin in humans may produce fever, a lowering of the blood pressure, and activation of inflammation and coagulation, among other adverse physiological effects.

Therefore, in pharmaceutical production, it is often desirable to remove most or all traces of endotoxin from drug products and/or drug containers, because even small amounts may cause adverse effects in humans. A depyrogenation oven may be used for this purpose, as temperatures in excess of 300° C. are typically required to break down most endotoxins. For instance, based on primary packaging material such as syringes or vials, the combination of a glass temperature of 250° C. and a holding time of 30 minutes is often sufficient to achieve a 3 log reduction in endotoxin levels. Other methods of removing endotoxins are contemplated, including, for example, chromatography and filtration methods, as described herein and known in the art.

Endotoxins can be detected using routine techniques known in the art. For example, the *Limulus* Amoebocyte Lysate assay, which utilizes blood from the horseshoe crab, is a very sensitive assay for detecting presence of endotoxin. In this test, very low levels of LPS can cause detectable coagulation of the limulus lysate due a powerful enzymatic cascade that amplifies this reaction. Endotoxins can also be quantitated by enzyme-linked immunosorbent assay (ELISA). To be substantially endotoxin free, endotoxin levels may be less than about 0.001, 0.005, 0.01, 0.02, 0.03, 0.04, 0.05, 0.06, 0.08, 0.09, 0.1, 0.5, 1.0, 1.5, 2, 2.5, 3, 4, 5, 6, 7, 8, 9, or 10 EU/mg of active compound. Typically, 1 ng lipopolysaccharide (LPS) corresponds to about 1-10 EU.

The "half-life" of a polypeptide can refer to the time it takes for the polypeptide to lose half of its pharmacologic, physiologic, or other activity, relative to such activity at the time of administration into the serum or tissue of an organism, or relative to any other defined time-point. "Half-life" can also refer to the time it takes for the amount or concentration of a polypeptide to be reduced by half of a starting amount administered into the serum or tissue of an organism, relative to such amount or concentration at the time of administration into the serum or tissue of an organism, or relative to any other defined time-point. The half-life can be measured in serum and/or any one or more selected tissues.

The terms "modulating" and "altering" include "increasing," "enhancing" or "stimulating," as well as "decreasing" or "reducing," typically in a statistically significant or a physiologically significant amount or degree relative to a control. An "increased," "stimulated" or "enhanced" amount is typically a "statistically significant" amount, and may include an increase that is 1.1, 1.2, 2, 3, 4, 5, 6, 7, 8, 9, 10, 15, 20, 30 or more times (e.g., 500, 1000 times) (including all integers and ranges in between e.g., 1.5, 1.6, 1.7. 1.8, etc.) the amount produced by no composition (e.g., the absence of agent) or a control composition. A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) in the amount produced by no composition (e.g., the absence of an agent) or a control composition. Examples of comparisons and "statistically significant" amounts are described herein.

The terms "polypeptide," "protein" and "peptide" are used interchangeably and mean a polymer of amino acids not limited to any particular length. The term "enzyme" includes polypeptide or protein catalysts, and with respect to ADI is used interchangeably with protein, polypeptide, or peptide. The terms include modifications such as myristoylation, sulfation, glycosylation, phosphorylation and addition or deletion of signal sequences. The terms "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. The terms "polypeptide" and "protein" specifically encompass the ADI enzymes/proteins described herein, or sequences that have deletions from, additions to, and/or substitutions of one or more amino acid of the ADI proteins. In certain embodiments, the polypeptide is a "recombinant" polypeptide, produced by recombinant cell that comprises one or more recombinant DNA molecules, which are typically made of heterologous polynucleotide sequences or combinations of polynucleotide sequences that would not otherwise be found in the cell.

The term "isolated" polypeptide or protein referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or non-covalent interaction) with portions of a protein with which the "isolated protein" is associated in nature, (6) is operably associated (by covalent or non-covalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially free from proteins or polypeptides or other contaminants that are found in its natural environment that would interfere with its use (therapeutic, diagnostic, prophylactic, research or otherwise).

In certain embodiments, the "purity" of any given agent (e.g., ADI-PEG) in a composition may be specifically defined. For instance, certain compositions may comprise an agent that is at least 70, 75 80, 85, 90, 91, 92, 93, 94, 95, 96, 97, 98, 99, or 100% pure (for example, on a protein basis), including all decimals and ranges in between, as measured, for example, by high performance liquid chromatography (HPLC), a well-known form of column chromatography used frequently in biochemistry and analytical chemistry to separate, identify, and quantify compounds.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., Nucl. Acids Res. 25:3389, 1997.

The term "solubility" refers to the property of an agent (e.g., ADI-PEG) provided herein to dissolve in a liquid solvent and form a homogeneous solution. Solubility is typically expressed as a concentration, either by mass of solute per unit volume of solvent (g of solute per kg of solvent, g per dL (100 mL), mg/ml, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, pH 7.4, pH 7.6, pH 7.8, or pH 8.0 (e.g., about pH 5-8). In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (37° C.). In certain embodiments, an agent has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, 30, 40, 50, 60, 70, 80, 90 or 100 mg/ml at room temperature or at 37° C.

A "subject" or a "subject in need thereof" or a "patient" or a "patient in need thereof" includes a mammalian subject such as a human subject.

"Substantially" or "essentially" means nearly totally or completely, for instance, 95%, 96%, 97%, 98%, 99% or greater of some given quantity.

By "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

"Therapeutic response" refers to improvement of symptoms (whether or not sustained) based on administration of one or more therapeutic agents.

As used herein, "treatment" of a subject (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

The term "wild-type" refers to a gene or gene product (e.g., a polypeptide) that is most frequently observed in a population and is thus arbitrarily designed the "normal" or "wild-type" form of the gene.

Each embodiment in this specification is to be applied mutatis mutandis to every other embodiment unless expressly stated otherwise.

Throughout the present disclosure, the following abbreviations may be used: PEG, polyethylene glycol; ADI, arginine deiminase; SS, succinimidyl succinate; SSA, succinimidyl succinimide; SPA, succinimidyl propionate; NHS, N-hydroxy-succinimide; ASS-1, argininosuccinate synthetase-1.

Lyophilized Formulations

Certain embodiments relate to lyophilized formulations, comprising a pegylated arginine deiminase (ADI-PEG), wherein the lyophilized formulation is sterile, substantially endotoxin-free, and at a pharmaceutically-acceptable pH. In some embodiments, the formulation comprises a pharmaceutically-acceptable buffer. In certain embodiments, the formulation comprises one or more pharmaceutically-acceptable excipients, including, for example, one or more cryoprotectants, lyoprotectants, stabilizers, bulking agents, tonicity modifiers, surfactants, pharmaceutical plasticizers, or chelators, including any combination of the foregoing.

Some formulations comprise one or more pharmaceutically-acceptable buffers. In certain embodiments, the buffer is at a concentration of about 0.10 mM to about 200 mM, or about 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5, 5.0, 5.5, 6.0, 6.5. 7.0, 7.5, 8.0, 8.5, 9.0, 9.5, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 125, 130, 135, 140, 145, 150, 155, 160, 165, 170, 175, 180, 185, 190, 195, or 200 mM, including all integers and ranges in between. In particular embodiments, the buffer is at a concentration of about 1 mM to about 50 mM, or about 10 mM to about 30 mM, or about 15 mM to about 25 mM, or about 10 mM to about 20 mM, or about 20 mM, or about 10 mM. In particular embodiments, the buffer is selected from one or more of histidine, sodium citrate, glycylglycine, sodium phosphate, Tris, lysine, and any combination of the foregoing.

In specific embodiments, the formulation comprises a histidine buffer at about 1 to about 50 mM, or about 10 to about 30 mM, or about 15 to about 25 mM, or about 20 mM. In some embodiments, the formulation comprises a sodium citrate at about 1 to about 50 mM, or about 10 to about 30 mM, or about 15 to about 25 mM, or about 20 mM. In particular embodiments, the formulation comprises a glycylglycine buffer at about 1 to about 50 mM, or about 10 to about 30 mM, or about 15 to about 25 mM, or about 20 mM. In specific embodiments, the formulation comprises a sodium phosphate buffer at about 1 to about 50 mM, or about 10 to about 30 mM, or about 15 to about 25 mM, or about 20 mM. In some embodiments, the formulation comprises a Tris buffer at about 1 to about 50 mM, or about 10 to about 30 mM, or about 15 to about 25 mM, or about 20 mM. In certain embodiments, the formulation comprises a lysine buffer at about 1 to about 50 mM, or about 10 to about 30 mM, or about 15 to about 25 mM, or about 20 mM.

Some formulations comprise one or more cryoprotectants. A "cryoprotectant" refers to a pharmaceutically-acceptable substance or excipient that protects the active agent(s) during the freezing stage(s) of lyophilization. In some embodiments, the cryoprotectant is present at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between. In specific embodiments, the cryoprotectant is selected from one or more of sucrose, trehalose, ethylene glycol, propylene glycol, glycerol, and any combination of the foregoing.

Certain formulations comprise one or more lyoprotectants. A "lyoprotectant" refers to a pharmaceutically-acceptable substance or excipient that protects the active agent(s) during the drying stage(s) of lyophilization. In some embodiments, the lyoprotectant is present at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between. In specific embodiments, the lyoprotectant is selected from one or more of sucrose, trehalose, mannitol, sorbitol, glycerol, and any combination of the foregoing.

Certain formulations comprise one or more pharmaceutically-acceptable stabilizers. In some embodiments, the stabilizer is present at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between. In some embodiments, the stabilizer is selected from one or more of sucrose, mannitol, lactose, trehalose, maltose, sorbitol, gelatin, albumin, and any combination of the foregoing.

Some formulations comprise one or more pharmaceutically-acceptable bulking agents. In some embodiments, the bulking agent is present at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between. In specific embodiments, the bulking agent is selected from one or more of mannitol, sorbitol, lactose, glucose, sucrose, glycine, albumin, dextran 40, and any combination of the foregoing.

Some formulations comprise one or more pharmaceutically-acceptable tonicity modifiers. In some embodiments, the tonicity modifier is present at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, or at a concentration of about 0.10 mM to about 200 mM, or about 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5, 5.0, 5.5, 6.0, 6.5. 7.0, 7.5, 8.0, 8.5, 9.0, 9.5, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 125, 130, 135, 140, 145, 150, 155, 160, 165, 170, 175, 180, 185, 190, 195, or 200 mM, including all integers and ranges in between. In particular embodiments, the tonicity modifier is selected from one or more of sodium chloride, sucrose, mannitol, and any combination of the foregoing.

In certain embodiments, the formulation comprises one or more surfactants. In some embodiments, surfactant is present at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%. Exemplary surfactants include Tween-80, polysorbate 20 (P20), polysorbate 80 (P80), poloxamer 188, and combinations thereof.

Certain formulations comprise one or more pharmaceutical plasticizers. In some embodiments, the pharmaceutical plasticizer is present at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, including all integers and ranges in between. In particular embodiments, the pharmaceutical plasticizer is glycerol.

Some formulations comprise one or more chelators. In some embodiments, the chelator is present at about 0.001% to about 1% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, or 1.0%, including all integers and ranges in between. In specific embodiments, the chelator is ethylenediaminetetraacetic acid (EDTA).

Particular formulations comprise a pharmaceutically-acceptable excipient selected from one or more of sucrose, trehalose, dextran, mannitol, proline, glycine, a surfactant, a pharmaceutical plasticizer, a chelator, and any combination of the foregoing. For example, in some embodiments the sucrose, trehalose, dextran (for example dextran 40), mannitol, proline, and/or glycine is present at about 0.001% to about 20% (wt %), or about 0.001, 0.002, 0.003, 0.004, 0.005, 0.006, 0.007, 0.008, 0.009, 0.010, 0.015, 0.020, 0.025, 0.030, 0.035, 0.040, 0.045, 0.050, 0.055, 0.060, 0.065, 0.070, 0.075, 0.080, 0.085, 0.090, 0.095, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.1, 1.2, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20%, or at a concentration of about 0.10 mM to about 200 mM, or about 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1.0, 1.5, 2.0, 2.5, 3.0, 3.5, 4.0, 4.5, 5.0, 5.5, 6.0, 6.5. 7.0, 7.5, 8.0, 8.5, 9.0, 9.5, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 125, 130, 135, 140, 145, 150, 155, 160, 165, 170, 175, 180, 185, 190, 195, or 200 mM, including all integers and ranges in between.

In specific embodiments, as noted above, the formulation comprises a histidine buffer at about 1 to about 50 mM, or about 10 to about 30 mM, or about 15 to about 25 mM, or about 20 mM.

In some embodiments, the formulation comprises a histidine buffer at about 1 to about 50 mM, or about 10 to about 30 mM, or about 15 to about 25 mM, or about 20 mM, and comprises sucrose at about 1% to about 10%, or about 4% to about 6%, or about 5%.

In some embodiments, the formulation comprises a histidine buffer at about 1 to about 50 mM, or about 10 to about 30 mM, or about 15 to about 25 mM, or about 20 mM, and comprises mannitol at about 1% to about 10%, or about 4% to about 6%, or about 5%.

In some embodiments, the formulation comprises a histidine buffer at about 1 to about 50 mM, or about 10 to about 30 mM, or about 15 to about 25 mM, or about 20 mM, and comprises dextran, for example, dextran 40, at about 0.1% to about 5%, or about 0.5% to about 2%, or about 1%.

In particular embodiments, the formulation comprises a histidine buffer at about 1 to about 50 mM, or about 10 to about 30 mM, or about 15 to about 25 mM, or about 20 mM, and comprises dextran, example, dextran 40, at about 0.1% to about 5%, or about 0.5% to about 2%, or about 1%, and comprises sucrose at about 1% to about 10%, or about 4% to about 6%, or about 5%.

In certain embodiments, the formulation comprises a histidine buffer at about 1 to about 50 mM, or about 10 to about 30 mM, or about 15 to about 25 mM, or about 20 mM, and comprises trehalose at about 1% to about 10%, or about 4% to about 6%, or about 5%.

In some embodiments, the formulation comprises a histidine buffer at about 1 to about 50 mM, or about 10 to about 30 mM, or about 15 to about 25 mM, or about 20 mM, and comprises mannitol at about 1% to about 10%, or about 3% to about 5%, or about 4%, and comprising sucrose at about 0.1% to about 5%, or about 0.5% to about 2%, or about 1%.

In some embodiments, the formulation comprises a histidine buffer at about 1 to about 50 mM, or about 10 to about 30 mM, or about 15 to about 25 mM, or about 20 mM, and comprises sucrose at about 1% to about 10%, or about 4% to about 6%, or about 4.8% or 5%, and comprising Tween-80 at about 0.001% to about 0.1%, or about 0.005% to about 0.05%, or about 0.01%.

In some embodiments, the formulation comprises a histidine buffer at about 1 to about 50 mM, or about 10 to about 30 mM, or about 15 to about 25 mM, or about 20 mM, and comprises sucrose at about 1% to about 10%, or about 4% to about 6%, or about 4.8% or 5%, comprising Tween-80 at about 0.001% to about 0.1%, or about 0.005% to about 0.05%, or about 0.01%, and comprising glycerol at about 0.01% to about 1.0%, or about 0.1% to about 0.5%, or about 0.25%.

In some embodiments, the formulation comprises a histidine buffer at about 1 to about 50 mM, or about 10 to about 30 mM, or about 15 to about 25 mM, or about 20 mM, and comprises trehalose at about 1% to about 15%, or about 5% to about 12%, or about 10% or 9.5%.

In some embodiments, the formulation comprises a histidine buffer at about 1 to about 50 mM, or about 10 to about 30 mM, or about 15 to about 25 mM, or about 20 mM, and comprises trehalose at about 1% to about 15%, or about 5% to about 12%, or about 10% or 9.5%, and comprises proline at about 10 mM to about 40 mM, or about 15 to about 30 mM, or about 20 mM.

In some embodiments, the formulation comprises a histidine buffer at about 1 to about 50 mM, or about 10 to about 30 mM, or about 15 to about 25 mM, or about 20 mM, and comprises trehalose at about 5% to about 15%, or about 8% to about 12%, or about 10% or 9.5%, and comprises glycine at about 10 mM to about 40 mM, or about 15 to about 30 mM, or about 20 mM.

In some embodiments, the formulation comprises a histidine buffer at about 1 to about 50 mM, or about 10 to about 30 mM, or about 15 to about 25 mM, or about 20 mM, and comprises sucrose at about 1% to about 15%, or about 5% to about 12%, or about 10% or 9.5%.

In some embodiments, the formulation comprises a histidine buffer at about 1 to about 50 mM, or about 10 to about 30 mM, or about 15 to about 25 mM, or about 20 mM, and comprises sucrose at about 1% to about 10%, about 4% to about 6%, or about 5% or 4.5%, and comprises trehalose at about 1% to about 10%, about 4% to about 6%, or about 5% or 4.5%.

In particular embodiments, the formulation comprises a histidine buffer at about 1 to about 50 mM, or about 10 to about 30 mM, or about 15 to about 25 mM, or about 20 mM, and comprises trehalose at about 5% to about 15%, or about 8% to about 12%, or about 10% or 9.5%, and comprises EDTA at about 0.01% to about 0.1%, or about 0.02% to about 0.08%, or about 0.05%.

Certain formulations comprise a histidine buffer at about 1 to about 30 mM, or about 5 to about 20 mM, or about 10 mM, and comprise glycine at about 1% to about 5%, or about 2% or 1.9%, comprise trehalose at about 0.1% to about 2%, or about 0.5% to about 1.5%, or about 1%, and comprise a surfactant, for example, P20, at about 0.001% to about 0.1%, or about 0.005% to about 0.02%, or about 0.01%. Some formulations comprise a histidine buffer at about 1 to about 30 mM, or about 5 to about 20 mM, or about 10 mM, and comprise sucrose at about 1% to about 15%, or about 5% to about 12%, or about 10% or 8.5%, and comprise trehalose at about 0.1% to about 2%, or about 0.5% to about 1.5%, or about 1%. Particular formulations comprise a histidine buffer at about 1 to about 30 mM, or about 5 to about 20 mM, or about 10 mM, and comprise sucrose at about 1% to about 15%, or about 5% to about 12%, or about 10% or 9%. Some formulations comprise a histidine buffer at about 1 to about 50 mM, or about 10 to about 40 mM, or about 20, 25, 30, or 35 mM, and comprise a sodium chloride at about 100 to about 150 mM, or about 120, 130, or 140 mM. Certain formulations comprise a sodium phosphate buffer at about 100 to about 200 mM, or about 150 mM, and comprise sucrose and/or trehalose at about 1% to about 10%, about 4% to about 6%, or about 5% or 4.5%, and comprise glycine at about 0.1 to about 1%, or about 0.5%, and comprise glycerol at about 0.1 to about 1.0%, or about 0.25%, and comprise Tween 80 at about 0.001 to about 0.1%, or about 0.01%, and comprise EDTA at about 0.01 to about 0.1%, or about 0.05%.

In some embodiments, the pharmaceutically-acceptable pH of the formulation is about 5.0 to about 8.0 (±0.01 to ±0.1 or to ±1.0), or about 5.0, 5.1, 5.2, 5.3, 5.4, 5.5, 5.6, 5.7, 5.8, 5.9, 6.0, 6.1. 6.2. 6.3. 6.4. 6.5. 6.6. 6.7. 6.8. 6.9. 7.0, 7.1, 7.2, 7.3, 7.4, 7.5, 7.6, 7.7, 7.8, 7.9, or 8.0 (±0.01 to ±0.1), including all integers and ranges in between. In specific embodiments, the formulation comprising ADI-PEG has a pH of about 6.8 (±1.0). In particular embodiments, the pH is about 6.5 to about 7.2 (±0.1), or about 6.6 to about 7.0 (±0.1), or about 6.8 (±0.1). In some embodiments, the pH is about 6.0 to about 7.2 (±0.1), or at about 6.4 to about 6.8 (±0.1), or about 6.5 (±0.1).

As noted above, the formulations described herein comprise one or more pegylated arginine deiminase (ADI-PEG) molecules, or arginine deiminase (ADI) polypeptides that are modified by covalent attachment to one or more polyethylene glycol (PEG) molecules. When compared to unmodified ADI, ADI-PEG retains most of its enzymatic activity, is less immunogenic or antigenic, has a greatly extended circulating half-life, and is more efficacious in the treatment of tumors.

In certain embodiments, the dry weight of the ADI-PEG in the lyophilized formulation is about 50 mg/g to about 150 mg/g, or about 50, 55, 60, 65, 70, 75, 80, 85, 90, 95, 100, 105, 110, 120, 125, 130, 135, 140, 145, or 150 mg/g, including all integers and ranges in between.

In certain embodiments, an ADI polypeptide or ADI-PEG molecule has an "ADI activity", or the ability to convert or metabolize arginine into citrulline and ammonia. ADI activity can be measured according to routine techniques in the art. For instance, the amount of L-citrulline can be detected by a colorimetric endpoint assay (see, for example, Knipp and Vasak, Analytical Biochem. 286:257-264, 2000) and compared to a standard curve of known amounts of L-citrulline in order to calculate the specific activity of ADI, which can be expressed as IU/mg of protein. In some embodiments, one IU of ADI enzyme activity is defined as the amount of enzyme that produces 1 μmol of citrulline per minute at the pH and temperature being tested.

The ADI portion of the ADI-PEG molecule(s) can be derived from a variety of sources. For example, in some embodiments, the ADI polypeptide is from *M. hominis, M. arginini, M. arthritidis, M. phocicerebrale, M. gateae, M. phocidae, M. columbinum, M. iowae, M. crocodyli, M. alligatoris, H. orenii*, or *M. bovis*. In some embodiments, the ADI polypeptide is from *Mycoplasma salivarium, Mycoplasma spumans, Mycoplasma canadense, Mycoplasma auris, Mycoplasma hyosynoviae, Mycoplasma cloacale, Mycoplasma anseris, Mycoplasma alkalescens, Mycoplasma orale, Mycoplasma finers, Mycoplasma meleagridis, Mycoplasma alvi, Mycoplasma penetrans, Mycoplasma gallinarum, Mycoplasma pirum, Mycoplasma primatum, Mycoplasma fermentans, Mycoplasma lipofaciens, Mycoplasma felifancium, Mycoplasma imitans, Mycoplasma opalescens, Mycoplasma moatsii, Mycoplasma elephantis, Mycoplasma pneumoniae, Mycoplasma testudinis, Mycoplasma* sp. CAG: 877, or *Mycoplasma* sp. CAG:472.

Illustrative ADI polypeptides are provided in Table A1 below.

TABLE A1

ADI Polypeptide Sequences

| Source | Sequence | SEQ ID NO: |
|---|---|---|
| Mycoplasma hominis | MSVFDSKFNGIHVYSEIGELETVLVHEPGREIDYITPARLDELLFSAILESHD ARKEHQSFVKIMKDRGINVVELTDLVAETYDLASKAAKEEFIETFLEETVPVL TEANKKAVRAFLLSKPTHEMVEFMMSGITKYELGVESENELIVDPMPNLYFTR DPFASVGNGVTIHFMRYIVRRRETLFARFVFRNHPKLVKTPWYYDPAMKMPIE GGDVFIYNNETLVVGVSERTDLDTITLLAKNIKANKEVEFKRIVAINVPKWTN LMHLDTWLTMLDKNKFLYSPIANDVFKFWDYDLVNGGAEPQPQLNGLPLDKLL ASIINKEPVLIPIGGAGATEMEIARETNFDGTNYLAIKPGLVIGYDRNEKTNA ALKAAGITVLPFHGNQLSLGMGNARCMSMPLSRKDVKW | 1 |
| PHX8 | MSVFDSKFNGIHVYSEIGELETVLVHEPGREIDYITPARLDELLFSAILESHD ARKEHQSFVKIMKDRGINVVELTDLVAETYDLASKAAKEEFIETFLEETVPVL TEANKEAVRAFLLSKPTHEMVEFMMSGITKYELGVESENELIVDPMPNLYFTR DPFASVGNGVTIHFMRYIVRRRETLFARFVFRNHPKLVKTPWYYDPAMKMSIE GGDVFIYNNETLVVGVSERTDLDTITLLAKNIKANKEVEFKRIVAINVPKWTN LMHLDTWLTMLDKNKFLYSPIANDVFKFWDYDLVNGGAEPQPQLNGLPLDKLL ASIINKEPVLIPIGGAGATEMEIARETNFDGTNYLAIKPGLVIGYDRNEKTNA ALKAAGITVLPFHGNQLSLGMGNARCMSMPLSRKDVKW | 2 |
| Mycoplasma phocicerebrale | IHVYSEIGELETVLVHEPGREIDYITPARLDELLFSAILESHDARKEHQSFVK QLKDNGINVVELTDLVAETFDLASKEEQEKLIEEFLEDSEPVLSEAHKTAVRK FLTSRKSTREMVEFMMAGITKYDLGIEADHELIVDPMPNLYFTRDPFASVGNG VTIHYMRYKVRQRETLFSRFVFSNHPKLVKTPWYYDPAMKMSIEGGDVFIYNN DTLVVGVSERTDLETITLLAKNIKANKEVEFKRIVAINVPKWTNLMHLDTWLT MLDKDKFLYSPIANDVFKFWDYDLVNGGAEPQPKENGLPLEGLLQSIINKKPV LIPIAGNNASHIDIERETHFDGTNYLAIKPGVVIGYARNEKTNAALAAAGIKV LPFHGNQLSLGMGNARCMSMP | 3 |
| Mycoplasma arginini | MSVFDSKFKGIHVYSEIGELESVLVHEPGREIDYITPARLDELLFSAILESHD ARKEHKQFVAELKANDINVVELIDLVAETYDLASQEAKDKLIEEFLEDSEPVL SEEHKVVVRNFLKAKKTSRELVEIMMAGITKYDLGIEADHELIVDPMPNLYFT RDPFASVGNGVTIHYMRYKVRQRETLFSRFVFSNHPKLINTPWYYDPSLKLSI EGGDVFIYNNDTLVVGVSERTDLQTVTLLAKNIVANKECEFKRIVAINVPKWT | 4 |

TABLE A1-continued

ADI Polypeptide Sequences

| Source | Sequence | SEQ ID NO: |
|---|---|---|
| | NLMHLDTWLTMLDKDKFLYSPIANDVFKFWDYDLVNGGAEPQPVENGLPLEGL<br>LQSIINKKPVLIPIAGEGASQMEIERETHFDGTNYLAIRPGVVIGYSRNEKTN<br>AALEAAGIKVLPFHGNQLSLGMGNARCMSMPLSRKDVKW | |
| Mycoplasma arthritidis | MSVFDSKFKGIHVYSEIGELETVLVHEPGKEIDYITPARLDELLFSAILESHD<br>ARKEHKEFVAELKKRGINVVELVDLIVETYDLASKEAKEKLLEEFLDDSVPVL<br>SDEHRAAVKKFLQSQKSTRSLVEYMIAGITKHDLKIESDLELIVDPMPNLYFT<br>RDPFASVGNGVTIHYMRYKVRQRETLFSRFVFSNHPKLVNTPWYYDPAEGLSI<br>EGGDVFIYNNDTLVVGVSERTDLQTITLLAKNIKANKECEFKRIVAINVPKWT<br>NLMHLDTWLTMLDKDKFLYSPIANDVFKFWDYDLVNGGDAPQPVDNGLPLEDL<br>LKSIIGKKPTLIPIAGAGASQIDIERETHFDGTNYLAVAPGIVIGYARNEKTN<br>AALEAAGITVLPFRGNQLSLGMGNARCMSMPLSRKDVK | 5 |
| Mycoplasma orale | SVFSDKFNGIHVYSEIGDLESVLVHEPGKEIDYITPARLDELLFSAILESTDA<br>RKEHKEFVEILKKQGINVVELVDLIVETYNLVDKKTQEKLLEFLDDSEPVLS<br>PEHRKAVEKFLKSLKSTKELIQYMMAGITKYDLGIKADKELIVDPMPNLYFTR<br>DPFASVGNGVTIHYMRYKVRQRETLFSKFIFTNHPKLVKTPXYYDPAMKLSIE<br>GGDVFIYNNDTLVVGVSERTDLETITLLAKNIKANKECEFKRIVAINVPKXTN<br>LMHLDTXLTMLDKDKFLYSPIANDVFKFXDYDLVNGGSNPEPVVNGLPLDKLL<br>ESIINKKPVLIPIAGKGATEIETAVETHFDGTNYLAIKPGVVVGYSRNVKTNA<br>ALEANGIKVLPFKGNQLSLGMGNARCMSMPLSRKDVK | 6 |
| Mycoplasma gateae | IHVYSEIGELESVLVHEPGREIDYITPARLDELLFSAILESHDARKEHKLFVS<br>ELKANDINVVELTDLVTETYDLASQEAKDNLIEEFLEDSEPVLTEELKSVVRT<br>YLKSIKSTRELIQMMAGITKYDLGIEADHELIVDPMPNLYFTRDPFASVGNG<br>VTIHYMRYKVRQRETLFSRFVFSNHPKLVNTPWYYDPSLKLSIEGGDVFIYNN<br>NTLVVGVSERTDLETVTLLAKNIVANKECEFKRIVAINVPKWTNLMHLDTWLT<br>MLDKDKFLYSPIANDVFKFWDYDLVNGGEEPQPVENGLPLEGLLESIINKKPI<br>LIPIAGEGASQIDIERETHFDGTNYLAIRPGVVIGYSRNEKTNAALEAAGIKV<br>LPFHGNQLSLGMGNARCMSM | 7 |
| Mycoplasma phocidae | IHVYSEIGELQTVLVHEPGREIEYITPARLDELLFSAILESHDARKEHQEFVA<br>ELKKNNINVVELTDLVSETYDMVSKEKQEKLIEEFLEDSEPVLSEEHKGLVRK<br>FLKSLKSSKELIQYMMAGITKHDLNIEADHELIVDPMPNLYFTRDPFASVGNG<br>VTIHYMRYKVRQRETLFSRFIFANHPKLMNTPLYYNPDMKLSIEGGDVFYNN<br>ETLVVGVSERTDLDTITLLAKNIKANKEREFKRIVAINVPKWTNLMHLDTWLT<br>MLDKDKFLYSPIANDVFKFWDYDLVNGGDEPQPKVNGLPLEKLLESIINKKPI<br>LIPIAGTSASNIDVERETHFDGTNYLAIAPGVVIGYSRNVKTNEALEAAGIKV<br>LPFKGNQLSLGMGNARCMSMP | 8 |
| Mycoplasma columbinum | MSKINVYSEIGELKEVLVHTPGDEIRRISPSRLDELLFSAILEPNEAIKEHKG<br>FLKILQDKGIKVIQLSDLVAETYTYHATQKEREAFIEKWLDEAEPALTKDLRA<br>KVKSYVLSKEGTPVAMVRTMMAGVSKQELNVESETELVVDPMPNLYFTRDPFA<br>SAGNGISLNNMKYVTRKRETIFAEFIFATHPDYKTTPHWFDRLDEGNIEGGDV<br>FIYNKDTLVIGVSERTNKEAILTIAKKIKNNKEAKFKKIVAINVPPMPNLMHL<br>DTWLTMVDKDKFLYSPNMLSVLKVWEIDLSKEIEMVETNKPLADVLESIIGVK<br>PVLIPIAGKGATQLDIDIETHFDGTNYLTIAPGVVVGYSRNIKTEAALRAAGV<br>TVLSFEGNQLSLGMGSARCMSMPLVREDVK | 9 |
| Mycoplasma iowae | MGNNIPKKINVFSEIGNLKRVLVHTPGKEIEYVTPQRLDELLFSAILDPVRAR<br>EEHKEFIKILESQGVEVVQLVDLTAETYDVAESQAKENFIQKWLDESLPKLTD<br>ENRNKVYSLLKSLEKDPKEMIRKMMSGVLASEIGVKSDVELIVDPMPNLYFTR<br>DPFASVGNGITLHRMFRPTRRRETIFADFIFSNHPEYKSTQKYYEREDKFSLE<br>GGDVFIYNNKTLVVGVSERTEKGAIKALAKAVQNNSNMSFEKIYAINVPKMSN<br>LMHLDTWLTMLDTDKFLYSPNMMGVLKIWEIDLSDKSLWKEIRDSLDHFLST<br>IIGKKAITVPVAGKDAMQFEIDIETHFDATNFIAVAPGVVIGYDRNKKTNEAL<br>KEAGIKVLSWNGDQLSLGMGSARCMTMPLYREELKK | 10 |
| Mycoplasma crocodyli | MNKINVYSEVGKLKEVLVHTPGDEIRRISPSRLEELLFSAILEPDSAIEEHKR<br>FLKILEDNNIKVIQLDQLVADTYELVNPSVRDAFIEKWLNESEPKLDKKLREK<br>VKEYLLHTQKTVGTKRMVRIMMAGVDRVELGVELDRQLVVDPMPNLYFTRDPF<br>ASAGNGISLNNMKYVTRKRETIFSEFIFENHPDYKTTPHWFDRLDKGNIEGGD<br>VFIYNRTTLVIGISERTNKDALLTIANNIKSNKESKFERIVAVNVPPMPNLMH<br>LDTWLTMVDHDKFLYSPNMMKTLKFWTIDLTKPIKMVELEESLSDMIETIIGK<br>KPVLIPIAGHDASPLDVDIETHFDGTNYLTIAPGVVVGYSRNKLTEKALTKAG<br>VKVLSFEGNQLSLGMGSARCMSMPLVREDIK | 11 |
| Mycoplasma fermentans | MQIIAKIDLLTNMLIFMKIYFIGRLIMKKINVYSEYGKLKEVLVHTPGDEIRR<br>LAPSRLDELLFSAILEPDSAIAEHKRFVQLLKDNGIKVIQLDELFAKTFDLVS<br>ESVKQSLIERWLDECEPKLDATLRAKVKEYILELKAKSSKKMVRVMMAGIDKK<br>ELGIELDRDLVVDPMPNLYFTRDPFASVGNGISLHHMKYVTRQRETIFSEFIF<br>DNNLDYNTVPRWFDRKDEGRIEGGDVFIYSADTLVVGVSERTNKEAINVMARK<br>IAADKEVKFKRIYAINVPPMPNLMHLDTWLTMLDKNKFLYSPNMLSVLKVWRI | 12 |

TABLE A1-continued

ADI Polypeptide Sequences

| Source | Sequence | SEQ ID NO: |
|---|---|---|
| | DLNDPDFVWHEIEGSLEEILEQIIGMKPILIPIAGKGASQLDIDIETHFDGTN YLTIAPSVVVGYSRNEKTEKALKAAKVKVLSFEGNQLSLGMGSARCMSMPLIR EDIKKK | |
| Mycoplasma penetrans | MVITIALNILNKIYFKPQNRSILKLYRLPSLCTQISIFIGGKMSSIDKNSLGN GINVYSEIGELKEVLVHTPGDEIRYTAPSRLEELLFSAVLKADTAIEEHKGFV KILQNNGIKVIQLCDLVAETYELCSKEVRNSFIEQYLDEALPVLKKEIRPVVK DYLLSFPTVQMVRKMMSGILANELNIKQDNPLIIDGMPNLYFTRDPFASMGNG VSINCMKYPTRKREVIFSRFVFTNNPKYKNTPRYFDIVGNNGTIEGGDIFIYN SKTLVIGNSERTNFAAIESVAKNIQANKDCTFERIVVINVPPMPNLMHLDTWL TMLDYDKFLYSPNMMNVLKIWEIDLNVKPVKFVEKKGTLEEVLYSIIDKKPIL IPIAGKGANQLDIDIETHFDGTNYLTIAPGVVVGYERNEKTQKALVEAGIKVL SFNGSQLSLGMGSARCMSMPLIRENLKK | 13 |
| Mycoplasma gallisepticum | MFNKIRVYSEIGKLRKVLVHTPGKELDYVTPQRLDELLFSSLLNPIKARQEHE TFIKLLEDHDVECVQLSTLTAQTFQAMNSKIQEEFINRWLDECLPVLSEINRL KVYDYLKSLATNPQVMIRKMMSGILAKEVGIQSEVELVADPMPNLYFTRDPFA SIGKGITLHSMFHPTRKRETIFADFIFSHHPEYKNAPKYYSREDKYSIEGGDL FVYDDKTLVIGVSERTEKKAIQSLAEKLRQNDETSFEKIYAINVPKMSNLMHL DTWLTMLDYDKFLYSPNMMGVLKIWEIDLIHPTLIWRELNESLEGFLSMVIGK KATLIPVAGEDSTQIEIDVETNFDATNFLVIQPGVVVGYDRNYKTNQALRDAG VKVISWNGDQLSLGMGSARCMSMPLYRDPIKK | 14 |
| Mycoplasma alligatoris | MSKINVYSEVGRLKEVLVHTPGDEIRRISPTRLEELLFSAILEPDTAIEEHKR FLNVLEKNGIKAIQLDELVAQTYDQVDQKIKDEFIDQWLQEAKPVLNDQLKKL VKNYLLKSQKEFSTKKMVRIMMAGIDKKEINIDLDRDLVVDPMPNLYFTRDPF ASVGNGISLHNMKYQTRKRETIFAQFIFKYNKDYKTTPHWFDRFDHGSIEGGD VFVYTKDTLVIGISERTTKEAVLNIAKKIKANTDSKFKKIVAINVPPMPNLMH LDTWITMVDHDKFLYSPNMMKSLKFWLIDLSKEIKMVELEESLSNMLEAIIGK KPILIPIAGKNASQLDIDIETHFDGTNYLTIAPGVVVGYSRNKLTQKALEDAG VKVLSFDGNQLSLGMGSARCMSMPLVREDIK | 15 |
| Mycoplasma pneumoniae | MSKKQLVKTDGHNQLDQPNTKALQLKKKQFNSGVRVTSEISFLREVIAHHPGI ETERVIDNQTFGSAMYLERAQKEHQLFIKILRQHGTKVHYLQDLLLEALSAAD PNVRQDFIKNFLLESGIKSVSTFEACLNFFRSLDSLVDVIKVMFGGIKVSDVP PITPQRFADIHVSNSPFLIKPLSFSLYPHKFFNTLGTGVALFVTNDSELKRHS LVYEYIMRFHPRFDGVKLYTNRDFKNCLINSSDIIQISNEILLIGISHDTDVL GIESLARNLLSDHTNPIKQIIAINIHKFGAKTNLNKLIAMVDVDKFIIARKVL QATEIFELTATAQRDVDGLAQIKFKPLKFNFGEIIEAIIDKQPRFVIIGGGDE VAERKELLDCGMGVLNLSPGEIVVFDRNHYTNNLLNELGLIIHKIPASELSRG PSGPLEMVCSLWRE | 16 |
| Mycoplasma mobile | MKDTKDIINVFSEIGELKKVLIHTPGNELKYVSPYRLDELLFSNVLEWREAKK EHNEFIQKLKSEGVEPVELTDLVAESFEESSIKVKNDFIRQYLDEATPILDGL TKQKLLPFFLDIKHSTRKTIELMMSGITQKDISISHIERELIIDPMPNLYFSR DNFISIGNSVIISNMKYKTRKRETIFTDPFIFKNHPLYKKVNMAFERKDLNNQI SIIEGGDVLVYSKEILIIGISERTTMSAILELAENFKKTKRSFKKIYGVEVPK MKNLMHLDTWLTMIDYDKFIYSPNVLTDLKFWEINLDYEKISSKELHASLSEF LKLIIGKDPILIPIGGKGASQITIDIETNFVAANYLVIRPGVVIGYSRNYETQ KALEGHGVKVIAFEGNQLSLGMGSSRCMSMPLIRSNLK | 17 |
| Streptococcus pyogenes | MTAQTPIHVYSEIGKLKKVLLHRPGKEIENLMPDYLERLLFDDIPFLEDAQKE HDAFAQALRDEGIEVLYLETLAAESLVTPEIREAFIDEYLSEANIRGRATKKA IRELLMAIEDNQELIEKTMAGVQKSELPEIPASEKGLTDLVESNYPFAIDPMP NLYFTRDPFATIGTGVSLNHMFSETRNRETLYGKYIFTHHPIYGGGKVPMVYD RNETTRIEGGDELVLSKDVLAVGISQRTDAASIEKLLVNIFKQNLGFKKVLAF EFANNRKFMHLDTVFTMVDYDKFTIHPEIEGDLRVYSVTYDNEELHIVEEKGD LAELLAANLGVEKVDLIRCGGDNLVAAGREQWNDGSNTLTIAPGVVVVYNRNT ITNAILESKGLKLIKIHGSELVRGRGGPRCMSMPFEREDI | 18 |
| Enterococcus faecalis | MSHPINVFSEIGKLKTVMLHRPGKELENLMPDYLERLLFDDIPFLEKAQAEHD AFAELLRSKDIEVVYLEDLAAEALINEEVRRQFIDQFLEEANIRSESAKEKVR ELMLEIDDNEELIQKAIAGIQKQELPKYEQEFLTDMVEADYPPIIDPMPNLYF TRDNFATMGHGISLNHMYSVTRQRETIFGQYIFDYHPRFAGKEVPRVYDRSES TRIEGGDELILSKEVVAIGISQRTDAASIEKIARNIFEQKLGFKNILAFDIGE HRKFMHLDTVFTMIDYDKFTIHPEIEGGLVVYSITEKADGDIQITKEKDTLDN ILCKYLHLDNVQLIRCGAGNLTAAAREQWNDGSNLAIAPGEVVVYDRNTITN KALEEAGVKLNYIPGSELVRGRGGPRCMSMPLYREDL | 19 |
| Mycoplasma capricolum | MEKKINVFSEIGTLKTVLVHRPGDEIENLTPELLERLLFDDVPFKDVAVKEHD AFTKIMRDNGVEVLYIEKLAAETLDQHPDLREKFIDQFISEANIEDKYKEKYR DFISSLDNYRMIKKMIAGTKKLELGIDEGYKAYPFIADPLPNVLFQRDPFSSV GFGITMNRMWSVTRNRETIFPDLVFKHHNRFANQVPYYYERDWKEETIEGGDI LVLNKETLIIGVTQRRTTLKAIEKFSERLFNDPESSYSKVIALDLPKSRAFMHL | 20 |

TABLE A1-continued

ADI Polypeptide Sequences

| Source | Sequence | SEQ ID NO: |
|---|---|---|
| | DTVFTNIDYDKFIAHPLIFDCIDEFKIYEVSKQGTKEVKKTLIELLSDAAGRE VQIIRCGGNDVVGASREQWNDGTNVVALRPGKVIAYERNWITIDLLRKAGVEV LTIASSELSRGRGGPRCMTMPLWREDLQEIKR | |
| Halothermothrix orenii | MFKKSPLNVTSEIGKLKKVLLHRPGHEIENLTPDLLERLLFDDIPYLKVAQEE HDAFAQTLRDNGVEVLYLHELAAEAIQEDEIRKKFIEQFLDEAGVIGKGARQV LKEYFADMDNETLIRKMMAGVRKKEIPAIEKVASLNDMVEEDYPFVLDPMPNL YFTRDPFATIGTGITLNHMRTETRNREVIFAEYIFSYHPDFKDTEIPFWFDRN ETTSIEGGDELILSDKVLAMGISERTDAASIEKVARNIFTDGQPFETILAFKI PEKRAFMHLDTVFTMVDYDKFTIHAEIEGPLKVYSITKGDNDELKIDEEKATL EDTLKKYLGLDEVTLIRCAGGDYIDAGREQWNDGSNTLAIAPGEVVVYNRNHT TNRLLEEHGIKLHVIPSSELSRGRGGPRCMSMPLVREDI | 21 |
| Staphylococcus aureus | MTDGPIKVNSEIGALKTVLLKRPGKELENLVPDYLDGLLFDDIPYLEVAQKEH DHFAQVLREEGVEVLYLEKLAAESIENPQVRSEFIDDVLAESKKTILGHEEEI KALFATLSNQELVDKIMSGVRKEEINPKCTHLVEYMDDKYPFYLDPMPNLYFT RDPQASIGHGITINRMFWRARRRESIFIQYIVKHHPRFKDANIPIWLDRDCPF NIEGGDELVLSKDVLAIGVSERTSAQAIEKLARRIFENPQATFKKVVAIEIPT SRTFMHLDTVFTMIDYDKFTMHSAILKAEGNMMIFIIEYDDVNKDIAIKQSSH LKDTLEDVLGIDDIQFIPTGNGDVIDGAREQWNDGSNTLCIRPGVVVTYDRNY VSNDLLRQKGIKIVIEISGSELVRGRGGPRCMSQPLFREDI | 22 |
| Pseudomonas plecoglossicida | MSAEKQKYGVHSEAGKLRKVMVCAPGLAHKRLTPSNCDELLFDDVIWVDQAKR DHFDFVTKMRERGVDVLEMHNLLTDIVQNPEALKWILDRKITPDTVGVGLTNE VRSWLEGQEPRHLAEFLIGGVAGQDLPESEGASVVKMYNDYLGHSSFILPPLP NTQFTRDTTCWIYGGVTLNPMYWPARRQETLLTTAIYKFHPEFTKADFQVWYG DPDQEHGQATLEGGSVDMPIGKGIVLIGMGERTSRQAIGQLAQNLFAKGAVEQV IVAGLPKSRAAMHLDTVFSFCDRDLVTVFPEVVREIVPFIIRPDESKPYGMDV RRENKSFIEVVGEQLGVKLRVVETGGNSFAAEREQWDDGNNVVALEPGVVIGY DRNTYTNTLLRKAGIEVITISAGELGRGRGGGHCMTCPIVRDPINY | 23 |
| Pseudomonas putida | MSAEKQKYGVHSEAGKLRKVMVCAPGLAHKRLTPSNCDELLFDDVIWVDQAKR DHFDFVTKMRERGVDVLEMHNLLTDIVQNKDALKWILDRKITPDTVGVGLTNE VRSWLEGLEPRHLAEFLIGGVAGQDLPQSEGADVVKMYNDYLGHSSFILPPLP NTQFTRDTTCWIYGGVTLNPMYWPARRQETLLTTAIYKFHPQFTGADFQVWYG DPDKDHGNATLEGGDVMPIGKGIVLIGMGERTSRQAIGQLAQNLFAKGAVEKV IVAGLPKSRAAMHLDTVFSFCDRDLVTIFPEVVKEIVPFIIRPDESKPYGMDV RRENKSFIEVVGEQLGVKLRVVETGGNSFAAEREQWDDGNNVVAVEPGVVIGY DRNTYTNTLLRKAGIEVITISAGELGRGRGGGHCMTCPIVRDPIDY | 24 |
| Pseudomonas aeruginosa | MSTEKTKLGVHSEAGKLRKVMVCSPGLAHQRLTPSNCDELLFDDVIWVNQAKR DHFDFVTKMRERGIDVLEMHNLLTETIQNPEALKWILDRKITADSVGLGLTSE LRSWLESLEPRKLAEYLIGGVAADDLPASEGANILKMYREYLGHSSFLLPPLP NTQFTRDTTCWIYGGVTLNPMYWPARRQETLLTTAIYKFHPEFANAEFEIWYG DPDKDHGSSTLEGGDVMPIGNGVVLIGMGERSSRQAIGQVAQSLFAKGAAERV IVAGLPKSRAAMHLDTVFSFCDRDLVTVFPEVVKEIVPFSLRPDASSPYGMSI RREEKTFLEVVAESLGLKKLRVVETGGNSFAAEREQWDDGNNVVCLEPGVVVG YDRNTYTNTLLRKAGVEVITISASELGRGRGGGHCMTCPIIRDPIDY | 25 |
| Mycobacterium tuberculosis complex | MGVELGSNSEVGALRVVILHRPGAELRRLTPRNTDQLLFDGLPWVSRAQDEHD EFAELLASRGAEVLLLSDLLTEALHHSGAARMQGIAAAVDAPRLGLPLAQELS AYLRSLDPGRLAHVLTAGMTFNELPSDTRTDVSLVLRMHHGGDFVIEPLPNLV FTRDSSIWIGPRVVIPSLALRARVREASLTDLIYAHHPRFTGVRRAYESRTAP VEGGDVLLLAPGVVAVGVGERTTPAGAEALARSLFDDDLAHTVLAVPIAQQRA QMHLDTVCTMVDTDTMVMYANVVDTLEAFTIQRTPDGVTIGDAAPFAEAAAKA MGIDKLRVIHTGMDPVVAEREQWDDGNNTLALAPGVVVAYERNVQTNARLQDA GIEVLTIAGSELGTGRGGPRCMSCPAARDPL | 26 |
| Mycoplasma arthritidis | MSVFDSKFKGIHVYSEIGELETVLVHEPGKEIDYITPARLDELLFSAILESHD ARKEHKEFVAELKKRGINVVELVDLIVETYDLASKEAKEKLLEEFLDDSVPVL SDEHRAAVKKFLQSQKSTRSLVEYMIAGITKHDLKIESDLELIVDPMPNLYFT RDPFASVGNGVTIHYMRYKVRQRETLFSRFVFSNHPKLVNTPWYYDPAEGLSI EGGDVFIYNNDTLVVGVSERTDLQTITLLAKNIKANKECEFKRIVAINVPKWT NLMHLDTWLTMLDKDKFLYSPIANDVFKFWDYDLVNGGDAPQPVDNGLPLEDL LKSIIGKKPTLIPIAGAGASQIDIERETHFDGTNYLAVAPGIVIGYARNEKTN AALEAAGITVLPFRGNQLSLGMGNARCMSMPLSRKDVK | 27 |
| Mycoplasma phocicerebrale Artificial full length from new species patent. | MSVFDSKFNGIHVYSEIGELETVLVHEPGREIDYITPARLDELLFSAILESHD ARKEHQSFVKQLKDNGINVVELTDLVAETFDLASKEEQEKLIEEFLEDSEPVL SEAHKTAVRKFLTSRKSTREMVEPMMAGITKYDLGIEADHELIVDPMPNLYFT RDPFASVGNGVTIHYMRYKVRQRETLFSRFVFSNHPKLVKTPWYYDPAMKMSI EGGDVFIYNNDTLVVGVSERTDLETITLLAKNIKANKEVEFKRIVAINVPKWT NLMHLDTWLTMLDKDKFLYSPIANDVFKFWDYDLVNGGAEPQPKENGLPLEGL | 28 |

TABLE A1-continued

ADI Polypeptide Sequences

| Source | Sequence | SEQ ID NO: |
|---|---|---|
| | LQSIINKKPVLIPIAGNNASHIDIERETHFDGTNYLAIKPGVVIGYARNEKTN AALAAAGIKVLPFHGNQLSLGMGNARCMSMPLSRKDVKW | |
| Mycoplasma gateae Artificial full length from new species patent. | MSVFDSKFNGIHVYSEIGELESVLVHEPGREIDYITPARLDELLFSAILESHD ARKEHKLFVSELKANDINVVELTDLVTETYDLASQEAKDNLIEEFLEDSEPVL TEELKSVVRTYLKSIKSTRELIQMMMAGITKYDLGIEADHELIVDPMPNLYFT RDPFASVGNGVTIHYMRYKVRQRETLFSRFVFSNHPKLVNTPWYYDPSLKLSI EGGDVFIYNNNTLVVGVSERTDLETVTLLAKNIVANKECEFKRIVAINVPKWT NLMHLDTWLTMLDKDKFLYSPIANDVFKFWDYDLVNGGEEPQPVENGLPLEGL LESIINKKPILIPIAGEGASQIDIERETHFDGTNYLAIRPGVVIGYSRNEKTN AALEAAGIKVLPFHGNQLSLGMGNARCMSMPLSRKDVKW | 29 |
| Mycoplasma phocidae Artificial full length from new species patent. | MSVFDSKFNGIHVYSEIGELQTVLVHEPGREIEYITPARLDELLFSAILESHD ARKEHQEFVAELKKNNINVVELTDLVSETYDMVSKEKQEKLIEEFLEDSEPVL SEEHKGLVRKFLKSLKSSKELIQMMMAGITKHDLNIEADHELIVDPMPNLYFT RDPFASVGNGVTIHYMRYKVRQRETLFSRFIFANHPKLMNTPLYYNPDMKLSI EGGDVFVYNNETLVVGVSERTDLDTITLLAKNIKANKEREFKRIVAINVPKWT NLMHLDTWLTMLDKDKFLYSPIANDVFKFWDYDLVNGGDEPQPKVNGLPLEKL LESIINKKPILIPIAGTSASNIDVERETHFDGTNYLAIAPGVVIGYSRNVKTN EALEAAGIKVLPFKGNQLSLGMGNARCMSMPLSRKDVKW | 30 |
| Mycoplasma salivarium | MSVFSSKFNGIHVYSEIGELETVLVHEPGKEIDYITPSRLDELLFSAILESHD ARKEHQEFVATLKKEKINVVELTDLVTETYDLVDQKTKDKLIEEFLEDSEPVL TAELKATVKKFLKSFKETRKLIEVMMAGITKYDLGIKADRELIVDPMPNLYFT RDPFASVGNGVTIHYMRYKVRQRETLFSRFIFNNHPKLVKTPWYYDPAMKMSI EGGDVFIYNNDTLVVGVSERTDLDTITLLAKNIKANKECEFKRIVAINVPKWT NLMHLDTWLTMLDKDKFLYSPIANDIFKFWDYDLVNGGANPQPKDNGLPLDKL LKSIIGKEPVLIPIAGHHATEIEVARETHFDGTNYLAIRPGVVIGYARNEKTN EALKDAGITVLPFKGNQLSLGMGNARCMSMPLSRKDVKW | 31 |
| Mycoplasma spumans | MSVFDSKFKGIHVYSEIGELESVLVHEPGREIDYITPARLDELLFSAILESHD ARKEHKGFVAELKKQNVNVIELTDLVAETYELASKEAQAKLIEDFIEDSEPVL NAEEAQAVRKFLSERKSTREMVEYMMSGLTKYELGLESADRELIVDPMPNLYF TRDPFASVGNGVTIHYMKYKVRQRETLFAKFVFSNHPKLVNTPRYYDPSMKLP IEGGDVFIYNNETLVVGCSERTELETITLLAKNIKANKEVEFKRIVAINVPKW TNLMHLDTWLTMLDKDKFLYSPIANDVFKFWDYDLVNGGEEPQPVENGLPLEE LLASIINKKPTLIPIAGEGATHIDVERETHFDGTNYLAIAPALIIGYSRNEKT NAALEKAGITVLPFHGNQLSLGMGNARCMSMPLSRKDVKW | 32 |
| Mycoplasma auris | MSVFDSKFKGIHVYSEIGELETVLVHEPGREIDYITPKRLDELLFSAILESHE ARKEHQFVAELKANDINVVELTDLVAETYDLVSQELKDKLIEEFLDDSYPVL TEEHKKAVRSFLKSRSSTRELIEYMMAGITKYDLGIEAEGDLIVDPMPNLYFT RDPFASVGNGVTIHYMRYKVRQRETLFSRFIFDNHPKLVNTPRYYDPSLKLSI EGGDVFIYNNDTLVMGVSERTDLETVTLLAKNIVANKECEFKRIVAINVPHWT NLMHLDTWLTMLDKDKFLYSPIANDYFKFWDYDLVNGGAEPQPVVNELPLDKL LESIIHKKPILIPIAGEGASQIDLERETHFDGTNYLVLRPGVVVGYARNEKTN AALEAVGIKVLPFYGNQLSLGMGNSRCMSMPLSRKDVKW | 33 |
| Mycoplasma hyosynoviae | MSVFNSKFKGIHVYSEIGDLESVLVHEPGKEIDYITPSRLDELLFSAILESND ARKEHKEFVEILKKEGVNVVELVDLIAETIDLVDAKKKEALIDEYIEDSEPVV DAKVKPLVKKLLLGIKDTKELVKLMMAGITKYDLEIESEKELIIDPMPNLYFT RDPFASVGNGVTIHYMRYKVRQRETLFSRFVFRNHPKLTSTPWYYDPAMKLSI EGGDVFIYNNDTLVVGVSERTDLDTITLLAKNIKANKECEFKRIVAINVPKWT NLMHLDTWLTMLDKDKFLYSPIANDIFKFWDYDLVNGGSEPQPKDNGLPLEKL LESIIGKKPVLIPIAGCCASDIEIARETHFDGTNYLAIKPGVVIGYARNEKTN KALEKAGIKVLPFKGNQLSLGMGNARCMSMPLSRKDVKW | 34 |
| Mycoplasma cloacale | MSVFDKRFKGIHVYSEIGELQTVLVHEPGREIDYITPARLDELLFSAILESHD ARKEHKEFVKILESQGINVVELTDLIAETYELASEEAKDNLIEEFLDESEPVL SEEHRILVRNFLKGITKTKELVKMMMAGITKYDLGIEADRELIVDPMPNLYFT RDPFASVGNGVTIHYMRYKVRQRETLFSRFIFENHPKLVSTPIYYHPSQGLSI EGGDVFIYNNDTLVVGVSERTDLQTITLLAKNIKANEECEFKRIVAINVPKWT NLMHLDTWLTMLDKNKFLYSPIANDVFKFWDYDLVNGGDEPQPVDNGLPLNEL LASIIGEEPVLVPIAGEGASKMDIERETHFDGTNYLAIAPGVVVGYSRNEKTN AALEKAGIKVLPFKGHQLSLGMGNARCMSMPLYRKDVK | 35 |
| Mycoplasma alkalescens | MSVFDSKFKGIHVYSEIGELESVLVHEPGHEIDYITPSRLDELLFSAMLESHD ARKEHQFVAELKANNVNVIELTDLVAETYDLASQEAKDKLIEEFLEDSEPVL SEENKIAVRDFLKSRKTTRELIEVMMAGITKYDLGIKNCKCQDLVVDPMPNLY FTRDPFASVGNGITIHYMRYKVRQRETLFSRFIFANHPKLVNTPIYYHPSLKL SIEGGDVFIYNNDTLVVGVSERTDLETITLLAKNIVANKECEFKRIVAINVPK WTNLMHLDTWLTMLDKDKFLYSPIANDVFKFWDYDLVNGGAEPKPVENGSSLE AILESIIHKKPILIPIGGDSASQIEVERETHFDGTNYLAIRPGVVIGYSRNVK TNAALEAAGIKVIPFHGNQLSLGMGNARCMSMPLSRKDVKW | 36 |

TABLE A1-continued

ADI Polypeptide Sequences

| Source | Sequence | SEQ ID NO: |
|---|---|---|
| Mycoplasma iners | MSKINVYSEIGVLKEVLVHTPGDEIRRIAPSRLDELLFSAILEPSAAIQEHKS FLKILQDRGIKTIQLSDLVAETYKHYASEAEKEAFIEKYLDEATPVLSKDMRA KVKNYILSMQGEPVKMVRTMMAGVSKQELNVESEVELIVDPMPNLYFTRDPFA SAGNGISLNNMKYVVRKRETIFAEFIFSIHPEYKKTPHWFDRLDNGSIEGGDV FIYNKDTLVIGVSERTNKEAIITIAKHIQDNKEAQFKKIVAINVPPMPNLMHL DTWLTMVDKNKFLYSPNMLSVLKVWEIDLSKPIEMVETNKPLAEVLESIIGEK PILIPIAGKDATQLDIDIETHFDGTNYLTIAPGVVVGYSRNVKTEAALRAAGV TVLSFEGNQLSLGMGSARCMSMPLVREDVK | 37 |
| Mycoplasma gallinarum | MSKIRVYSEIGNLKKVLVHTPGDEIRRISPSRLEELLFSAVLEPNAAIEEHKR EVKLLEDRGIQAIQLSDLVAETYVKYATAEQKAAFIEKYLDEATPALSAENRE RAKKYILSLEMQPVKMIRTMMAGLSKYELNVESNIELIIDPMPNLYFTRDPFA SAGNGISLNNMKYVVRKRETIFAEFIFAIHPEYKETPHWFDRLDHGSIEGGDV FVYNKDTLVIGVSERTNKEAIITIAKHIQDNKEAEFKKIVAINVPPMPNLMHL DTWLTMVDKNKFIYSPNMLSVLKIWEIDLAKPIEMVESNKSLTEVLESIIGEK PILIPIAGEGASQLDIDIETHFDGTNYLTIAPGVVVGYSRNEKTEKALKAAGI TVLSFEGNQLSLGMGSARCMSMPLVREDVK | 38 |
| Mycoplasma pirum | MNSNQKGIHVYSEIGKLKEVLVHRPGRELDFLDPTRLDELLFAATLEAETARL EHDNFTNALKNQGVTVIELADLVAQTYSSSTPTIKAAFINKYLDEATPALTTK LRTLVKDFLTKQKSVRKMVDYMIGGILSTDLNIKGKPELIVEPMPNAYFTHDP FASVGNGVTLHYMKHNVRRREVLFSEFIFNNNERFQNTPRYIVPTKGLDIEGG DVFVYNKNTLVVGVSERTKMVTIKELAKNILKNKECLFKKIYAINVPKMPNLM HLDTWLTMLDHNKFLYSPNMLSVLKIWEIDISSGKSISSPKELNMDLSKALSI IIGKKPILIPVAGENASQIDINIETNFDATNYLVTQPGVVVGYSRNKKTEAAL IKAGIEVIPFQGNQLSLGMGSARCMSMPLIREDV | 39 |
| Mycoplasma primatum | MSKSKINVYSEYGNLKEVLVHTPGDEIRRITPSRLDELLFSAILEPKSAIAEH KSFCQILKDNKVKAIQLDELVAATYKGVSESVQNSFVERWLDECEPKLENNVR PIVKEYLLKAAEQSVKKMIRIMMAGIDKREIGVESEVDPIVDPMPNLYFTRDP FASVGNGITLHHMKYVVRQRETLFSEFIFDNHPDYKFVPRYFDRDDEGKIEGG DVFIYNSKTLVVGISERTNKDAIRIVAKKIQANADAKFEKIFAINVPPMPNLM HLDTWLTMLDSNKFLYSPNMLSVLKVWEINLDDPALEWKEISGSLEEILTYII GKKPILIPIAGKGASQFEIDIETHFDGTNYLAIAPSVVIGYSRNELTEKALKK AGVKVLSLDGNQLSLGMGSARCMSMPLIREDVK | 40 |
| Mycoplasma lipofaciens | MSKINVYSEVGVLKEVLVHTPGDEIRRVAPSRLDELLFSAILEPQDAIAEHKR FIKILEDNNIKVIQLDELVSETWEKATAEQRDAFIEKWLDEAEPVLDAKLRET VKKYLLSLNPVKKMVRTMMAGIDKKELKIELDRDLVVDPMPNLYFTRDPFASA GNGISLNNMKYVTRKRETIFAEFIFNIHPDYKTTPHWFDRLDKGNIEGGDVFI YNKDTLVLGVSERTNKDAVMTIAKHIQSNEQAKFKKLVAINVPPMPNLMHLDT WLTMVDHDKFLYSPNMLSVLKIWEIDLTPGKEIEMVESTKSLSDMLESIIGKK PVLIPIAGKDASQLDIDIETHFDGTNYLTIRPGVVVGYSRNCLTEQALKDAGV TVLSFDGNQLSLGMGSARCMSMPLVREDIK | 41 |
| Mycoplasma felifaucium | MNKINVYSEIGKLKEVLVHTPGNEIRRISPSRLDELLFSALLEPNFAAKEHTA FCEILKENGIKAIQLVDLVSDTWRIASEKAKTEFIERWLDECEPKLDSNLREI VRKHIYAIEKRSVKRMVKTMMAGIERRELPVTSKEVARELVVDPMPNLYFTRD PFASVGNGISLHHMKYVTRQRETIFAEFVFGNHPDYIDTPRWFDRSDDGRIEG GDVFIYGSKTLVIGVSERTNKEAIKVMAKKIQANKEATFEKIYAINVPPMPNL MHLDTWLTMLDKNKFLYSPNMLAVLQVWEIDLKDPELTWHELSGSLEEILHKI IGRKPILIPIAGHGAQQIDIDIETHFDGTNYLAIAPGVVVGYNRNVLTERALK KAGIKVLSFEGNQLSLGMGSARCMSMPLIRENLK | 42 |
| Mycoplasma imitans | MFNKIKVYSEIGRLRKVLVHTPGKELEYVTPQRLDELLFSSLLNPVKARQEHE AFIKILQDQGVECVQLTTLTAQTFQSATSEVKEKFINRWLDECLPKLSDDNRI KVYAYLKDLSSDPEVMIRKMMSGILAKEVNVQSDVELIADPMPNLYFTRDPFA SIGKGVTLHSMFHPTRKRETIFADFVFSHHPEYKQTPKYYSRLNEYSIEGGDL FVYDDKTLVIGVSERTEKKAIQFLAEKLRENYETTFEKIYAINVPKMSNLMHL DTWLTMLDYDKFLYSPNMMGVLKIWEIDLTHEQLSWRELNESLEEFLSMVIGK KATTIPVAGEDSTQIEIDVETNFDATNFLVIQPGVVVGYDRNYKTNQALVNAG IKVLSWNGDQLSLGMGSARCMSMPLYRDPIKKG | 43 |
| Mycoplasma opalescens | MSKINVYSEIGTLKEVLVHTPGDEIRRVAPARLDELLFSAILEPNHAIAEHKA FIKILEDNGIKVIQLDELVVQTWNQVDEATRKAFVTKWLDECEPKLESNVRVE VEKYIYSLAKEPKKMVRTMMAGISKEELPLNVNRPLVVDPMPNLYFTRDPFAS VGTGISLHHMKYVTRQRETIFAQFVFDNHKDYNTVPRWFDNKDQGRIEGGDVF IYNTKTLVIGVSERTDKDAIKIMAKKIQADKNCKFEKIFAINVPPMPNLMHLD TWLTMVDRNKFLYSPNMLSVLKVWEIDLKDASLAWKEIEGSLSQILEKIIGEK PILIPIAGENASQLDIDIETHFDGTNYLTIAPGVVVGYSRNVKTEQALKAAGV KVLSFEGNQLSLGMGSARCMSMPLIREDLK | 44 |

TABLE A1-continued

ADI Polypeptide Sequences

| Source | Sequence | SEQ ID NO: |
|---|---|---|
| Mycoplasma moatsii | MKKNAINVYSEIGKLKKVLVHRPGDELKYVTPQRMDELLMSAIIELEQAKEEH DAFTKILRDNGVEVIELADLTAEMYDSLTPSEKDAFLNQWVKEASWGKKSSID ALKIKKNLSKKVFDYVKSIKPTRKMIDKLMAGVLLSEIGEKSIILNKDKKNEM VIDLVVDPMPNLYFTRDPPFASVGNGITLHNMKYPTRKRETIFAQWIFNKHPEY KDVPQFISKRDGKETIEGGDVFIYTKDVLAIGVSERTNMEAILRIATNIKKDK NCEFKKIVAINVPPMGNLMHLDTWLTMLDKDLFLYSGNIKSALKVWEIDLTKP ITPKSPKLSTAKLADILAKIVGKKVRMIPIGGKDGNQMDIDIETHFDGTNYLA IAPGVVVGYHRNRKTQKALEEAGVKVLAFQGNQLSLGMGSARCMSMPLVREEV K | 45 |
| Mycoplasma elephantis | MSQINVFSEIGQLKEVLVHTPGDEIRRISPKRYNELLFSAILEADVAIKEHKS FVKILEENNVKVIQLKDILLETWNICSKEAKNIFINKWIEEAQPVIHSSSLKE KIKLFLKSKTPLEIIDIMMKGILKQELGIEYKHELIIDPMPNLYFTRDPFTSM GSGITINNMKYQTRKRETIFSEFIFNNHPKYKNTPRWFDRFDSGNIEGGDLFV YTKETIVVGVSERTKKKAILKIAKNIQENNNSFKKIVVIKVPIMQNLMHLDTW IVMVDFDKFIYSPNVTKSLKFWEIDLTKKPKFIQLKNETLEDVLYRVIGKKPI LIPVAGENANQIDIDVETHFDATNYLTIRPGVVVGYSRNKKTEEALINAGVKV YAFEGNQLSLGMGSARCMSMPLIREDII | 46 |
| Mycoplasma testudinis | MKNINVYSEVGKLKEVVVHTPGEELHNVAPSRLQELLTSAVLEPEVARKEHLK FIKILNDYGKVIQIVDLITETYEAVDSNKKEAFINNWLDNSVPKLTDKNRMI LRNYLTQFSTKAMIRKMISGIRAKELNLKTPSALLVDPMPNLCFARDTFACVG SAISLSTMKHPTRREALLTEFIFQNHPKYKDVIKYFDSKNSKATIEGGDIFV YNPKTLVVGNSERTNMQACLLLAKKIQSNPNNKFEKIVIVNVPPLPHLMHLDT WLTMVDYDKFIYSPNILHTLKFWVIDLKKRKLEAVEKHNTLKAMLRMIIKKEP ILIPVGDVGADQLDIDLETHFDATNYLALAPGVVVGYDRNIKTQRALEKAGVK VLSFSGNQLSLAMGSARCLSMPLIREEN | 47 |
| Mycoplasma canadense | MSVFDSKFKGIHVYSEIGELESVLVHEPGREIDYITPARLDELLFSAILESHD ARKEHKQFVSELKANDINVVELTDLVAETYDLASQEAKDKLIEEFLEDSEPVL SEEHKAIVRKYLKGIQPTRKLIEMMMAGITKYDLGIEADHELIVDPMPNLYFT RDPFASVGNGVTIHYMRYKVRQRETLFSRFVFSNHPKLVNTPWYYDPSLKLSI EGGDVFVYNNDTLVVGVSERTDLQTVTLLAKNIVANKECEFKRIVAINVPKWT NLMHLDTWLTMLDKDKFLYSPIANDVFKFWYDLVNGGSEPQPVENGLPLEGL LESIINKKPILIPIAGEGASQMEIERETHFDGTNYLAIRPGVVIGYSRNEKTN AALEAAGIKVLPFHGNQLSLGMGNARCMSMPLSRKDVKW | 48 |
| Mycoplasma anseris | MSVFDKRFKGIHVYSEIGELQTVLVHEPGREIDYITPARLDELLFSAILESHD ARAEHKKFVATLKEQGINTVELTDLVAETYDLASQEARDNLLEEFLDDSAPVL SEEHKEIVRTYLKGIKGTRKLIETMMAGITKYDLGIEAEQELIVDPMPNLYFT RDPFASVGNGVTIHYMRYKVRQRETLFSRFIFSNHPQLVNTPWYYNPAEGLSI EGGDVFIYNNDTLVVGVSERTDLQTITLLAKNIKANEECEFKRIVAINVPKWT NLMHLDTWLTMLDTNKFLYSPIANDVFKFWYDLVNGGDEPQPVDNGLPLNEL LKSIIGEEPILIPIAGDGATQIEIERETHFDGTNYLAIAPGVVIGYSRNEKTN AALEAAGIKVLPFKGHQLSLGMGNARCMSMPLYRKDVK | 49 |
| Mycoplasma meleagridis | MSKINVYSEIGVLKEVLVHTPGDEIRRISPSRLDELLFSAILQPEQAIKEHQS FVKILQDRGIKVIQLSDLVAETYVKYATSKEKESFIEKWLDEATPALNSENRA RVKNYITAMQGQPVKMVRAMMAGVSKQELNIESDVELIVDPMPNLYFTRDPFA SAGNGISLNNMKYVVRKRETIFAEFIFSIHPEYKQTPHWFDRLDKGNIEGGDV FIYNKDTLVIGVSERTNKEAILTIAEHIKNNKEAKFKKIVAINVPPMPNLMHL DTWLTMVDKNKFLYSPNMLSVLKIWEIDLSKEIKMVETSKPLADVLESIIGEK PILIPIAGENASQLDIDIETHFDGTNYLTIAPGVVVGYSRNVKTEAALKAAGV TVYSFDGNQLSLGMGSGRCMSMPLVREDVK | 50 |
| Mycoplasma alvi | MSIKENGIHVYSEIGKLRDVLVHRPGRELNFLDPSRLDELLFAATLEPETARL EHDNFTTVLKNQGVNVIELADLVSQTYSKVDSKVKKEFIDQYLNEATPKLTSE LSKKVYDFLTKQKSNREMVDFMMGGILSSDLNIKGQPYLIVEPMPNLYFTRDP FASVGNGATIHWMKHNVRRREVLFANFIFKYNERFQNTPKYITPTKGLDIEGG DVFVYNKKTLVVGVSERTKMETIKELAKNISKNKECTFTKIYAINVPKMPNLM HLDTWLTMLDYNKFLYSPNMLSVLKVWEINISNNKVSAPKELNVNLEKALSMI IGKKPILIPVAGANASQIDINIETNFDATNYLVIEPGVVVGYSRNKKTEEALV KAGIKVLPFHGNQLSLGMGSARCMSMPLYREDV | 51 |
| Mycoplasma penetrans | MSSIDKNSLGNGINVYSEIGELKEVLVHTPGDEIRYTAPSRLEELLFSAVLKA DTAIEEHKGFVKILQNNGIKVIQLCDLVAETYELCSKEVRNSFIEQYLDEALP VLKKEIRPVVKDYLLSFPTVQMVRKMMSGILANELNIKQDNPLIIDGMPNLYF TRDPFASMGNGVSINCMKYPTRKREVIFSRFVFTNNPKYKNTPRYFDIVGNNG TIEGGDIFIYNSKTLVIGNSERTNFAAIESVAKNIQANKDCTFERIVVINVPP MPNLMHLDTWLTMLDYDKFLYSPNMMNVLKIWEIDLNVKPVKFVEKKGTLEEV LYSIIDKKPILIPIAGKGANQLDIDIETHFDGTNYLTIAPGVVVGYERNEKTQ KALVEAGIKVLSFNGSQLSLGMGSARCMSMPLIRENLKK | 52 |

TABLE A1-continued

ADI Polypeptide Sequences

| Source | Sequence | SEQ ID NO: |
|---|---|---|
| Mycoplasma fermentans | MKKINVYSEYGKLKEVLVHTPGDEIRRIAPSRLDELLFSAILEPDSAIAEHKR FVQLLKDNGIKVIQLDELFAKTFDLVSESVKQSFIERWLDECEPKLDATLRAK VKEYILELKAKSSKKHVRVMMAGIDKKELGIELDRDLVVDPMPNLYFTRDPFA SVGNGISLHHMKYVTRQRETIFSEFIFDNNLDYNTVPRWFDRKDEGRIEGGDV FIYSADTLVVGVSERTNKEAINVMARKIAADKEVKFKRIYAINVPPMPNLMHL DTWLTMLDKNKFLYSPNMLSVLKVWRIDLNDPDFVWHEIEGSLEEILEQIIGM KPILIPIAGKGASQLDIDIETHFDGTNYLTIAPSVVVGYSRNEKTEKALKAAK VKVLSFEGNQLSLGMGSARCMSMPLIREDIKKK | 53 |
| Mycoplasma pneumoniae | MKYNINVHSEIGQLQTVLVHTPGNEIRRISPRRLDDLLFSAVIEPDTAIQEHQ TFCQLLQEQNIEVVQLTDLTATTFDKANATAQNQFIETWLDQAEPKLTPEHRK VAKQYLLEQKAKSTLSMVRSMMGGIDKRKVAAANTINGDFLVDPMPNLYFTRD PFASIGHGISINRMKYLTRRRETLFASFIFANHPIIAARKFYFKPIDMGTIEG GDIFVYDQQTVVMGLSERTTEAAINVLAKKIQQDSSTSFKRIFVINVPQLPNL MHLDTWLTMLDRNKFLYSPNMLAVLKAWRIDFTDPALKWNEIAGDLSTILHTI IGQKPMLIPIAGADANQTEIDIETHFDGTNYLTIAPSVVVGYARNKLTHQTLE AAGVKVIAFKGNQLSLGMGSARCMSMPLVRKPL | 54 |
| Mycoplasma sp. CAG: 877 | MEKIHVTSEIGPLKKVLLHRPGNELLNLTPDTLSRLLFDDIPYLPDAIKEHDE FADALRANGVEVVYLENLMADVLDLSDEIRDKFIKQFIYEAGIRTPKYKYLVF DYLDQITNSKKLVLKTMEGIQISDIPRRKREIEKSLVDLIETEDEFIADPMPN LYFTRDPFASVGEGISLNKMYSVTRNRETIYAEYIFKYHPDYKDQARLYYDRY NPYHIEGGDVLNINDHVLAIGISQRTTAEAIDQIAKNLFKDPECKIDTILAFN IPESRAFMHLDTVFTQVDYDKFTYHPGIMGTLQVFEITEGDDPNSDEDLTVTE INAPLEEILTKYVGRKVTLIPCAGGDKVSAEREQWNDGSNTLCIAPGVVVVYD RNNLTNAVLRSYGLKVIEIHGAELSRGRGGPRCMSMPLVREDI | 55 |
| Mycoplasma sp. CAG: 472 | MHVTSEIKKLKKVLVHRPGKELLNLTPDTLGRLLFDDIPYLKDAILEHDEFCQ ILRDNDVEVVYLEDLMAETLDENPQVKPSFIRQFIYEAGVRTPKYKDLLFDYL MSYTNNKELVLKTMEGIKVSEVHRNKQDSEYSLVDQISEETKFLAEPMPNLYF TRDPFASVGDGIILNKMHSVTRSRETIYAYYIFNYHPDYMDKVPKYYDRENPF SIEGGDVLNLNEHTLAIGISQRTSAEAIDLVAKNMFNDEKCNIDTILAFKIPE CRAFMHLDTVFTQIDIDKFTYHPGIMDTLEVFEITKNEDDLDEVRVIKKEGSL ENILEEYLGIDITLIPCAGGDKIASEREQWNDGTNTLCIAPGVVVVYNRNNIT NEVLREKGIKVIEMNSAELSRGRGGPRCMSMPLERED | 56 |

Hence, in some embodiments, the ADI polypeptide in the ADI-PEG comprises, consists, or consists essentially of an illustrative sequence from Table A1 (SEQ ID NOs:1-56), or a variant or fragment thereof having ADI activity.

Certain embodiments include variants of the reference ADI polypeptide sequences described herein, whether described by name or by reference to a Table or sequence identifier (e.g., Table A1, SEQ ID NOs:1-56). A "variant" sequence refers to a polypeptide or polynucleotide sequence that differs from a reference sequence by one or more substitutions, deletions (e.g., truncations), additions, and/or insertions. Certain variants thus include fragments of a reference sequence described herein. Variant polypeptides are biologically active, that is, they continue to possess the enzymatic or binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present disclosure and still obtain a functional molecule that encodes a variant or derivative polypeptide with desirable characteristics. When it is desired to alter the amino acid sequence of a polypeptide to create an equivalent, or even an improved, variant or portion of a polypeptide described herein, one skilled in the art will typically change one or more of the codons of the encoding DNA sequence.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5);

valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a preferred embodiment, variant polypeptides differ from a native or reference sequence by substitution, deletion or addition of fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In certain embodiments, a polypeptide sequence is about, at least about, or up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 800, 810, 820, 830, 840, 850, 860, 870, 880, 890, 900, 900, 910, 920, 930, 940, 950, 960, 970, 980, 990, 1000 or more contiguous amino acids in length, including all integers in between, and which may comprise all or a portion of a reference sequence (see, e.g., Sequence Listing).

In some embodiments, a polypeptide sequence consists of about or no more than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800. 800, 810, 820, 830, 840, 850, 860, 870, 880, 890, 900, 900, 910, 920, 930, 940, 950, 960, 970, 980, 990, 1000 or more contiguous amino acids, including all integers in between, and which may comprise all or a portion of a reference sequence (see, e.g., Sequence Listing).

In certain embodiments, a polypeptide sequence is about 10-1000, 10-900, 10-800, 10-700, 10-600, 10-500, 10-400, 10-300, 10-200, 10-100, 10-50, 10-40, 10-30, 10-20, 20-1000, 20-900, 20-800, 20-700, 20-600, 20-500, 20-400, 20-300, 20-200, 20-100, 20-50, 20-40, 20-30, 50-1000, 50-900, 50-800, 50-700, 50-600, 50-500, 50-400, 50-300, 50-200, 50-100, 100-1000, 100-900, 100-800, 100-700, 100-600, 100-500, 100-400, 100-300, 100-200, 200-1000, 200-900, 200-800, 200-700, 200-600, 200-500, 200-400, or 200-300 contiguous amino acids, including all ranges in between, and comprises all or a portion of a reference sequence. In certain embodiments, the C-terminal or N-terminal region of any reference polypeptide may be truncated by about 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 250, 300, 350, 400, 450, 500, 550, 600, 650, 700, 750, or 800 or more amino acids, or by about 10-50, 20-50, 50-100, 100-150, 150-200, 200-250, 250-300, 300-350, 350-400, 400-450, 450-500, 500-550, 550-600, 600-650, 650-700, 700-750, 750-800 or more amino acids, including all integers and ranges in between (e.g., 101, 102, 103, 104, 105), so long as the truncated polypeptide retains the binding properties and/or activity of the reference polypeptide. Typically, the biologically-active fragment has no less than about 1%, about 5%, about 10%, about 25%, or about 50% of an activity of the biologically-active reference polypeptide from which it is derived.

In general, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence. Moreover, sequences differing from the native or parent sequences by the addition (e.g., C-terminal addition, N-terminal addition, both), deletion, truncation, insertion, or substitution (e.g., conservative substitution) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids (including all integers and ranges in between) but which retain the properties or activities of a parent or reference polypeptide sequence are contemplated.

In some embodiments, variant polypeptides differ from reference sequence by at least one but by less than 50, 40, 30, 20, 15, 10, 8, 6, 5, 4, 3 or 2 amino acid residue(s). In certain embodiments, variant polypeptides differ from a reference sequence by at least 1% but less than 20%, 15%, 10% or 5% of the residues. (If this comparison requires alignment, the sequences should be aligned for maximum similarity. "Looped" out sequences from deletions or insertions, or mismatches, are considered differences.)

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (*J. Mol. Biol.* 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*Cabios.* 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules described herein. BLAST protein searches can be performed with the XBLAST program, score=50, wordlength=3 to obtain amino acid sequences homologous to protein molecules described herein. To obtain gapped alignments for comparison purposes, Gapped BLAST can be utilized as described in Altschul et al., (*Nucleic Acids Res.* 25: 3389-3402, 1997). When utilizing BLAST and Gapped BLAST programs, the default parameters of the respective programs (e.g., XBLAST and NBLAST) can be used.

In some embodiments, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, S', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In some embodiments, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA.* 89:10915-10919, 1992). GAP uses the algorithm of Needleman and Wunsch (*J Mol Biol.* 48:443-453, 1970) to find the alignment of two complete sequences that maximizes the number of matches and minimizes the number of gaps.

In particular embodiments, the variant polypeptide comprises an amino acid sequence that can be optimally aligned with a reference polypeptide sequence (see, e.g., Sequence Listing) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (*PNAS USA.* 82: 488-492, 1985); Kunkel et al., (*Methods in Enzymol.* 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, *PNAS USA* 89: 7811-7815, 1992; Delgrave et al., *Protein Engineering.* 6: 327-331, 1993).

"Polyethylene glycol" or "PEG" refers to mixtures of condensation polymers of ethylene oxide and water, in a branched or straight chain, represented by the general formula $H(OCH_2CH_2)_nOH$, wherein n is at least 4. "Polyethylene glycol" or "PEG" is used in combination with a numeric suffix to indicate the approximate weight average molecular weight thereof. For example, PEG5,000 refers to PEG having a total weight average molecular weight of about 5,000; PEG12,000 refers to PEG having a total weight average molecular weight of about 12,000; and PEG20,000 refers to PEG having a total weight average molecular weight of about 20,000.

In some embodiments, the PEG has a total weight average molecular weight of about 1,000 to about 50,000; about 3,000 to about 40,000; about 5,000 to about 30,000; about 8,000 to about 30,000; about 11,000 to about 30,000; about 12,000 to about 28,000; about 16,000 to about 24,000; about 18,000 to about 22,000; or about 19,000 to about 21,000. In some embodiments, the PEG has a total weight average molecular weight of about 1,000 to about 50,000; about 3,000 to about 30,000; about 3,000 to about 20,000; about 4,000 to about 12,000; about 4,000 to about 10,000; about 4,000 to about 8,000; about 4,000 to about 6,000; or about 5,000. In specific embodiments, the PEG has a total weight average molecular weight of about 20,000. Generally, PEG with a molecular weight of 30,000 or more is difficult to dissolve, and yields of the formulated product may be reduced. The PEG may be a branched or straight chain Generally, increasing the molecular weight of the PEG decreases the immunogenicity of the ADI. The PEG may be a branched or straight chain, and in certain embodiments is a straight chain. The PEG having a molecular weight described herein may be used in conjunction with ADI, and optionally, a biocompatible linker.

Certain embodiments employ thiol, sulfhydryl, or cysteine-reactive PEG(s). In some embodiments, the thiol, sulfhydryl, or cysteine-reactive PEG(s) are attached to one or more naturally-occurring cysteine residues, one or more introduced cysteine residues (e.g., substitution of one or more wild-type residues with cysteine residue(s)), insertion of one or more cysteine residues), or any combination thereof (see, e.g., Doherty et al., Bioconjug Chem. 16:1291-98, 2005). In certain embodiments, certain of the wild-type ADI cysteines residues may be first substituted with another amino acid to prevent attachment of the PEG polymer to wild-type cysteines, for example, to prevent the PEG(s) from disrupting an otherwise desirable biological activity. Some embodiments employ one or more non-natural cysteine derivatives (e.g., homocysteine) instead of cysteine.

Figure 1D:
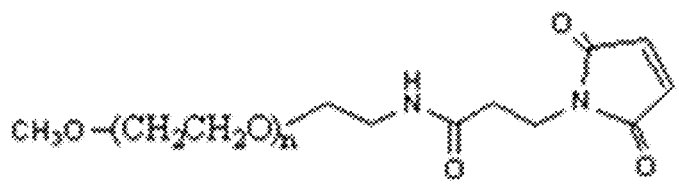

Non-limiting examples of thiol, sulfhydryl, or cysteine-reactive PEGs include Methoxy PEG Maleimides (M-PEG-MAL) (e.g., MW 2000, MW 5000, MW 10000, MW 20000, MW 30000, MW 40000). M-PEG-MALs react with the thiol groups on cysteine side chains in proteins and peptides to generate a stable 3-thiosuccinimidyl ether linkage. This reaction is highly selective and can take place under mild conditions at about pH 5.0-6.5 in the presence of other functional groups. Particular examples of commercially-available thiol, sulfyhdryl, or cysteine-reactive PEG molecules are illustrated in FIGS. 1A-1D. Thus, in certain embodiments, an ADI enzyme is conjugated to any one or more of the thiol, sulfhydryl, or cysteine-reactive PEG molecules described herein.

ADI may be covalently bonded to a modifying agent, such as PEG, with or without a linker, although a preferred embodiment utilizes a linker. ADI may be covalently bonded to PEG via a biocompatible linker using methods known in the art, as described, for example, by Park et al, Anticancer Res., 1:373-376 (1981); and Zaplipsky and Lee, Polyethylene Glycol Chemistry: Biotechnical and Biomedical Applications, J. M. Harris, ed., Plenum Press, NY, Chapter 21 (1992), the disclosures of which are hereby incorporated by reference herein in their entirety. In some instances, ADI may be coupled directly (i.e., without a linker) to a modifying agent such as PEG, for example, through an amino group, a sulfhydryl group, a hydroxyl group, a carboxyl group, or other group.

The linker used to covalently attach ADI to a modifying agent (e.g. PEG) can be any biocompatible linker. As discussed above, "biocompatible" indicates that the compound or group is non-toxic and may be utilized in vitro or in vivo without causing injury, sickness, disease, or death. A modifying agent such as PEG can be bonded to the linker, for example, via an ether bond, a thiol bond, an amide bond, or other bond.

In some embodiments, suitable linkers can have an overall chain length of about 1-100 atoms, 1-80 atoms, 1-60 atoms, 1-40 atoms, 1-30 atoms, 1-20 atoms, or 1, 2, 3, 4, 5, 6, 7, 8, 9, 10, 11, 12, 13, 14, 15, 16, 17, 18, 19, or 20 atoms, for example, wherein the atoms in the chain comprise C, S, N, P, and/or O. In certain embodiments, a linker is optional, e.g., a PEG conjugated ADI enzyme does not comprise a linker. In some instances, a linker group includes, for example, a succinyl group, an amide group, an imide group, a carbamate group, an ester group, an epoxy group, a carboxyl group, a hydroxyl group, a carbohydrate, a tyrosine group, a cysteine group, a histidine group, a methylene group, and combinations thereof. Particular examples of stable linkers include succinimide, propionic acid, carboxymethylate linkages, ethers, carbamates, amides, amines, carbamides, imides, aliphatic C—C bonds, and thio ethers. In certain embodiments, the biocompatible linker is a succinimidyl succinate (SS) group.

Other suitable linkers include an oxycarbonylimidazole group (including, for example, carbonylimidazole (CDI)), a nitro phenyl group (including, for example, nitrophenyl carbonate (NCP) or trichlorophenyl carbonate (TCP)), a trysylate group, an aldehyde group, an isocyanate group, a vinylsulfone group, or a primary amine. In certain embodiments, the linker is derived from SS, SPA, SCM, or NHS; in certain embodiments, SS, SPA, or NHS are used, and in some embodiments, SS or SPA are used. Thus, in certain embodiments, potential linkers can be formed from methoxy-PEG succinimidyl succinate (SS), methoxy-PEG succinimidyl glutarate (SG), methoxy-PEG succinimidyl carbonate (SC), methoxy-PEG succinimidyl carboxymethyl ester (SCM), methoxy-PEG2 N-hydroxy succinimide (NHS), methoxy-PEG succinimidyl butanoate (SBA), methoxy-PEG succinimidyl propionate (SPA), methoxy-PEG succinimidyl glutaramide, and/or methoxy-PEG succinimidyl succinimide.

Additional examples of linkers include, but are not limited to, one or more of the following: —O—, —NH—, —S—, —C(O)—, C(O)—NH, NH—C(O)—NH, O—C(O)—NH, —C(S)—, —CH2-, —CH2-CH2-, —CH2-CH2-CH2-, —CH2-CH2-CH2-CH2-, —O—CH2-, —CH2-O—, —O—CH2-CH2-, —CH2-O—CH2-, —CH2-CH2-O—, —O—CH2-CH2-CH2-, —CH2-O—CH2-CH2-, —CH2-CH2-O—CH2-, —CH2-CH2-CH2-O—, —O—CH2-CH2-CH2-CH2-, —CH2-O—CH2-CH2-CH2-, —CH2-CH2-O—CH2-CH2-, —CH2-CH2-CH2-O—CH2-, —CH2-CH2-CH2-CH2-O—, —C(O)—NH—CH2-, —C(O)—NH—CH2-CH2-, —CH2-C(O)—NH—CH2-, —CH2-CH2-C(O)—NH—, —C(O)—NH—CH2-CH2-CH2-, —CH2-C(O)—NH—CH2-CH2-, —CH2-CH2-C(O)—NH—CH2-, —CH2-CH2-CH2-C(O)—NH—, —C(O)—NH—CH2-CH2-CH2-CH2-, —CH2-C(O)—NH—CH2-CH2-CH2-, —CH2-CH2-C(O)—NH—CH2-CH2-, —CH2-CH2-CH2-C(O)—NH—CH2-, —CH2-CH2-CH2-CH2-C(O)—NH—, —CH2-CH2-CH2-CH2-C(O)—NH—NH—CH2-CH2-, —CH2-CH2-CH2-CH2-C(O)—NH—NH—C(O)—CH2-, —CH2-NH—C(O)—CH2-, —CH2-CH2-NH—C(O)—CH2-, —NH—C(O)—CH2-CH2-, —CH2-NH—C(O)—CH2-CH2, —CH2-CH2-NH—C(O)—CH2-CH2, —C(O)—NH—CH2-, —C(O)—NH—CH2-CH2-, —O—C(O)—NH—CH2-, —O—C(O)—NH—CH2-CH2-, —NH—CH2-, —NH—CH2-CH2-, —CH2-NH—CH2-, —CH2-CH2-NH—CH2-, —C(O)—CH2-, —C(O)—CH2-CH2-, —CH2-C(O)—CH2-, —CH2-C(O)—CH2-, —CH2-CH2-C(O)—CH2-CH2-, —CH2-CH2-C(O)—, —CH2-CH2-CH2-C(O)—NH—CH2-CH2-NH—, —CH2-CH2-CH2-C(O)—NH—CH2-CH2-NH—C(O)—, —CH2-CH2-CH2-C(O)—NH—CH2-CH2-NH—C(O)—CH2-, bivalent cycloalkyl group, —N(R6)-, R6 is H or an organic radical selected from the group consisting of alkyl, substituted alkyl, alkenyl, substituted alkenyl, alkynyl, substituted alkynyl, aryl and substituted aryl. Additionally, any of the linker moieties described herein may further include an ethylene oxide oligomer chain comprising 1 to 20 ethylene oxide monomer units [i.e., —(CH$_2$CH$_2$O)$_{1-20}$—]. That is, the ethylene oxide oligomer chain can occur before or after the linker, and optionally in between any two atoms of a linker moiety comprised of two or more atoms. Also, the oligomer chain would not be considered part of the linker moiety if the oligomer is adjacent to a polymer segment and merely represent an extension of the polymer segment.

In certain embodiments, the ADI enzyme comprises one or more PEG molecules and/or linkers as described herein. In certain embodiments, the linker is a water-labile linker.

The attachment of PEG to ADI increases the circulating half-life of ADI. Generally, PEG is attached to a primary amine of ADI. Selection of the attachment site of PEG, or other modifying agent, on the ADI is determined by the role of each of the sites within the active domain of the protein, as would be known to the skilled artisan. PEG may be attached to the primary amines of ADI without substantial loss of enzymatic activity. For example, the lysine residues present in ADI are all possible points at which ADI as described herein can be attached to PEG via a biocompatible linker, such as SS, SPA, SCM, SSA and/or NHS. PEG may also be attached to other sites on ADI, as would be apparent to one skilled in the art in view of the present disclosure.

From 1 to about 30 PEG molecules may be covalently bonded to ADI. In certain embodiments, ADI is modified with (i.e., comprises) one PEG molecule. In some embodiments, the ADI is modified with more than one PEG molecule. In particular embodiments, the ADI is modified with about 1 to about 10, or from about 7 to about 15 PEG molecules, or from about 2 to about 8 or about 9 to about 12 PEG molecules. In some embodiments, the ADI is modified with about 2, 3, 4, 5, 6, 7, 8, 9, 10, 11, 12, 13, 14, or 15 PEG molecules. In specific embodiments, ADI is modified with 4.5-5.5 PEG molecules per ADI. In some embodiment, ADI is modified with 5±1.5 PEG molecules.

In certain embodiments, about 15% to about 70% of the primary amino groups in ADI are modified with PEG, in some embodiments about 20% to about 65%, about 25% to about 60%, or in certain embodiments about 30% to about 55%, or 45% to about 50%, or in some embodiments about 50% of the primary amino groups in arginine deiminase are modified with PEG. When PEG is covalently bonded to the end terminus of ADI, it may be desirable to have only 1 PEG molecule utilized. Increasing the number of PEG units on ADI increases the circulating half-life of the enzyme. However, increasing the number of PEG units on ADI decreases the specific activity of the enzyme. Thus, a balance needs to be achieved between the two, as would be apparent to one skilled in the art in view of the present disclosure.

In some embodiments, a common feature of biocompatible linkers is that they attach to a primary amine of arginine deiminase via a succinimide group. Once coupled with ADI, SS-PEG has an ester linkage next to the PEG, which may render this site sensitive to serum esterase, which may release PEG from ADI in the body. SPA-PEG and PEG2-NHS do not have an ester linkage, so they are not sensitive to serum esterase.

PEG which is attached to the protein may be either a straight chain, as with SS-PEG, SPA-PEG and SC-PEG, or a branched chain of PEG may be used, as with PEG2-NHS.

In some embodiments, for example, the amino acid substitutions employ non-natural amino acids for conjugation to PEG or other modifying agent (see, e.g., de Graaf et al., Bioconjug Chem. 20:1281-95, 2009). Certain embodiments thus include an ADI enzyme that is conjugated to one or more PEGs via one or more non-natural amino acids. In some embodiments the non-natural amino acid comprises a side chain having a functional group selected from the group consisting of: an alkyl, aryl, aryl halide, vinyl halide, alkyl halide, acetyl, ketone, aziridine, nitrile, nitro, halide, acyl, keto, azido, hydroxyl, hydrazine, cyano, halo, hydrazide, alkenyl, alkynyl, ether, thio ether, epoxide, sulfone, boronic acid, boronate ester, borane, phenylboronic acid, thiol, seleno, sulfonyl, borate, boronate, phospho, phosphono, phosphine, heterocyclic-, pyridyl, naphthyl, benzophenone, a constrained ring such as a cyclooctyne, thioester, enone, imine, aldehyde, ester, thioacid, hydroxylamine, amino, carboxylic acid, alpha-keto carboxylic acid, alpha or beta unsaturated acids and amides, glyoxyl amide, and an organosilane group. In some embodiments, the non-natural amino acid is selected from the group consisting of: p-acetyl-L-phenylalanine, O-methyl-L-tyrosine, L-3-(2-naphthyl)alanine, 3-methyl-phenylalanine, O-4-allyl-L-tyrosine, homocysteine, 4-propyl-L-tyrosine, tri-O-acetyl-GlcNAcβ-serine, β-O-GlcNAc-L-serine, tri-O-acetyl-GalNAc-α-threonine, α-GalNAc-L-threonine, L-Dopa, a fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, and isopropyl-L-phenylalanine.

While ADI-PEG is the illustrative modified ADI described herein, as would be recognized by the skilled person ADI may be modified with other polymers or appropriate molecules for the desired effect, in particular reducing antigenicity and increasing serum half-life.

It is to be understood that some embodiments are based on the understanding that certain structural characteristics of arginine deiminase may prevent or interfere with the proper and rapid renaturation when produced via recombinant technology. In particular, these structural characteristics hinder or prevent the enzyme from assuming an active conformation during recombinant production. In some embodiments, the term "active conformation" is defined as a three-dimensional structure that allows for enzymatic activity by unmodified or modified arginine deiminase. The active conformation may, in particular, be necessary for catalyzing the conversion of arginine into citrulline. The term "structural characteristic" may be defined as any trait, quality or property of the polypeptide chain resulting from a particular amino acid or combination of amino acids. For instance, arginine deiminase may contain an amino acid that results in a bend or kink in the normal peptide chain and thus hinders the enzyme from assuming an active conformation during renaturation of the enzyme. In particular, arginine deiminase from *Mycoplasma hominis* has a proline at the 210 position that may result in a bend or kink in the peptide chain, making it more difficult to renature the enzyme during recombinant production. It is to be understood that arginine deiminase derived from other organisms may also have sites corresponding to the 210 position of arginine deiminase from *Mycoplasma* hominis.

Some embodiments provide for specific amino acid substitutions in the polypeptide chain of wild type arginine deiminases. For instance, in some embodiments, the proline at position 210 (or the equivalent residue) is substituted with serine. Non-limiting examples of other substitutions include Pro210 to Thr210, Pro210 to Arg210, Pro210 to Asn210, Pro210 to Gln210 or Pro210 to Met210.

In specific embodiments, the modified ADI is ADI-PEG 20. ADI-PEG 20 refers to the ADI molecule described, for example, in U.S. Pat. Nos. 6,183,738; 6,635,462; Ascierto P A, et al. (2005) Pegylated arginine deiminase treatment of patients with metastatic melanoma: results from phase I and II studies. J Clin Oncol 23(30): 7660-7668; Izzo F, et al. (2004) Pegylated arginine deiminase treatment of patients with unresectable hepatocellular carcinoma: results from phase I/II studies. J Clin Oncol 22(10): 1815-1822; Holtsberg F W, et al. (2002), Poly(ethylene glycol) (PEG) conjugated arginine deiminase: effects of PEG formulations on its pharmacological properties. J Control Release 80(1-3): 259-271; and Kelly et al., (2012) British Journal of Cancer 106, 324-332. As would be recognized by the skilled artisan, ADI-PEG 20 is a pegylated ADI enzyme derived from *M. hominis* (mass average of about 5.5±1.0 bonded PEG 20,000 molecules), which has two substitutions (K112E; P210S) relative to the wild type *M. hominis* ADI sequence.

In certain embodiments, the ADI-PEG in the formulation retains at least 50, 55, 60, 65, 70, 75, 80, 85, 90, or 95% of its ADI activity, for example, relative to a corresponding ADI-PEG in a non-lyophilized liquid control composition. In some embodiments, the ADI-PEG retains at least 50, 55, 60, 65, 70, 75, 80, 85, 90, or 95% of its (original) ADI activity after being stored as a lyophilized formulation for about or at least about 1, 2, 3, or 4 weeks, or about or at least about 1, 2, 3, 4, 5, 6, 7, 8, 9, 10, 11, 12, 13, 14, 15, 16, 17, 18, 19, 20, 21, 22, 23, 24, 36, 48, 60, or 72 months. In some embodiments, the ADI activity is retained after being stored at a temperature of about 2-8° C., or at about room temperature, or at a stressed-temperature, for example, a temperature of about or at least about 50-60° C. In certain embodiments, the ADI-PEG retains at least 50, 55, 60, 65, 70, 75, 80, 85, 90, 95, or 100% of the (original) PEG molecules (per ADI monomer/protomer), for example, relative to a corresponding ADI-PEG in a non-lyophilized liquid control composition.

The skilled artisan will appreciate that the various ADI-PEG polypeptides described herein can be combined with any one or more of the various formulation components described herein, and used according to any one or more of the methods and compositions described herein.

Reconstituted Liquid Compositions and Related Methods

Certain embodiments include reconstituted liquid compositions, methods of reconstituting the liquid compositions, and methods of using the same for arginine depletion therapies, including the treatment of various cancers.

For instance, certain embodiments include methods of reconstituting a lyophilized formulation described herein, comprising adding a pharmaceutically-acceptable solvent or diluent to the lyophilized formulation to form a reconstituted liquid composition. Also included are reconstituted liquid compositions prepared by any method described herein. Certain exemplary embodiments relate to reconstituted liquid compositions, comprising a lyophilized formulation described herein and a pharmaceutically-acceptable diluent or solvent, that is, where the lyophilized formulation is dissolved or otherwise solubilized in the solvent to form a liquid composition.

In particular embodiments, the solvent or diluent is water, or sterile water. In some instances, the lyophilized formulation is reconstituted to a substantially aggregate-free solution of about 5-20 mg/ml ADI-PEG (for example, about 5, 6, 7, 8, 9, 10, 11, 12, 13, 14, 15, 16, 17, 18, 19, or 20 mg/ml ADI-PEG) in a time of about or less than about five, four, three, two, or one minutes.

In some embodiments, the ADI-PEG in the reconstituted liquid composition retains at least 50, 55, 60, 65, 70, 75, 80, 85, 90, or 95% of its arginine deiminase (ADI) activity, for example, relative to a corresponding ADI-PEG in a non-lyophilized liquid control composition. In some embodiments, the ADI-PEG in the reconstituted liquid composition retains at least 50, 55, 60, 65, 70, 75, 80, 85, 90, or 95% of its ADI activity after being stored as a lyophilized formulation for about or at least about 1, 2, 3, or 4 weeks, or about or at least about 1, 2, 3, 4, 5, 6, 7, 8, 9, 10, 11, 12, 13, 14, 15, 16, 17, 18, 19, 20, 21, 22, 23, 24, 36, 48, 60, or 72 months. In some embodiments, the ADI activity is retained after being stored at a temperature of about 2-8° C., or at about room temperature, or at a stressed-temperature, for example, a temperature of about or at least about 50-60° C. In some embodiments, the specific ADI enzyme activity of the ADI-PEG in the reconstituted liquid formulation is about 5.0 to about 120 IU/mg, or about 5.5, 6, 6.5, 7, 7.5, 8, 8.5, 9.0, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 35, 40, 45, 50, 55, 55, 60, 65, 70, 75, 80, 85, 90, 95, 100, 105, 110, 115, or 120 IU/mg, including all integers and ranges in between.

In certain embodiments, ADI-PEG in the reconstituted liquid composition retains at least 50, 55, 60, 65, 70, 75, 80, 85, 90, 95, or 100% of the (original) PEG molecules (per ADI monomer/protomer) upon reconstitution, for example, relative to a corresponding ADI-PEG in a non-lyophilized liquid control composition. In some embodiments, ADI-PEG in the reconstituted liquid composition retains at least 50, 55, 60, 65, 70, 75, 80, 85, 90, 95, or 100% of the (original) PEG molecules (per ADI monomer/protomer) upon reconstitution, for example, after being stored as a lyophilized formulation for about or at least about 1, 2, 3, or 4 weeks, or about or at least about 1, 2, 3, 4, 5, 6, 7, 8, 9, 10, 11, 12, 13, 14, 15, 16, 17, 18, 19, 20, 21, 22, 23, 24, 36, 48, 60, or 72 months, optionally after being stored at a temperature of about 2-8° C. and/or about room temperature.

In some embodiments, the ADI-PEG in the liquid composition has an osmolality of about 50 mOsm/kg to about 500 mOsm/kg, or about 50, 55, 60, 65, 70, 75, 80, 85, 90, 95, 100, 105, 110, 120, 125, 130, 135, 140, 145, 150, 155, 160, 165, 170, 175, 180, 185, 190, 195, 200, 205, 210, 220, 225, 230, 235, 240, 245, 250, 255, 260, 265, 270, 275, 280, 285, 290, 295, 300, 305, 310, 320, 325, 330, 335, 340, 345, 350, 355, 360, 365, 370, 375, 380, 385, 390, 395, 400, 405, 410, 420, 425, 430, 435, 440, 445, 450, 455, 460, 465, 470, 475, 480, 485, 490, 495, or about 500 mOsm/kg, including all integers and ranges in between. In some embodiments, the reconstituted liquid composition is suitable for injection into a subject, for example, a human subject.

Also included are methods of using the reconstituted liquid compositions for arginine depletion therapies. For example, certain embodiments include methods of treating, ameliorating the symptoms of, or inhibiting the progression of, a cancer in a subject in need thereof, comprising administering to the subject a reconstituted liquid formulation described herein.

The methods and compositions described herein can be used in the treatment of any variety of cancers. In some embodiments, the cancer is selected from one or more of hepatocellular carcinoma (HCC), melanoma, metastatic melanoma, pancreatic cancer, prostate cancer, small cell lung cancer, mesothelioma, lymphocytic leukemia, chronic myelogenous leukemia, lymphoma, hepatoma, sarcoma, leukemia, acute myeloid leukemia, relapsed acute myeloid leukemia, B-cell malignancy, breast cancer, ovarian cancer, colorectal cancer, gastric cancer, glioma (e.g., astrocytoma, oligodendroglioma, ependymoma, or a choroid plexus papilloma), glioblastoma multiforme (e.g., giant cell gliobastoma or a gliosarcoma), meningioma, pituitary adenoma, vestibular schwannoma, primary CNS lymphoma, primitive neuroectodermal tumor (medulloblastoma), non-small cell lung cancer (NSCLC), kidney cancer, bladder cancer, uterine cancer, esophageal cancer, brain cancer, head and neck cancers, cervical cancer, testicular cancer, and stomach cancer.

In some embodiments, the cancer exhibits reduced expression and/or activity of argininosuccinate synthetase-1 (ASS-1), or is otherwise argininosuccinate synthetase-1-deficient. In some instances, reduced ASS-1 expression or activity is a reduction in expression and/or activity of about 5%, 10%, 15%, 20%, 25%, 30%, 35%, 40%, 45%, 50%, 55%, 60%, 65%, 70%, or more, relative to expression and/or activity in an appropriate control sample, for example, a normal cell or tissue. In certain embodiments, ASS or ASL expression or activity is reduced by at least two-fold relative to expression or activity in a control sample. Reduction in ASS-1 expression or activity can be measured according to routine techniques the art, including, for example, quantitative PCR, immunohistochemistry, enzyme activity assays (e.g., ADI activity assays to measure conversion of citrulline into argininosuccinate or conversion of argininosuccinate into arginine and fumarate), and the like.

In some embodiments, the methods or compositions described herein increase median survival time of a patient by 4 weeks, 5 weeks, 6 weeks, 7 weeks, 8 weeks, 9 weeks, 10 weeks, 15 weeks, 20 weeks, 25 weeks, 30 weeks, 40 weeks, or longer. In certain embodiments, the methods or compositions described herein increase median survival time of a patient by 1 year, 2 years, 3 years, or longer. In some embodiments, the methods or compositions described herein increase progression-free survival by 2 weeks, 3 weeks, 4 weeks, 5 weeks, 6 weeks, 7 weeks, 8 weeks, 9 weeks, 10 weeks or longer. In certain embodiments, the methods or compositions described herein increase progression-free survival by 1 year, 2 years, 3 years, or longer.

In certain embodiments, the composition administered is sufficient to result in tumor regression, as indicated by a statistically significant decrease in the amount of viable tumor, for example, at least a 10%, 20%, 30%, 40%, 50% or greater decrease in tumor mass, or by altered (e.g., decreased with statistical significance) scan dimensions. In certain embodiments, the composition administered is sufficient to result in stable disease. In certain embodiments, the composition administered is sufficient to result in stabilization or clinically relevant reduction in symptoms of a particular disease indication known to the skilled clinician.

The methods or compositions for treating cancers can be combined with other therapeutic modalities. For example, a compositions described herein can be administered to a subject before, during, or after other therapeutic interventions, including symptomatic care, radiotherapy, surgery, transplantation, hormone therapy, photodynamic therapy, antibiotic therapy, or any combination thereof. Symptomatic care includes administration of corticosteroids, to reduce cerebral edema, headaches, cognitive dysfunction, and emesis, and administration of anti-convulsants, to reduce seizures. Radiotherapy includes whole-brain irradiation, fractionated radiotherapy, and radiosurgery, such as stereotactic radiosurgery, which can be further combined with traditional surgery.

Methods for identifying subjects with one or more of the diseases or conditions described herein are known in the art.

Administration may be achieved by a variety of different routes, including oral, parenteral, intranasal, intravenous, intradermal, intramuscular, intrathecal, subcutaneous, sublingual, buccal, rectal, vaginal, and topical. Preferred modes of administration depend upon the nature of the condition to be treated or prevented. Particular embodiments include administration by IV infusion.

The precise dosage and duration of treatment is a function of the disease being treated and may be determined empirically using known testing protocols or by testing the compositions in model systems known in the art and extrapolating therefrom. Controlled clinical trials may also be performed. Dosages may also vary with the severity of the condition to be alleviated. A pharmaceutical composition is generally formulated and administered to exert a therapeutically useful effect while minimizing undesirable side effects. The composition may be administered one time, or may be divided into a number of smaller doses to be administered at intervals of time. For any particular subject, specific dosage regimens may be adjusted over time according to the individual need.

In some embodiments, a therapeutically effective amount or therapeutic dosage of a composition described herein is an amount that is effective to reduce or stabilize tumor growth. In certain instances, treatment is initiated with small dosages which can be increased by small increments until the optimum effect under the circumstances is achieved.

In some embodiments, a dosage is administered from about once a day to about once every two or three weeks. For example, in certain embodiments, a dosage is administered about once every 1, 2, 3, 4, 5, 6, or 7 days, or about once a week, or about twice a week, or about three times a week, or about once every two or three weeks.

In some embodiments, the dosage is from about 0.1 mg/kg to about 20 mg/kg, or to about 10 mg/kg, or to about 5 mg/kg, or to about 3 mg/kg. In some embodiments, the dosage is about 0.10 mg/kg, 0.15 mg/kg, 0.20 mg/kg, 0.25 mg/kg, 0.30 mg/kg, 0.35 mg/kg, 0.40 mg/kg, 0.45 mg/kg, 0.50 mg/kg, 0.55 mg/kg, 0.60 mg/kg, 0.65 mg/kg, 0.70 mg/kg, 0.75 mg/kg, 0.80 mg/kg, 0.85 mg/kg, 0.90 mg/kg, 0.95 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg. 7.0 mg/kg, 7.5 mg/kg, 8.0 mg/kg, 8.5 mg/kg, 9.0 mg/kg, 9.5 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, or 20 mg/kg, including all integers and ranges in between. In specific embodiments, the dosage is about 1 mg/kg once a week as a 2 ml intravenous injection to about 20 mg/kg once every 3 days.

In some embodiments, the dosage is from about 50 $IU/m^2$ to about 1000 $IU/m^2$. In particular embodiments, the dosage is about 50 $IU/m^2$, 60 $IU/m^2$, 70 $IU/m^2$, 80 $IU/m^2$, 90 $IU/m^2$, 100 $IU/m^2$, 110 $IU/m^2$, 120 $IU/m^2$, 130 $IU/m^2$, 140 $IU/m^2$, 150 $IU/m^2$, 160 $IU/m^2$, 170 $IU/m^2$, 180 $IU/m^2$, 190 $IU/m^2$, 200 $IU/m^2$, 210 $IU/m^2$, 220 $IU/m^2$, 230 $IU/m^2$, 240 $IU/m^2$, 250 $IU/m^2$, 260 $IU/m^2$, 270 $IU/m^2$, 280 $IU/m^2$, 290 $IU/m^2$, 300 $IU/m^2$, 310 $IU/m^2$, about 320 $IU/m^2$, about 330 $IU/m^2$, 340 $IU/m^2$ about 350 $IU/m^2$, 360 $IU/m^2$, 370 $IU/m^2$, 380 $IU/m^2$, 390 $IU/m^2$, 400 $IU/m^2$, 410 $IU/m^2$, 420 $IU/m^2$, 430 $IU/m^2$, 440 $IU/m^2$, 450 $IU/m^2$, 500 $IU/m^2$, 550 $IU/m^2$, 600 $IU/m^2$, 620 $IU/m^2$, 630 $IU/m^2$, 640 $IU/m^2$, 650 $IU/m^2$, 660 $IU/m^2$, 670 $IU/m^2$, 680 $IU/m^2$, 690 $IU/m^2$, 700 $IU/m^2$, 710 $IU/m^2$, 720 $IU/m^2$, 730 $IU/m^2$, 740 $IU/m^2$, 750 $IU/m^2$, 760 $IU/m^2$, 770 $IU/m^2$, 780 $IU/m^2$, 790 $IU/m^2$, 800 $IU/m^2$, 810 $IU/m^2$, 820 $IU/m^2$, 830 $IU/m^2$, 840 $IU/m^2$, 850 $IU/m^2$, 860 $IU/m^2$, 870 $IU/m^2$, 880 $IU/m^2$, 890 $IU/m^2$, 900 $IU/m^2$, 910 $IU/m^2$, 920 $IU/m^2$, 930 $IU/m^2$, 940 $IU/m^2$, 950 $IU/m^2$, 960 $IU/m^2$, 970 $IU/m^2$, 980 $IU/m^2$, 990 $IU/m^2$, or about 1000 $IU/m^2$, including all integers and ranges in between.

Also included are patient care kits, comprising one or more lyophilized formulations described herein. Certain kits also comprise one or more pharmaceutically-acceptable diluents or solvents, such as water (e.g., sterile water). In some embodiments, the lyophilized formulations are stored in vials, cartridges, dual chamber syringes, and/or pre-filled mixing systems.

The kits herein may also include a one or more additional therapeutic agents or other components suitable or desired for the indication being treated, or for the desired diagnostic application. The kits herein can also include one or more syringes or other components necessary or desired to facilitate an intended mode of delivery (e.g., stents, implantable depots, etc.).

All publications, patent applications, and issued patents cited in this specification are herein incorporated by reference as if each individual publication, patent application, or issued patent were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

In this study, various excipient types were evaluated for their ability to provide a lyophilized ADI-PEG 20 formulation with elegant cake appearance and maintained stability after the lyophilization process and reconstitution. Table E1 below provides a summary of the formulations tested in this study.

TABLE E1

| Formulation ID | Composition | Cryoprotectant | Lyoprotectant | Bulking Agent |
|---|---|---|---|---|
| F1 | 20 mM Sodium phosphate 130 mM Sodium chloride | No | No | No |
| F2 | 20 mM histidine | No | No | No |
| F3 | 20 mM histidine 5% Sucrose | Yes | Yes | No |
| F4 | 20 mM histidine 5% Mannitol | No | No | Yes |
| F5 | 20 mM histidine 1% Dextran 40 | Yes | No | Yes |
| F6 | 20 mM histidine 1% Dextran 40 5% Sucrose | Yes | Yes | Yes |
| F7 | 20 mM histidine 5% Trehalose | Yes | Yes | Yes |
| F8 | 20 mM histidine 4% Mannitol 1% Sucrose | Yes | Yes | Yes |
| F9 | 20 mM histidine 4.8% Sucrose 0.01% Tween-80* | Yes | Yes | No |
| F10 | 20 mM histidine 4.8% Sucrose 0.01% Tween-80* 0.25% Glycerol** | Yes | Yes | No |

Formulations at pH 6.8 ± 0.1
*Surfactant
**Plasticizer

The formulations of Table E1 were lyophilized in vials using a VirTis Genesis 25XL Lyophilizer. The shelves were precooled to 5° C. prior to loading the vials. The lyophilization cycle was as follows:

The shelf was maintained at 5° C. for 30 minutes;
the shelf was cooled to −40° C. at 1° C./min and held at −40° C. for one hour;
the shelf was heated to −35° C. at 1° C./min where primary drying occurred at 50 mtorr for 72 hours;
the shelf was heated to 20° C. at 0.1° C./min where secondary drying occurred at 50 mtorr for 8 hours.

The lyophilized formulations were evaluated by visual appearance before and after stressed-storage conditions of 60° C. for one week. All lyophilized formulations showed a white coloring after lyophilization, and an off-white to yellow coloring after stressed storage conditions.

The lyophilized formulations were also evaluated for enzyme activity and by size-exclusion chromatography relative to pre-lyophilized formulations (unshaded results), and also before and after stressed-storage conditions (shaded results). The results are shown in Tables E2 and E3 below.

TABLE E2

Enzyme Activity Evaluation ADI-PEG 20 Activity in IU/mL.

| Formulation | Pre-lyo | Post-lyo | % activity retained | Rank | 1 wk at 60° C. | % activity retained | Rank |
|---|---|---|---|---|---|---|---|
| F1 | 163 | 107 | 66 | + | 6 | 6 | ++ |
| F2 | 161 | 132 | 82 | +++ | 1 | 1 | + |
| F3 | 169 | 137 | 81 | +++ | 13 | 9 | ++ |
| F4 | 155 | 128 | 83 | +++ | 0 | 0 | + |
| F5 | 154 | 126 | 82 | +++ | 10 | 8 | ++ |
| F6 | 132 | 131 | 99 | ++++ | 14 | 11 | +++ |
| F7 | 147 | 152 | 103 | ++++ | 30 | 20 | +++ |
| F8 | 132 | 138 | 105 | ++++ | 34 | 25 | ++++ |
| F9 | 135 | 118 | 87 | +++ | 9 | 8 | ++ |
| F10 | 150 | 137 | 91 | ++++ | 8 | 6 | ++ |

TABLE E3

ADI-PEG 20 Apparent Concentration (mg/mL) Evaluation by SEC.

| Formulation | Pre-lyo | Post-lyo | % activity retained | Rank | 1 wk at 60° C. | % activity retained | Rank |
|---|---|---|---|---|---|---|---|
| F1 | 11.0 | 10.3 | 94 | ++ | 0.5 | 5 | + |
| F2 | 13.9 | 12.7 | 91 | ++ | 7.9 | 62 | ++ |
| F3 | 14.1 | 12.4 | 88 | + | 13 | 105 | +++ |
| F4 | 14.2 | 12.6 | 89 | + | 3.4 | 27 | + |
| F5 | 14.3 | 13 | 91 | ++ | 14.1 | 108 | +++ |
| F6 | 14.3 | 12.9 | 90 | ++ | 13.7 | 106 | +++ |
| F7 | 14.4 | 12.9 | 90 | ++ | 13.8 | 107 | +++ |
| F8 | 13.7 | 12.2 | 89 | + | 13.3 | 109 | +++ |
| F9 | 13.4 | 12.2 | 91 | ++ | 13.2 | 108 | +++ |
| F10 | 13.7 | 12.6 | 92 | ++ | 10.2 | 81 | ++ |

Total and free PEG levels (mg/ml) was also evaluated (data not shown) and the formulations were ranked and grouped according to the total number of + values assigned). The rankings from highest (Group 1) to lowest (Group 5) are shown in Table E4 below.

TABLE E4

| Rank | ID | Composition | Cryo-protectant | Lyo-protectant | Bulking Agent | Surfactant | Plasticizer |
|---|---|---|---|---|---|---|---|
| Group 1 | F6, F7, and F8 | F6: H + Dextran 40 + Sucrose<br>F7: H + Trehalose<br>F8: H + Mannitol + Sucrose | Yes | Yes | Yes | No | No |
| Group 2 | F5 | H + Dextran 40 | Yes | No | Yes | No | No |
| Group 3 | F3, F9, and F10 | F3: H + Sucrose<br>F9: H + Sucrose + Tween 80<br>F10: H + Sucrose + Tween 80 + Glycerol | Yes | Yes | Yes | No: F3<br>Yes: F9<br>Yes: F10 | No: F3<br>No: F9<br>Yes: F10 |
| Group 4 | F2 | Histidine (H) | No | No | No | No | No |
| Group 5 | F1 and F4 | F1: Phosphate<br>F4: H + Mannitol | No | No | No: F1<br>Yes: F4 | No | No |

To summarize, all of the ADI-PEG 20 formulations (F1-F10) prepared in this study resulted in elegant, uniform lyophilized cakes, and all appeared to remain stable based on the assessment from enzymatic activity and size exclusion chromatography. Results from the stressed storage conditions (60° C. for one week) indicate that the best lyophilized ADI-PEG 20 formulations contain a cryoprotectant and a lyoprotectant. The addition of a bulking agent such as dextran 40 or crystalline mannitol, or a high glass transition temperature excipient such as trehalose, appeared to attenuate activity loss and improve formation of the PEG molecules after reconstitution.

Example 2

In this study, formulation development included (a) buffer evaluation (histidine, citrate, and glycyl-glycine buffers, pH 6-7) and (b) combination evaluation (bulking agents trehalose and sucrose; and stabilizers proline, glycine; EDTA to enhance enzyme activity). The evaluation of formulations used a rapid lyophilization cycle (FAST LYO cycle; freezing followed by secondary drying).

Table E5 below provides a summary of the formulations tested for buffer evaluation. Also provided are certain pre-lyophilization characteristics. The pre-lyophilization liquid samples were evaluated after dialysis for RALS (Right Angle Light Scattering) and concentration, and also for RALS in combination with an acute temperature ramp.

TABLE E5

| Buffer | pH | % Recovery based on A280 Concentration | Appearance | RALS |
|---|---|---|---|---|
| 20 mM Phosphate, 130 mM NaCl | 6.75 | N/A | Clear | 1.451 |
| 20 mM Histidine | 5.99 | 93 | Clear | 2.519 |
| 20 mM Histidine | 6.42 | 93 | Clear | 2.555 |
| 20 mM Histidine | 6.92 | 100 | Clear | 2.823 |
| 20 mM Sodium citrate | 6.15 | 89 | Clear | 4.534 |
| 20 mM Sodium citrate | 6.68 | 97 | Clear | 3.662 |
| 20 mM Glycyl-Glycine | 6.71 | 88 | Clear | 1.859 |
| 20 mM Glycyl-Glycine | 7.05 | 93 | Clear | 2.025 |

The results of percentage recovery were relatively high and all formulations remained clear after dialysis, indicating no buffer incompatibility issues. The values of RALS were higher for the citrate-containing formulations which could indicate soluble aggregates.

Lyophilization was then performed after dialysis using Formatch's FAST LYO cycle in an SP Durastop lyophilizer. A FAST LYO cycle was performed without a primary drying cycle; instead, samples were dried using only a secondary drying cycle. Lyophilization cycle used to evaluate the buffer selection was: freeze at −50° C. for 2 hours (2° C./min); dry at 22° C. for 4 hours at 60 mtorr (all ramping at 2° C./min).

All lyophilized buffer formulations from Table E5 were evaluated using RALS and IF (Intrinsic Fluorescence). Both techniques were used to evaluate the heat stability in different formulations. Samples were heated from 20° C. to 90° C. This temperature scan revealed the Tm, the temperature where a sharp change occurred, reflecting heat-induced denaturation or unfolding of the protein. The protein was considered more stable if higher Tm values were detected.

The transition temperature was observed to be ~60° C. for both RALS and IF for all liquid control formulations at T(0). The post-dialysis liquid formulations were separately filtered through a 0.2 μm filter prior to lyophilization. Also, there were no significant differences between the buffer formulations. The formulations containing histidine pH 6.5 and 7.0 showed slightly better performed by RALS analysis, and the formulation containing histidine buffer with a pH value of 6.5 showed the overall lowest initial RALS readings indicating the least amount of soluble aggregates.

For the combination evaluation, a base buffer of 20 mM histidine pH 6.5 was employed. Trehalose, sucrose, and combinations thereof were evaluated as bulking agents and for their ability to provide isotonicity to the formulations. The amino acids proline and glycine were evaluated as stabilizers. Additionally, EDTA was evaluated as a chelator. Table E6 below provides a summary of the formulations tested for combination evaluation.

TABLE E6

| Formulation ID | Composition | Bulking Agent | Stabilizer | Osmolality (mOsmol/kg) |
|---|---|---|---|---|
| F1 | 20 mM sodium phosphate 130 mM NaCl pH 6.8 | No | No | 300 |

TABLE E6-continued

| Formulation ID | Composition | Bulking Agent | Stabilizer | Osmolality (mOsmol/kg) |
|---|---|---|---|---|
| F2 | 20 mM histidine pH 6.5 | No | No | 39 |
| F3 | 20 mM histidine pH 6.5 | 9.5% trehalose | No | 325 |
| F4 | 20 mM histidine pH 6.5 | 9.5% trehalose | 20 mM proline | 332 |
| F5 | 20 mM histidine pH 6.5 | 9.5% trehalose | 20 mM glycine | 465 |
| F6 | 20 mM histidine pH 6.5 | 9.5% sucrose | No | 436 |
| F7 | 20 mM histidine pH 6.5 | 4.5% sucrose + 4.5% trehalose | No | 328 |
| F8 | 20 mM histidine pH 6.5 | 9.5% trehalose | 0.05% EDTA | 313 |

Lyophilization was performed after dialysis using Formatch's FAST LYO cycle in an SP Durastop lyophilizer. The lyophilization cycle used to evaluate the combination study is as follows: freeze at −50° C. for 2 hours; dry at 22° C. overnight at 75 mtorr (all ramping at 1° C./min). ADI-PEG 20 samples were lyophilized at 11.1 mg/mL (1 mL fill in a 10 mL vial).

The RALS temperature ramping data, RALS initial values, and enzymatic activity results suggest that a formulation containing sucrose provides an optimal stabilizing lyophilizable formulation for ADI-PEG 20. A formulation containing trehalose or both trehalose and sucrose also provides a stabilizing formulation. Additional excipients (e.g., glycine, proline, EDTA) did not significantly enhance the activity of the lyophilized formulations.

Formulations containing 9% sucrose or 9% trehalose were also evaluated by modulated differential scanning calorimetry (MDSC) to determine glass transition. The results of this analysis (a eutectic point at about −16° C. to −18° C.) suggest a primary drying temperature of −20° C. or lower should result in a non-collapsed lyophilized cake. The lyophilization cycle in Table E7 was then evaluated and showed acceptable cake appearance.

TABLE E7

| Step | Temperature | Pressure | Ramp rate | Duration for Drying |
|---|---|---|---|---|
| Freezing | −50° C. | Atmos. | 1.0° C./min | 2 hours |
| Primary Drying | −20° C. | 75 mtorr | 1.0° C./min | 22 hours + Ramp time |
| Secondary Drying | +20° C. | 200 mtorr | 1.0° C./min | 7 hours + Ramp time |

To summarize, the buffer evaluation (histidine, citrate and glycyl-glycine buffers shows that all buffers were acceptable but identified the histidine buffer (pH 6.5) as the best lyophilization buffer. The combination evaluation (bulking agents trehalose and sucrose; stabilizers proline, glycine; EDTA to enhance enzymatic activity) indicated that formulations containing sucrose showed the best overall results. However, the formulation containing trehalose and combined sucrose/trehalose also performed well. Enzyme activity results for all buffers showed greater than 90% recovery after lyophilization and greater than 80% recovery after accelerated stability (5 days incubation at 50° C.) compared to the corresponding liquid controls. Reconstitution time for all buffers was less than 1 minute and all cakes showed 100% purity by size-exclusion chromatography.

Example 3

In this study, two different lyophilization cycles were evaluated with each of three different formulations of 11 mg/mL ADI-PEG 20 at a fill volume of 3.5 mL/vial. The evaluated lyophilization parameters were shelf temperature, chamber pressure, and freezing conditions during drying. Table E8 below provides a summary of the formulations tested in this study.

TABLE E8

| Formulation ID | Buffer | Bulking Agent | Stabilizer | pH | Surfactant |
|---|---|---|---|---|---|
| 1 | 10 mM histidine | 1.9% Glycine | 1% Trehalose | 6.8 | 0.01% P20 |
| 2 | 10 mM histidine | 8.5% sucrose | 1% Trehalose | 6.8 | No |
| 3 | 10 mM histidine | 9.0% sucrose | No | 6.8 | No |

As noted above, two different lyophilization cycles were tested: an aggressive cycle (Lyophilization Cycle 1) and an intermediate cycle (Lyophilization Cycle 2).

The parameters for Lyophilization Cycle 1 are summarized in Table E9 below.

TABLE E9

Lyophilization Cycle 1.

| Step | Temperature | Time | Ramp rate | Chamber pressure |
|---|---|---|---|---|
| Loading | 5° C. | N/A | N/A | N/A |
| Freezing | 5° C. to −50° C. | N/A | 1° C./min | N/A |
|  | −50° C. | 2 hours | N/A | N/A |
| Annealing | −50° C. to −20° C. | N/A | 1° C./min | N/A |
|  | −20° C. | 2 hours | N/A | N/A |
| Primary drying | −20° C. | 1 hour | N/A | 100 mTorr |
|  | −20° C. to 20° C. | N/A | 1° C./min | 100 mTorr |
|  | 20° C. | 22.5 hours | N/A | 100 mTorr |
| Secondary drying | 20° C. to 30° C. | N/A | 1° C./min | 100 mTorr |
|  | 30° C. | 10 hours | N/A | 100 mTorr |

Upon completing Cycle 1, the resulting lyophiles were analyzed. After reconstitution with 3.5 mL of water Formulation ID 1 was visibly cloudy, whereas Formulation IDs 2 and 3 were clear and without particles.

Fourier Transform Infrared Spectroscopy (FTIR), differential scanning calorimetry (DSC), and SDS-PAGE analyses were performed on the lyophilized and reconstituted products from Cycle 1. Some structure changes in β-sheet (1630 cm-1) were observed in Formulation IDs 2 and 3 upon drying, but the structure of ADI-PEG 20 returned to its original state for these two formulations following reconstitution. Major structural changes were detected for Formulation ID 1 upon drying. After reconstitution, the structure of ADI-PEG 20 in this formulation appeared similar, but not identical to the pre-lyophilization sample. SDS-PAGE analysis showed no degradation peaks in any of the formulations.

To moderate the rate of sublimation between conservative and aggressive cycles, a shelf temperature of 0° C. was designed for primary drying in Lyophilization Cycle 2. The parameters for the intermediate Lyophilization Cycle 2 are summarized in Table E10 below.

TABLE E10

Lyophilization Cycle 2.

| Step | Temperature | Time | Ramp rate | Chamber pressure |
|---|---|---|---|---|
| Loading | 5° C. | N/A | N/A | N/A |
| Freezing | 5° C. to −50° C. | N/A | 1° C./min | N/A |
|  | −50° C. | 2 hours | N/A | N/A |
| Annealing | −50° C. to −20° C. | N/A | 1° C./min | N/A |
|  | −20° C. | 2 hours | N/A | N/A |

TABLE E10-continued

Lyophilization Cycle 2.

| Step | Temperature | Time | Ramp rate | Chamber pressure |
|---|---|---|---|---|
| Primary drying | −20° C. | 0.5 hour | N/A | 100 mTorr |
|  | −20° C. to 0° C. | N/A | 1° C./min | 100 mTorr |
|  | 0° C. | 17.5 hours | N/A | 100 mTorr |
| Secondary drying | 0° C. to 25° C. | N/A | 1° C./min | 50 mTorr |
|  | 25° C. | 10 hours | N/A | 50 mTorr |

Upon completing Cycle 2, the resulting lyophiles were analyzed. After reconstitution with 3.5 mL of water Formulation ID 1 was visibly turbid, while Formulation IDs 2 and 3 were clear and colorless.

FTIR, DSC, and SDS-PAGE analyses were performed on the lyophilized and reconstituted products from Lyophilization Cycle 2. Some structure changes in β-sheet (1630 cm-1) were observed in Formulation IDs 2 and 3 upon drying, but the structure of ADI-PEG 20 returned to its original state for these two formulations following reconstitution. Significant changes in structure were also detected for Formulation ID 1 upon drying. After reconstitution, the structure of ADI-PEG 20 in this formulation was similar to the structure prior to lyophilization. SDS-PAGE analysis showed no degradation peaks in any of the formulations.

Lyophilization Cycle 2 was performed again to confirm its robustness as an optimized drying cycle. Only the Formulations 2 and 3 were dried in this follow-up lyophilization cycle. Reconstituted samples of Formulation IDs 2 and 3 were examined by SDS-PAGE for physical degradation. No degradation products were observed for the reconstituted samples when the results were compared to the liquid drug substance and the pre-lyophilization samples.

To summarize, this study evaluated aggressive and intermediate lyophilization cycles with three the different formulations of ADI-PEG 20. Following each cycle, samples were analyzed for cake appearance, moisture content, turbidity, changes in secondary structure, physical stability and via DSC. Formulation ID 1 (w/glycine) showed signs of precipitation upon reconstitution following cycles 1 and 2, and was excluded from the confirmatory lyophilization cycle. Conversely, the integrity of the Formulation IDs 2 and 3 containing sucrose was well maintained following each tested lyophilization cycle. Any changes in the structure after drying were reversible upon reconstitution.

Example 4

In this study, two different PEG-numbered ADI-PEG 20 preparations were evaluated under two different storage temperatures. The stability parameters that were evaluated include appearance before and after reconstitution, enzyme activity, and PEG number. Table E1 below provides a summary of the PEG number and formulation tested in this study.

TABLE E11

| Form ID | PEG number | Composition/Buffer | Bulking Agent | Stabilizer | Plasticizer | Surfactant | Chelator |
|---|---|---|---|---|---|---|---|
| P204 | High (5) | 150 mM sodium phosphate pH 6.8 | 4.5% Sucrose 4.5% Trehalose | 0.5% Glycine | 0.25% Glycerol | 0.01% Tween 80 | 0.05% EDTA |
| C204 | Low (2) | 150 mM sodium phosphate pH 6.8 | 4.5% Sucrose 4.5% Trehalose | 0.5% Glycine | 0.25% Glycerol | 0.01% Tween 80 | 0.05% EDTA |

The lyophilization process was as follows. Samples were frozen to make sure the entire formulation was in its solid phase. Then, each vial of sample was freeze dried using a Virtis Freeze Mobile 25 EL at −78° C. to −85° C. and 50-120 mTorr for approximately 24 hours to allow as much water as possible to sublime.

As mentioned previously, the storage temperature for each of these lyophilized products was either at 2-8° C. or room temperature. The two storage temperatures and storage duration are listed in Table E12 below.

TABLE E12

Storage Conditions.

| Temperature | Duration | | |
|---|---|---|---|
|  | 0 months | 1 months | 3 months |
| 2-8° C. | N/A | N/A | X |
| Room Temperature | X | X | X |

Upon lyophilization and storage at the respective temperatures, the lyophiles were analyzed. After lyophilization, the appearance of the product was a white and fluffy cake. After reconstitution with water, both Formulation ID P204 and C204 were clear and particle free. The reconstitution time for each of P204 and C204 was less than 1 minute.

Enzyme activity, reverse phase (RP) chromatography, and SDS-PAGE analyses were performed on the lyophilized and reconstituted products. As shown below in Table E13, storage of lyophiles at 2-8° C. resulted in greater retention of ADI enzyme activity relative to storage at room temperature storage. For example, P204 retained about 92% of its ADI enzyme activity after storage at 2-8° C. for 3 months, and about 86% of its activity after storage at room temperature for 3 months (relative to 0 month timepoint). C204 retained about 96% of its ADI enzyme activity after storage at 2-8° C. for 3 months, and about 74% of its enzyme activity after storage at room temperature for 3 months (relative to 0 month timepoint).

TABLE E13

Lyophilized/Reconstituted Product Enzyme Activity (IU/mg)

|  | P204 | | | C204 | | |
| --- | --- | --- | --- | --- | --- | --- |
|  | Time | | | | | |
| Temperature | 0 mon | 1 mon | 3 mons | 0 mon | 1 mon | 3 mons |
| 2-8° C. | N/A | N/A | 22.4 (92%) | N/A | N/A | 68.3 (96%) |
| Room Temperature | 24.3 (100%) | 21.2 (87%) | 20.8 (86%) | 70.9 (100%) | 61.3 (86%) | 52.2 (74%) |

RP chromatography was used to analyze PEG number. The number of PEG(s) per protomer before and after lyophilization and reconstitution did not change significantly as shown below in Table E14. The lyophilization process and storage did not result in any decoupling of PEG. SDS-PAGE analysis also showed no significant change in the number of PEG(s) per ADI protomer.

TABLE E14

Lyophilized/Reconstituted PEG(s) Number per Protomer

|  | P204 | | | C204 | | |
| --- | --- | --- | --- | --- | --- | --- |
|  | Time | | | | | |
| Temperature | 0 mon | 1 mon | 3 mons | 0 mon | 1 mon | 3 mons |
| 2-8° C. | N/A | N/A | 4.64 (100.2%) | N/A | N/A | 1.32 (86%) |
| Room Temperature | 4.63 (100%) | 4.62 (99.8%) | 4.57 (98.7%) | 1.53 (100%) | 1.49 (97.4%) | 1.53 (100%) |

Each of P204 and C204 were clear and free of particles after reconstitution with solvent, and reconstitution occurred in less than 1 minute. Moreover, for each of P204 and C204, the loss of ADI enzyme activity that occurred after storage at room temperature was greater than that observed after storage at 2-8° C. Furthermore, for both storage temperatures, the number of PEGs per ADI protomer remained unaltered.

Example 5

Studies were performed to evaluate the storage conditions of ADI-PEG 20 formulation consisting of ADI covalently bonded with PEG by a water-labile linker. The storage conditions were 2-8° C. for up to 28 months. The stability parameters that were evaluated include appearance, PEG number, free PEG, and ADI enzyme activity. Table E12 below provides a summary of the formulation tested in this study.

TABLE E12

| Formulation ID | Composition/Buffer | pH |
| --- | --- | --- |
| HS | 130 mM sodium chloride, 35 mM Histidine buffer | 6.8 |

Upon lyophilization and storage at the evaluated condition, the Formulation ID HS was analyzed. After lyophilization and storage at 2-8° C. for 28 months, the appearance of the formulation was a uniform well-packed white cake with no gross melt-back. After reconstitution with water for lyophilized product stored for 28 months, the Formulation ID HS was clear and particle free. The reconstitution time was about 40 seconds.

Evaluation of enzyme activity was conducted on the lyophilized product stored at 2-8° C. and compared with the activity for product that was stored frozen at −70° C. Enzyme activity was fully retained when storing the lyophile at 2-8° C. for 28 months. Results are shown below in Table E13.

TABLE E13

Lyophilized Product Enzyme Activity (IU/mg)

|  | Control frozen product stored at −70° C. | Formulation ID HS stored at 2-8° C. For 28 months | |
| --- | --- | --- | --- |
| Storage condition | 6.0 | 6.3 | 105% remaining |

RP chromatography and SEC chromatography were used to analyze PEG number and free PEG concentration (mg/mL), respectively. The number of PEG(s) per protomer and free PEG before and after lyophilization and after 28 months of storage at 2-8° C. did not change significantly as is shown below in Table E14. It is obvious that the lyophilization process and up to 28 months of storage did not result in decoupling of PEG from the enzyme.

TABLE E14

Lyophilized product PEG(s) Number per Monomer and free PEG

| Sample tested | PEG/Monomer | Free PEG (mg/mL) |
| --- | --- | --- |
| Control | 5.33 | 0.2 |
| Formulation ID HS | 5.51 | 0.1 |

In summary, formulation HS was clear and free of particles after reconstitution with solvent and reconstitution occurred in less than 1 minute. In addition, this study also shows that the decoupling of covalently attached PEG does not occur during storage and the enzyme is fully active upon reconstitution. ADI covalently linked with a water labile PEG before and after lyophilization, and reconstitution in the storage condition of 2-8° C. was stable for at least 28 months.

The invention claimed is:

1. A lyophilized formulation, comprising pegylated arginine deiminase (ADI-PEG), wherein the lyophilized formulation is sterile, substantially endotoxin-free, and at a pharmaceutically-acceptable pH, a histidine buffer at a concentration of about 1 to about 50 mM, sodium chloride at about 100 to about 150 mM, and sucrose at about 1 wt % to about 20 wt %, and wherein the ADI-PEG retains at least 85%, 90% or 95% arginine deiminase (ADI) activity relative to a corresponding ADI-PEG in a non-lyophilized liquid control composition and wherein the arginine deiminase is covalently bonded to about 1 to about 21 PEG molecules.

2. The lyophilized formulation of claim 1, wherein the histidine buffer is at about 10, 20, 25, 30, 35 or 40 mM, and wherein the sodium chloride is at about 120, 130, or 140 mM.

3. The lyophilized formulation of claim 2, comprising sucrose at about 1% to about 10%.

4. The lyophilized formulation of claim 3, wherein the pH is about 6.0 to about 7.2±0.1.

5. The lyophilized formulation of claim 4, comprising a histidine buffer at about 35 mM, sodium chloride at about 130 mM, and sucrose at about 5 wt % wherein the pH is about 6.8±0.1.

6. The lyophilized formulation of claim 1, wherein the dry weight of the ADI-PEG is about 50 to about 150 mg/g.

7. The lyophilized formulation of claim 1, wherein the ADI-PEG comprises an amino acid sequence that is at least 80, 95, 90, 95, 96, 97, 98, 99, or 100% identical to a sequence selected from SEQ ID NOs: 1-56.

8. The lyophilized formulation of claim 1, wherein the ADI-PEG comprises one or more water-labile linkers which covalently attach the ADI and PEG.

9. The lyophilized formulation of claim 1, wherein the ADI-PEG retains at least 75, 80, 85, 90, 95, or 100% of the original PEG molecules per ADI monomer or protomer, optionally relative to a corresponding ADI-PEG in a non-lyophilized liquid control composition.

10. The lyophilized formulation of claim 3, wherein the pH is about 6.5 to about 7.2±0.1.

11. A patient care kit comprising a lyophilized formulation of claim 1, and optionally a pharmaceutically acceptable solvent.

12. The patient care kit of claim 11, wherein the solvent is water.

13. A method of reconstituting a lyophilized formulation of claim 1, comprising adding a pharmaceutically acceptable solvent to the lyophilized formulation to form a reconstituted liquid composition.

14. The method of claim 13, wherein the lyophilized formulation is reconstituted to a substantially aggregate-free solution of about 5-20 mg/ml ADI-PEG in a time of less than about five minutes.

15. The method of claim 14, wherein the lyophilized formulation is reconstituted to a substantially aggregate-free solution of about 5-20 mg/ml ADI-PEG in a time of less than about one or two minutes.

16. The method of claim 13, wherein the ADI-PEG in the reconstituted liquid composition retains at least 85, 90, or 95% of its arginine deiminase (ADI) activity, or wherein the ADI-PEG in the reconstituted liquid composition retains at least 50, 55, 60, 65, 70, 75, 80, 85, 90, 95, or 100% of the original PEG molecules per ADI monomer/protomer, optionally relative to a corresponding ADI-PEG in a non-lyophilized liquid control composition.

17. The method of claim 13, wherein the ADI-PEG in the reconstituted liquid composition retains at least 85, 90, or 95% of its ADI activity upon reconstitution, or wherein the ADI-PEG in the reconstituted liquid composition retains at least 50, 55, 60, 65, 70, 75, 80, 85, 90, 95, or 100% of the PEG molecules per ADI monomer/protomer, after being stored as a lyophilized formulation for about or at least about 1, 2, 3, or 4 weeks, or about or at least about 1, 2, 3, 4, 5, 6, 7, 8, 9, 10, 11, 12, 13, 14, 15, 16, 17, 18, 19, 20, 21, 22, 23, 24, 36, 48, 60, or 72 months, optionally after being stored at a temperature of about 2-8° C. and/or about room temperature.

18. The method of claim 13, wherein the specific ADI enzyme activity of the ADI-PEG is about 5.0 to about 120 IU/mg, or about 5.5, 6, 6.5, 7, 7.5, 8, 8.5, 9.0, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 35, 40, 45, 50, 55, 60, 65, 70, 75, 80, 85, 90, 95, 100, 105, 110, 115, or 120 IU/mg.

19. The method of claim 13, wherein the ADI-PEG has an osmolality of about 50 mOsm/kg to about 500 mOsm/kg, or about 50, 55, 60, 65, 70, 75, 80, 85, 90, 95, 100, 105, 110, 120, 125, 130, 135, 140, 145, 150, 155, 160, 165, 170, 175, 180, 185, 190, 195, 200, 205, 210, 220, 225, 230, 235, 240, 245, 250, 255, 260, 265, 270, 275, 280, 285, 290, 295, 300, 305, 310, 320, 325, 330, 335, 340, 345, 350, 355, 360, 365, 370, 375, 380, 385, 390, 395, 400, 405, 410, 420, 425, 430, 435, 440, 445, 450, 455, 460, 465, 470, 475, 480, 485, 490, 495, or about 500 mOsm/kg.

20. The method of claim 13, wherein the solvent is water.

* * * * *

SEQUENCE LISTING

<160> NUMBER OF SEQ ID NOS: 56

<210> SEQ ID NO 1
<211> LENGTH: 409
<212> TYPE: PRT
<213> ORGANISM: Mycoplasma hominis

<400> SEQUENCE: 1

```
Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Gln Ser Phe Val Lys Ile
    50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95

Thr Phe Leu Glu Glu Thr Val Pro Val Leu Thr Glu Ala Asn Lys Lys
            100                 105                 110

Ala Val Arg Ala Phe Leu Leu Ser Lys Pro Thr His Glu Met Val Glu
            115                 120                 125

Phe Met Met Ser Gly Ile Thr Lys Tyr Glu Leu Gly Val Glu Ser Glu
    130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
            195                 200                 205

Met Pro Ile Glu Gly Gly Asp Val Phe Ile Tyr Asn Asn Glu Thr Leu
210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
            245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
    275                 280                 285

Asp Val Phe Lys Phe Trp Asp Tyr Asp Leu Val Asn Gly Gly Ala Glu
    290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
            325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
            355                 360                 365

Thr Asn Ala Ala Leu Lys Ala Ala Gly Ile Thr Val Leu Pro Phe His
    370                 375                 380

Gly Asn Gln Leu Ser Leu Gly Met Gly Asn Ala Arg Cys Met Ser Met
385                 390                 395                 400

Pro Leu Ser Arg Lys Asp Val Lys Trp
                405
```

-continued

```
<210> SEQ ID NO 2
<211> LENGTH: 409
<212> TYPE: PRT
<213> ORGANISM: Artificial Sequence
<220> FEATURE:
<223> OTHER INFORMATION: Mutated arginine deaminase

<400> SEQUENCE: 2

Met Ser Val Phe Asp Ser Lys Phe Asn Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Gln Ser Phe Val Lys Ile
    50                  55                  60

Met Lys Asp Arg Gly Ile Asn Val Val Glu Leu Thr Asp Leu Val Ala
65                  70                  75                  80

Glu Thr Tyr Asp Leu Ala Ser Lys Ala Ala Lys Glu Glu Phe Ile Glu
                85                  90                  95

Thr Phe Leu Glu Glu Thr Val Pro Val Leu Thr Glu Ala Asn Lys Glu
            100                 105                 110

Ala Val Arg Ala Phe Leu Leu Ser Lys Pro Thr His Glu Met Val Glu
        115                 120                 125

Phe Met Met Ser Gly Ile Thr Lys Tyr Glu Leu Gly Val Glu Ser Glu
130                 135                 140

Asn Glu Leu Ile Val Asp Pro Met Pro Asn Leu Tyr Phe Thr Arg Asp
145                 150                 155                 160

Pro Phe Ala Ser Val Gly Asn Gly Val Thr Ile His Phe Met Arg Tyr
                165                 170                 175

Ile Val Arg Arg Arg Glu Thr Leu Phe Ala Arg Phe Val Phe Arg Asn
            180                 185                 190

His Pro Lys Leu Val Lys Thr Pro Trp Tyr Tyr Asp Pro Ala Met Lys
        195                 200                 205

Met Ser Ile Glu Gly Gly Asp Val Phe Ile Tyr Asn Asn Glu Thr Leu
210                 215                 220

Val Val Gly Val Ser Glu Arg Thr Asp Leu Asp Thr Ile Thr Leu Leu
225                 230                 235                 240

Ala Lys Asn Ile Lys Ala Asn Lys Glu Val Glu Phe Lys Arg Ile Val
                245                 250                 255

Ala Ile Asn Val Pro Lys Trp Thr Asn Leu Met His Leu Asp Thr Trp
            260                 265                 270

Leu Thr Met Leu Asp Lys Asn Lys Phe Leu Tyr Ser Pro Ile Ala Asn
        275                 280                 285

Asp Val Phe Lys Phe Trp Asp Tyr Asp Leu Val Asn Gly Gly Ala Glu
290                 295                 300

Pro Gln Pro Gln Leu Asn Gly Leu Pro Leu Asp Lys Leu Leu Ala Ser
305                 310                 315                 320

Ile Ile Asn Lys Glu Pro Val Leu Ile Pro Ile Gly Gly Ala Gly Ala
                325                 330                 335

Thr Glu Met Glu Ile Ala Arg Glu Thr Asn Phe Asp Gly Thr Asn Tyr
            340                 345                 350

Leu Ala Ile Lys Pro Gly Leu Val Ile Gly Tyr Asp Arg Asn Glu Lys
        355                 360                 365

Thr Asn Ala Ala Leu Lys Ala Ala Gly Ile Thr Val Leu Pro Phe His
```

```
                    370                 375                 380
Gly Asn Gln Leu Ser Leu Gly Met Gly Asn Ala Arg Cys Met Ser Met
385                 390                 395                 400

Pro Leu Ser Arg Lys Asp Val Lys Trp
                405
```

<210> SEQ ID NO 3
<211> LENGTH: 392
<212> TYPE: PRT
<213> ORGANISM: Mycoplasma phocicerebrale

<400> SEQUENCE: 3

```
Ile His Val Tyr Ser Glu Ile Gly Glu Leu Glu Thr Val Leu Val His
1               5                   10                  15

Glu Pro Gly Arg Glu Ile Asp Tyr Ile Thr Pro Ala Arg Leu Asp Glu
                20                  25                  30

Leu Leu Phe Ser Ala Ile Leu Glu Ser His Asp Ala Arg Lys Glu His
            35                  40                  45

Gln Ser Phe Val Lys Gln Leu Lys Asp Asn Gly Ile Asn Val Val Glu
        50                  55                  60

Leu Thr Asp Leu Val Ala Glu Thr Phe Asp Leu Ala Ser Lys Glu Glu
65                  70                  75                  80

Gln Glu Lys Leu Ile Glu Glu Phe Leu Glu Asp Ser Glu Pro Val Leu
                85                  90                  95

Ser Glu Ala His Lys Thr Ala Val Arg Lys Phe Leu Thr Ser Arg Lys
                100                 105                 110

Ser Thr Arg Glu Met Val Glu Phe Met Met Ala Gly Ile Thr Lys Tyr
            115                 120                 125

Asp Leu Gly Ile Glu Ala Asp His Glu Leu Ile Val Asp Pro Met Pro
130                 135                 140

Asn Leu Tyr Phe Thr Arg Asp Pro Phe Ala Ser Val Gly Asn Gly Val
145                 150                 155                 160

Thr Ile His Tyr Met Arg Tyr Lys Val Arg Gln Arg Glu Thr Leu Phe
                165                 170                 175

Ser Arg Phe Val Phe Ser Asn His Pro Lys Leu Val Lys Thr Pro Trp
            180                 185                 190

Tyr Tyr Asp Pro Ala Met Lys Met Ser Ile Glu Gly Gly Asp Val Phe
        195                 200                 205

Ile Tyr Asn Asn Asp Thr Leu Val Gly Val Ser Glu Arg Thr Asp
    210                 215                 220

Leu Glu Thr Ile Thr Leu Leu Ala Lys Asn Ile Lys Ala Asn Lys Glu
225                 230                 235                 240

Val Glu Phe Lys Arg Ile Val Ala Ile Asn Val Pro Lys Trp Thr Asn
                245                 250                 255

Leu Met His Leu Asp Thr Trp Leu Thr Met Leu Asp Lys Asp Lys Phe
            260                 265                 270

Leu Tyr Ser Pro Ile Ala Asn Asp Val Phe Lys Phe Trp Asp Tyr Asp
        275                 280                 285

Leu Val Asn Gly Gly Ala Glu Pro Gln Pro Lys Glu Asn Gly Leu Pro
    290                 295                 300

Leu Glu Gly Leu Leu Gln Ser Ile Ile Asn Lys Lys Pro Val Leu Ile
305                 310                 315                 320

Pro Ile Ala Gly Asn Asn Ala Ser His Ile Asp Ile Glu Arg Glu Thr
                325                 330                 335
```

His Phe Asp Gly Thr Asn Tyr Leu Ala Ile Lys Pro Gly Val Val Ile
                340                 345                 350

Gly Tyr Ala Arg Asn Glu Lys Thr Asn Ala Ala Leu Ala Ala Ala Gly
                355                 360                 365

Ile Lys Val Leu Pro Phe His Gly Asn Gln Leu Ser Leu Gly Met Gly
            370                 375                 380

Asn Ala Arg Cys Met Ser Met Pro
385                 390

<210> SEQ ID NO 4
<211> LENGTH: 410
<212> TYPE: PRT
<213> ORGANISM: Mycoplasma arginini

<400> SEQUENCE: 4

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Gln Phe Val Ala Glu
50                  55                  60

Leu Lys Ala Asn Asp Ile Asn Val Val Glu Leu Ile Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu His Lys Val
            100                 105                 110

Val Val Arg Asn Phe Leu Lys Ala Lys Lys Thr Ser Arg Glu Leu Val
        115                 120                 125

Glu Ile Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Ile Asn Thr Pro Trp Tyr Tyr Asp Pro Ser Leu
        195                 200                 205

Lys Leu Ser Ile Glu Gly Gly Asp Val Phe Ile Tyr Asn Asn Asp Thr
210                 215                 220

Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
290                 295                 300

Glu Pro Gln Pro Val Glu Asn Gly Leu Pro Leu Glu Gly Leu Leu Gln
305                 310                 315                 320

```
Ser Ile Ile Asn Lys Lys Pro Val Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
    370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 5
<211> LENGTH: 409
<212> TYPE: PRT
<213> ORGANISM: Mycoplasma arthritidis

<400> SEQUENCE: 5

Met Ser Val Phe Asp Ser Lys Phe Lys Gly Ile His Val Tyr Ser Glu
1               5                   10                  15

Ile Gly Glu Leu Glu Thr Val Leu Val His Glu Pro Gly Lys Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Lys Glu His Lys Glu Phe Val Ala Glu
    50                  55                  60

Leu Lys Lys Arg Gly Ile Asn Val Val Glu Leu Val Asp Leu Ile Val
65                  70                  75                  80

Glu Thr Tyr Asp Leu Ala Ser Lys Glu Ala Lys Glu Lys Leu Leu Glu
                85                  90                  95

Glu Phe Leu Asp Asp Ser Val Pro Val Leu Ser Asp Glu His Arg Ala
            100                 105                 110

Ala Val Lys Lys Phe Leu Gln Ser Gln Lys Ser Thr Arg Ser Leu Val
        115                 120                 125

Glu Tyr Met Ile Ala Gly Ile Thr Lys His Asp Leu Lys Ile Glu Ser
    130                 135                 140

Asp Leu Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ala Glu
        195                 200                 205

Gly Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
```

```
            275                 280                 285
Asn Asp Val Phe Lys Phe Trp Asp Tyr Asp Leu Val Asn Gly Gly Asp
290                 295                 300

Ala Pro Gln Pro Val Asp Asn Gly Leu Pro Leu Glu Asp Leu Leu Lys
305                 310                 315                 320

Ser Ile Ile Gly Lys Pro Thr Leu Ile Pro Ile Ala Gly Ala Gly
                325                 330                 335

Ala Ser Gln Ile Asp Ile Glu Arg Glu Thr His Phe Asp Gly Thr Asn
                340                 345                 350

Tyr Leu Ala Val Ala Pro Gly Ile Val Ile Gly Tyr Ala Arg Asn Glu
                355                 360                 365

Lys Thr Asn Ala Ala Leu Glu Ala Ala Gly Ile Thr Val Leu Pro Phe
370                 375                 380

Arg Gly Asn Gln Leu Ser Leu Gly Met Gly Asn Ala Arg Cys Met Ser
385                 390                 395                 400

Met Pro Leu Ser Arg Lys Asp Val Lys
                405

<210> SEQ ID NO 6
<211> LENGTH: 408
<212> TYPE: PRT
<213> ORGANISM: Mycoplasma orale
<220> FEATURE:
<221> NAME/KEY: misc_feature
<222> LOCATION: (201)..(201)
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (272)..(272)
<223> OTHER INFORMATION: Xaa can be any naturally occurring amino acid
<220> FEATURE:
<221> NAME/KEY: misc_feature
<222> LOCATION: (294)..(294)
<223> OTHER INFORMATION: Xaa can be any naturally occurring amino acid

<400> SEQUENCE: 6

Ser Val Phe Ser Asp Lys Phe Asn Gly Ile His Val Tyr Ser Glu Ile
1               5                   10                  15

Gly Asp Leu Glu Ser Val Leu Val His Glu Pro Gly Lys Glu Ile Asp
                20                  25                  30

Tyr Ile Thr Pro Ala Arg Leu Asp Glu Leu Leu Phe Ser Ala Ile Leu
                35                  40                  45

Glu Ser Thr Asp Ala Arg Lys Glu His Lys Glu Phe Val Glu Ile Leu
50                  55                  60

Lys Lys Gln Gly Ile Asn Val Val Glu Leu Val Asp Leu Val Val Glu
65                  70                  75                  80

Thr Tyr Asn Leu Val Asp Lys Lys Thr Gln Glu Lys Leu Leu Lys Asp
                85                  90                  95

Phe Leu Asp Asp Ser Glu Pro Val Leu Ser Pro Glu His Arg Lys Ala
                100                 105                 110

Val Glu Lys Phe Leu Lys Ser Leu Lys Ser Thr Lys Glu Leu Ile Gln
                115                 120                 125

Tyr Met Met Ala Gly Ile Thr Lys Tyr Asp Leu Gly Ile Lys Ala Asp
                130                 135                 140

Lys Glu Leu Ile Val Asp Pro Met Pro Asn Leu Tyr Phe Thr Arg Asp
145                 150                 155                 160
```

Pro Phe Ala Ser Val Gly Asn Gly Val Thr Ile His Tyr Met Arg Tyr
                165                 170                 175

Lys Val Arg Gln Arg Glu Thr Leu Phe Ser Lys Phe Ile Phe Thr Asn
            180                 185                 190

His Pro Lys Leu Val Lys Thr Pro Xaa Tyr Tyr Asp Pro Ala Met Lys
        195                 200                 205

Leu Ser Ile Glu Gly Gly Asp Val Phe Ile Tyr Asn Asn Asp Thr Leu
    210                 215                 220

Val Val Gly Val Ser Glu Arg Thr Asp Leu Glu Thr Ile Thr Leu Leu
225                 230                 235                 240

Ala Lys Asn Ile Lys Ala Asn Lys Glu Cys Glu Phe Lys Arg Ile Val
                245                 250                 255

Ala Ile Asn Val Pro Lys Xaa Thr Asn Leu Met His Leu Asp Thr Xaa
            260                 265                 270

Leu Thr Met Leu Asp Lys Asp Lys Phe Leu Tyr Ser Pro Ile Ala Asn
        275                 280                 285

Asp Val Phe Lys Phe Xaa Asp Tyr Asp Leu Val Asn Gly Gly Ser Asn
    290                 295                 300

Pro Glu Pro Val Val Asn Gly Leu Pro Leu Asp Lys Leu Leu Glu Ser
305                 310                 315                 320

Ile Ile Asn Lys Lys Pro Val Leu Ile Pro Ile Ala Gly Lys Gly Ala
                325                 330                 335

Thr Glu Ile Glu Thr Ala Val Glu Thr His Phe Asp Gly Thr Asn Tyr
            340                 345                 350

Leu Ala Ile Lys Pro Gly Val Val Gly Tyr Ser Arg Asn Val Lys
        355                 360                 365

Thr Asn Ala Ala Leu Glu Ala Asn Gly Ile Lys Val Leu Pro Phe Lys
    370                 375                 380

Gly Asn Gln Leu Ser Leu Gly Met Gly Asn Ala Arg Cys Met Ser Met
385                 390                 395                 400

Pro Leu Ser Arg Lys Asp Val Lys
                405

<210> SEQ ID NO 7
<211> LENGTH: 391
<212> TYPE: PRT
<213> ORGANISM: Mycoplasma gateae

<400> SEQUENCE: 7

Ile His Val Tyr Ser Glu Ile Gly Glu Leu Glu Ser Val Leu Val His
1               5                   10                  15

Glu Pro Gly Arg Glu Ile Asp Tyr Ile Thr Pro Ala Arg Leu Asp Glu
            20                  25                  30

Leu Leu Phe Ser Ala Ile Leu Glu Ser His Asp Ala Arg Lys Glu His
        35                  40                  45

Lys Leu Phe Val Ser Glu Leu Lys Ala Asn Asp Ile Asn Val Val Glu
    50                  55                  60

Leu Thr Asp Leu Val Thr Glu Thr Tyr Asp Leu Ala Ser Gln Glu Ala
65                  70                  75                  80

Lys Asp Asn Leu Ile Glu Glu Phe Leu Glu Asp Ser Glu Pro Val Leu
                85                  90                  95

Thr Glu Glu Leu Lys Ser Val Val Arg Thr Tyr Leu Lys Ser Ile Lys
            100                 105                 110

Ser Thr Arg Glu Leu Ile Gln Met Met Met Ala Gly Ile Thr Lys Tyr

-continued

```
            115                 120                 125
Asp Leu Gly Ile Glu Ala Asp His Glu Leu Ile Val Asp Pro Met Pro
    130                 135                 140

Asn Leu Tyr Phe Thr Arg Asp Pro Phe Ala Ser Val Gly Asn Gly Val
145                 150                 155                 160

Thr Ile His Tyr Met Arg Tyr Lys Val Arg Gln Arg Glu Thr Leu Phe
                165                 170                 175

Ser Arg Phe Val Phe Ser Asn His Pro Lys Leu Val Asn Thr Pro Trp
            180                 185                 190

Tyr Tyr Asp Pro Ser Leu Lys Leu Ser Ile Glu Gly Gly Asp Val Phe
        195                 200                 205

Ile Tyr Asn Asn Asn Thr Leu Val Val Gly Val Ser Glu Arg Thr Asp
    210                 215                 220

Leu Glu Thr Val Thr Leu Leu Ala Lys Asn Ile Val Ala Asn Lys Glu
225                 230                 235                 240

Cys Glu Phe Lys Arg Ile Val Ala Ile Asn Val Pro Lys Trp Thr Asn
                245                 250                 255

Leu Met His Leu Asp Thr Trp Leu Thr Met Leu Asp Lys Asp Lys Phe
            260                 265                 270

Leu Tyr Ser Pro Ile Ala Asn Asp Val Phe Lys Phe Trp Asp Tyr Asp
        275                 280                 285

Leu Val Asn Gly Gly Glu Glu Pro Gln Pro Val Glu Asn Gly Leu Pro
    290                 295                 300

Leu Glu Gly Leu Leu Glu Ser Ile Ile Asn Lys Lys Pro Ile Leu Ile
305                 310                 315                 320

Pro Ile Ala Gly Glu Gly Ala Ser Gln Ile Asp Ile Glu Arg Glu Thr
                325                 330                 335

His Phe Asp Gly Thr Asn Tyr Leu Ala Ile Arg Pro Gly Val Val Ile
            340                 345                 350

Gly Tyr Ser Arg Asn Glu Lys Thr Asn Ala Ala Leu Glu Ala Ala Gly
        355                 360                 365

Ile Lys Val Leu Pro Phe His Gly Asn Gln Leu Ser Leu Gly Met Gly
    370                 375                 380

Asn Ala Arg Cys Met Ser Met
385                 390

<210> SEQ ID NO 8
<211> LENGTH: 392
<212> TYPE: PRT
<213> ORGANISM: Mycoplasma phocidae

<400> SEQUENCE: 8

Ile His Val Tyr Ser Glu Ile Gly Glu Leu Gln Thr Val Leu Val His
1               5                   10                  15

Glu Pro Gly Arg Glu Ile Glu Tyr Ile Thr Pro Ala Arg Leu Asp Glu
                20                  25                  30

Leu Leu Phe Ser Ala Ile Leu Glu Ser His Asp Ala Arg Lys Glu His
            35                  40                  45

Gln Glu Phe Val Ala Glu Leu Lys Lys Asn Asn Ile Asn Val Val Glu
        50                  55                  60

Leu Thr Asp Leu Val Ser Glu Thr Tyr Asp Met Val Ser Lys Glu Lys
65                  70                  75                  80

Gln Glu Lys Leu Ile Glu Glu Phe Leu Glu Asp Ser Glu Pro Val Leu
                85                  90                  95
```

```
Ser Glu Glu His Lys Gly Leu Val Arg Lys Phe Leu Lys Ser Leu Lys
            100                 105                 110

Ser Ser Lys Glu Leu Ile Gln Tyr Met Met Ala Gly Ile Thr Lys His
        115                 120                 125

Asp Leu Asn Ile Glu Ala Asp His Glu Leu Ile Val Asp Pro Met Pro
    130                 135                 140

Asn Leu Tyr Phe Thr Arg Asp Pro Phe Ala Ser Val Gly Asn Gly Val
145                 150                 155                 160

Thr Ile His Tyr Met Arg Tyr Lys Val Arg Gln Arg Glu Thr Leu Phe
                165                 170                 175

Ser Arg Phe Ile Phe Ala Asn His Pro Lys Leu Met Asn Thr Pro Leu
            180                 185                 190

Tyr Tyr Asn Pro Asp Met Lys Leu Ser Ile Glu Gly Gly Asp Val Phe
        195                 200                 205

Val Tyr Asn Asn Glu Thr Leu Val Val Gly Val Ser Glu Arg Thr Asp
    210                 215                 220

Leu Asp Thr Ile Thr Leu Leu Ala Lys Asn Ile Lys Ala Asn Lys Glu
225                 230                 235                 240

Arg Glu Phe Lys Arg Ile Val Ala Ile Asn Val Pro Lys Trp Thr Asn
                245                 250                 255

Leu Met His Leu Asp Thr Trp Leu Thr Met Leu Asp Lys Asp Lys Phe
            260                 265                 270

Leu Tyr Ser Pro Ile Ala Asn Asp Val Phe Lys Phe Trp Asp Tyr Asp
        275                 280                 285

Leu Val Asn Gly Gly Asp Glu Pro Gln Pro Lys Val Asn Gly Leu Pro
    290                 295                 300

Leu Glu Lys Leu Leu Glu Ser Ile Ile Asn Lys Lys Pro Ile Leu Ile
305                 310                 315                 320

Pro Ile Ala Gly Thr Ser Ala Ser Asn Ile Asp Val Glu Arg Glu Thr
                325                 330                 335

His Phe Asp Gly Thr Asn Tyr Leu Ala Ile Ala Pro Gly Val Val Ile
            340                 345                 350

Gly Tyr Ser Arg Asn Val Lys Thr Asn Glu Ala Leu Glu Ala Ala Gly
        355                 360                 365

Ile Lys Val Leu Pro Phe Lys Gly Asn Gln Leu Ser Leu Gly Met Gly
    370                 375                 380

Asn Ala Arg Cys Met Ser Met Pro
385                 390

<210> SEQ ID NO 9
<211> LENGTH: 401
<212> TYPE: PRT
<213> ORGANISM: Mycoplasma columbinum

<400> SEQUENCE: 9

Met Ser Lys Ile Asn Val Tyr

```
Thr Gln Lys Glu Arg Glu Ala Phe Ile Glu Lys Trp Leu Asp Glu Ala
                85                  90                  95

Glu Pro Ala Leu Thr Lys Asp Leu Arg Ala Lys Val Lys Ser Tyr Val
            100                 105                 110

Leu Ser Lys Glu Gly Thr Pro Val Ala Met Val Arg Thr Met Met Ala
        115                 120                 125

Gly Val Ser Lys Gln Glu Leu Asn Val Glu Ser Glu Thr Glu Leu Val
    130                 135                 140

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Thr Arg Lys
                165                 170                 175

Arg Glu Thr Ile Phe Ala Glu Phe Ile Phe Ala Thr His Pro Asp Tyr
            180                 185                 190

Lys Thr Thr Pro His Trp Phe Asp Arg Leu Asp Glu Gly Asn Ile Glu
        195                 200                 205

Gly Gly Asp Val Phe Ile Tyr Asn Lys Asp Thr Leu Val Ile Gly Val
    210                 215                 220

Ser Glu Arg Thr Asn Lys Glu Ala Ile Leu Thr Ile Ala Lys Lys Ile
225                 230                 235                 240

Lys Asn Asn Lys Glu Ala Lys Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asp Lys Phe Leu Tyr Ser Pro Asn Met Leu Ser Val Leu Lys
        275                 280                 285

Val Trp Glu Ile Asp Leu Ser Lys Glu Ile Glu Met Val Glu Thr Asn
    290                 295                 300

Lys Pro Leu Ala Asp Val Leu Glu Ser Ile Ile Gly Val Lys Pro Val
305                 310                 315                 320

Leu Ile Pro Ile Ala Gly Lys Gly Ala Thr Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Ile Lys Thr Glu Ala Ala Leu Arg Ala
        355                 360                 365

Ala Gly Val Thr Val Leu Ser Phe Glu Gly Asn Gln Leu Ser Leu Gly
    370                 375                 380

Met Gly Ser Ala Arg Cys Met Ser Met Pro Leu Val Arg Glu Asp Val
385                 390                 395                 400

Lys

<210> SEQ ID NO 10
<211> LENGTH: 407
<212> TYPE: PRT
<213> ORGANISM: Mycoplasma iowae

<400> SEQUENCE: 10

Met Gly Asn Asn Ile Pro Lys Lys Ile Asn Val Phe Ser Glu Ile Gly
1               5                   10                  15

Asn Leu Lys Arg Val Leu Val His Thr Pro Gly Lys Glu Ile Glu Tyr
            20                  25                  30

Val Thr Pro Gln Arg Leu Asp Glu Leu Leu Phe Ser Ala Ile Leu Asp
        35                  40                  45
```

Pro Val Arg Ala Arg Glu His Lys Glu Phe Ile Lys Ile Leu Glu
            50                  55                  60

Ser Gln Gly Val Glu Val Gln Leu Val Asp Leu Thr Ala Glu Thr
 65                  70                  75                  80

Tyr Asp Val Ala Glu Ser Gln Ala Lys Glu Asn Phe Ile Gln Lys Trp
                         85                  90                  95

Leu Asp Glu Ser Leu Pro Lys Leu Thr Asp Glu Asn Arg Asn Lys Val
                    100                 105                 110

Tyr Ser Leu Leu Lys Ser Leu Glu Lys Asp Pro Lys Glu Met Ile Arg
            115                 120                 125

Lys Met Met Ser Gly Val Leu Ala Ser Glu Ile Gly Val Lys Ser Asp
130                 135                 140

Val Glu Leu Ile Val Asp Pro Met Pro Asn Leu Tyr Phe Thr Arg Asp
145                 150                 155                 160

Pro Phe Ala Ser Val Gly Asn Gly Ile Thr Leu His Arg Met Phe Arg
                    165                 170                 175

Pro Thr Arg Arg Arg Glu Thr Ile Phe Ala Asp Phe Ile Phe Ser Asn
                180                 185                 190

His Pro Glu Tyr Lys Ser Thr Gln Lys Tyr Tyr Glu Arg Glu Asp Lys
            195                 200                 205

Phe Ser Leu Glu Gly Gly Asp Val Phe Ile Tyr Asn Asn Lys Thr Leu
210                 215                 220

Val Val Gly Val Ser Glu Arg Thr Glu Lys Gly Ala Ile Lys Ala Leu
225                 230                 235                 240

Ala Lys Ala Val Gln Asn Asn Ser Asn Met Ser Phe Glu Lys Ile Tyr
                    245                 250                 255

Ala Ile Asn Val Pro Lys Met Ser Asn Leu Met His Leu Asp Thr Trp
                260                 265                 270

Leu Thr Met Leu Asp Thr Asp Lys Phe Leu Tyr Ser Pro Asn Met Met
            275                 280                 285

Gly Val Leu Lys Ile Trp Glu Ile Asp Leu Ser Asp Lys Ser Leu Lys
290                 295                 300

Trp Lys Glu Ile Arg Asp Ser Leu Asp His Phe Leu Ser Thr Ile Ile
305                 310                 315                 320

Gly Lys Lys Ala Ile Thr Val Pro Val Ala Gly Lys Asp Ala Met Gln
                    325                 330                 335

Phe Glu Ile Asp Ile Glu Thr His Phe Asp Ala Thr Asn Phe Ile Ala
                340                 345                 350

Val Ala Pro Gly Val Val Ile Gly Tyr Asp Arg Asn Lys Lys Thr Asn
            355                 360                 365

Glu Ala Leu Lys Glu Ala Gly Ile Lys Val Leu Ser Trp Asn Gly Asp
370                 375                 380

Gln Leu Ser Leu Gly Met Gly Ser Ala Arg Cys Met Thr Met Pro Leu
385                 390                 395                 400

Tyr Arg Glu Glu Leu Lys Lys
            405

<210> SEQ ID NO 11
<211> LENGTH: 402
<212> TYPE: PRT
<213> ORGANISM: Mycoplasma crocodyli

<400> SEQUENCE: 11

Met Asn Lys Ile Asn Val Tyr Ser Glu Val Gly Lys Leu Lys Glu Val

```
1               5                   10                  15
Leu Val His Thr Pro Gly Asp Glu Ile Arg Arg Ile Ser Pro Ser Arg
            20                  25                  30
Leu Glu Glu Leu Leu Phe Ser Ala Ile Leu Glu Pro Asp Ser Ala Ile
            35                  40                  45
Glu Glu His Lys Arg Phe Leu Lys Ile Leu Glu Asp Asn Asn Ile Lys
            50                  55                  60
Val Ile Gln Leu Asp Gln Leu Val Ala Asp Thr Tyr Glu Leu Val Asn
 65                  70                  75                  80
Pro Ser Val Arg Asp Ala Phe Ile Glu Lys Trp Leu Asn Glu Ser Glu
                85                  90                  95
Pro Lys Leu Asp Lys Lys Leu Arg Glu Lys Val Lys Glu Tyr Leu Leu
                100                 105                 110
His Thr Gln Lys Thr Val Gly Thr Lys Arg Met Val Arg Ile Met Met
                115                 120                 125
Ala Gly Val Asp Arg Val Glu Leu Gly Val Glu Leu Asp Arg Gln Leu
                130                 135                 140
Val Val Asp Pro Met Pro Asn Leu Tyr Phe Thr Arg Asp Pro Phe Ala
145                 150                 155                 160
Ser Ala Gly Asn Gly Ile Ser Leu Asn Asn Met Lys Tyr Val Thr Arg
                165                 170                 175
Lys Arg Glu Thr Ile Phe Ser Glu Phe Ile Phe Glu Asn His Pro Asp
                180                 185                 190
Tyr Lys Thr Thr Pro His Trp Phe Asp Arg Leu Asp Lys Gly Asn Ile
                195                 200                 205
Glu Gly Gly Asp Val Phe Ile Tyr Asn Arg Thr Thr Leu Val Ile Gly
                210                 215                 220
Ile Ser Glu Arg Thr Asn Lys Asp Ala Leu Leu Thr Ile Ala Asn Asn
225                 230                 235                 240
Ile Lys Ser Asn Lys Glu Ser Lys Phe Glu Arg Ile Val Ala Val Asn
                245                 250                 255
Val Pro Pro Met Pro Asn Leu Met His Leu Asp Thr Trp Leu Thr Met
                260                 265                 270
Val Asp His Asp Lys Phe Leu Tyr Ser Pro Asn Met Met Lys Thr Leu
                275                 280                 285
Lys Phe Trp Thr Ile Asp Leu Thr Lys Pro Ile Lys Met Val Glu Leu
                290                 295                 300
Glu Glu Ser Leu Ser Asp Met Ile Glu Thr Ile Ile Gly Lys Lys Pro
305                 310                 315                 320
Val Leu Ile Pro Ile Ala Gly His Asp Ala Ser Pro Leu Asp Val Asp
                325                 330                 335
Ile Glu Thr His Phe Asp Gly Thr Asn Tyr Leu Thr Ile Ala Pro Gly
                340                 345                 350
Val Val Val Gly Tyr Ser Arg Asn Lys Leu Thr Glu Lys Ala Leu Thr
                355                 360                 365
Lys Ala Gly Val Lys Val Leu Ser Phe Glu Gly Asn Gln Leu Ser Leu
                370                 375                 380
Gly Met Gly Ser Ala Arg Cys Met Ser Met Pro Leu Val Arg Glu Asp
385                 390                 395                 400
Ile Lys

<210> SEQ ID NO 12
<211> LENGTH: 430
```

```
<212> TYPE: PRT
<213> ORGANISM: Mycoplasma fermentans

<400> SEQUENCE: 12
```

Met Gln Ile Ile Ala Lys Ile Asp Leu Leu Thr Asn Met Leu Ile Phe
1               5                   10                  15

Met Lys Ile Tyr Phe Ile Gly Arg Leu Ile Met Lys Lys Ile Asn Val
            20                  25                  30

Tyr Ser Glu Tyr Gly Lys Leu Lys Glu Val Leu Val His Thr Pro Gly
        35                  40                  45

Asp Glu Ile Arg Arg Ile Ala Pro Ser Arg Leu Asp Glu Leu Leu Phe
        50                  55                  60

Ser Ala Ile Leu Glu Pro Asp Ser Ala Ile Ala Glu His Lys Arg Phe
65                  70                  75                  80

Val Gln Leu Leu Lys Asp Asn Gly Ile Lys Val Ile Gln Leu Asp Glu
                85                  90                  95

Leu Phe Ala Lys Thr Phe Asp Leu Val Ser Glu Ser Val Lys Gln Ser
            100                 105                 110

Leu Ile Glu Arg Trp Leu Asp Glu Cys Glu Pro Lys Leu Asp Ala Thr
        115                 120                 125

Leu Arg Ala Lys Val Lys Glu Tyr Ile Leu Glu Leu Lys Ala Lys Ser
        130                 135                 140

Ser Lys Lys Met Val Arg Val Met Met Ala Gly Ile Asp Lys Lys Glu
145                 150                 155                 160

Leu Gly Ile Glu Leu Asp Arg Asp Leu Val Val Asp Pro Met Pro Asn
                165                 170                 175

Leu Tyr Phe Thr Arg Asp Pro Phe Ala Ser Val Gly Asn Gly Ile Ser
            180                 185                 190

Leu His His Met Lys Tyr Val Thr Arg Gln Arg Glu Thr Ile Phe Ser
        195                 200                 205

Glu Phe Ile Phe Asp Asn Asn Leu Asp Tyr Asn Thr Val Pro Arg Trp
        210                 215                 220

Phe Asp Arg Lys Asp Glu Gly Arg Ile Glu Gly Gly Asp Val Phe Ile
225                 230                 235                 240

Tyr Ser Ala Asp Thr Leu Val Val Gly Val Ser Glu Arg Thr Asn Lys
                245                 250                 255

Glu Ala Ile Asn Val Met Ala Arg Lys Ile Ala Ala Asp Lys Glu Val
            260                 265                 270

Lys Phe Lys Arg Ile Tyr Ala Ile Asn Val Pro Pro Met Pro Asn Leu
        275                 280                 285

Met His Leu Asp Thr Trp Leu Thr Met Leu Asp Lys Asn Lys Phe Leu
        290                 295                 300

Tyr Ser Pro Asn Met Leu Ser Val Leu Lys Val Trp Arg Ile Asp Leu
305                 310                 315                 320

Asn Asp Pro Asp Phe Val Trp His Glu Ile Glu Gly Ser Leu Glu Glu
                325                 330                 335

Ile Leu Glu Gln Ile Ile Gly Met Lys Pro Ile Leu Ile Pro Ile Ala
            340                 345                 350

Gly Lys Gly Ala Ser Gln Leu Asp Ile Asp Ile Glu Thr His Phe Asp
        355                 360                 365

Gly Thr Asn Tyr Leu Thr Ile Ala Pro Ser Val Val Gly Tyr Ser
        370                 375                 380

Arg Asn Glu Lys Thr Glu Lys Ala Leu Lys Ala Ala Lys Val Lys Val
385                 390                 395                 400

```
Leu Ser Phe Glu Gly Asn Gln Leu Ser Leu Gly Met Gly Ser Ala Arg
            405                 410                 415

Cys Met Ser Met Pro Leu Ile Arg Glu Asp Ile Lys Lys Lys
            420                 425                 430

<210> SEQ ID NO 13
<211> LENGTH: 452
<212> TYPE: PRT
<213> ORGANISM: Mycoplasma penetrans

<400> SEQUENCE: 13

Met Val Ile Thr Ile Ala Leu Asn Ile Leu Asn Lys Ile Tyr Phe Lys
1               5                   10                  15

Pro Gln Asn Arg Ser Ile Leu Lys Leu Tyr Arg Leu Pro Ser Leu Cys
            20                  25                  30

Thr Gln Ile Ser Ile Phe Ile Gly Gly Lys Met Ser Ser Ile Asp Lys
        35                  40                  45

Asn Ser Leu Gly Asn Gly Ile Asn Val Tyr Ser Glu Ile Gly Glu Leu
    50                  55                  60

Lys Glu Val Leu Val His Thr Pro Gly Asp Glu Ile Arg Tyr Thr Ala
65                  70                  75                  80

Pro Ser Arg Leu Glu Glu Leu Leu Phe Ser Ala Val Leu Lys Ala Asp
                85                  90                  95

Thr Ala Ile Glu Glu His Lys Gly Phe Val Lys Ile Leu Gln Asn Asn
            100                 105                 110

Gly Ile Lys Val Ile Gln Leu Cys Asp Leu Val Ala Glu Thr Tyr Glu
        115                 120                 125

Leu Cys Ser Lys Glu Val Arg Asn Ser Phe Ile Glu Gln Tyr Leu Asp
    130                 135                 140

Glu Ala Leu Pro Val Leu Lys Lys Glu Ile Arg Pro Val Val Lys Asp
145                 150                 155                 160

Tyr Leu Leu Ser Phe Pro Thr Val Gln Met Val Arg Lys Met Met Ser
                165                 170                 175

Gly Ile Leu Ala Asn Glu Leu Asn Ile Lys Gln Asp Asn Pro Leu Ile
            180                 185                 190

Ile Asp Gly Met Pro Asn Leu Tyr Phe Thr Arg Asp Pro Phe Ala Ser
        195                 200                 205

Met Gly Asn Gly Val Ser Ile Asn Cys Met Lys Tyr Pro Thr Arg Lys
    210                 215                 220

Arg Glu Val Ile Phe Ser Arg Phe Val Phe Thr Asn Asn Pro Lys Tyr
225                 230                 235                 240

Lys Asn Thr Pro Arg Tyr Phe Asp Ile Val Gly Asn Asn Gly Thr Ile
                245                 250                 255

Glu Gly Gly Asp Ile Phe Ile Tyr Asn Ser Lys Thr Leu Val Ile Gly
            260                 265                 270

Asn Ser Glu Arg Thr Asn Phe Ala Ala Ile Glu Ser Val Ala Lys Asn
        275                 280                 285

Ile Gln Ala Asn Lys Asp Cys Thr Phe Glu Arg Ile Val Val Ile Asn
    290                 295                 300

Val Pro Pro Met Pro Asn Leu Met His Leu Asp Thr Trp Leu Thr Met
305                 310                 315                 320

Leu Asp Tyr Asp Lys Phe Leu Tyr Ser Pro Asn Met Met Asn Val Leu
                325                 330                 335

Lys Ile Trp Glu Ile Asp Leu Asn Val Lys Pro Val Lys Phe Val Glu
```

```
                    340                 345                 350
Lys Lys Gly Thr Leu Glu Glu Val Leu Tyr Ser Ile Ile Asp Lys Lys
            355                 360                 365
Pro Ile Leu Ile Pro Ile Ala Gly Lys Gly Ala Asn Gln Leu Asp Ile
        370                 375                 380
Asp Ile Glu Thr His Phe Asp Gly Thr Asn Tyr Leu Thr Ile Ala Pro
385                 390                 395                 400
Gly Val Val Gly Tyr Glu Arg Asn Glu Lys Thr Gln Lys Ala Leu
                405                 410                 415
Val Glu Ala Gly Ile Lys Val Leu Ser Phe Asn Gly Ser Gln Leu Ser
            420                 425                 430
Leu Gly Met Gly Ser Ala Arg Cys Met Ser Met Pro Leu Ile Arg Glu
        435                 440                 445
Asn Leu Lys Lys
    450

<210> SEQ ID NO 14
<211> LENGTH: 403
<212> TYPE: PRT
<213> ORGANISM: Mycoplasma gallisepticum

<400> SEQUENCE: 14

Met Phe Asn Lys Ile Arg Val Tyr Ser Glu Ile Gly Lys Leu Arg Lys
1               5                   10                  15
Val Leu Val His Thr Pro Gly Lys Glu Leu Asp Tyr Val Thr Pro Gln
            20                  25                  30
Arg Leu Asp Glu Leu Leu Phe Ser Ser Leu Leu Asn Pro Ile Lys Ala
        35                  40                  45
Arg Gln Glu His Glu Thr Phe Ile Lys Leu Leu Glu Asp His Asp Val
    50                  55                  60
Glu Cys Val Gln Leu Ser Thr Leu Thr Ala Gln Thr Phe Gln Ala Val
65                  70                  75                  80
Asn Ser Lys Ile Gln Glu Glu Phe Ile Asn Arg Trp Leu Asp Glu Cys
                85                  90                  95
Leu Pro Val Leu Ser Glu Ile Asn Arg Leu Lys Val Tyr Asp Tyr Leu
            100                 105                 110
Lys Ser Leu Ala Thr Asn Pro Gln Val Met Ile Arg Lys Met Met Ser
        115                 120                 125
Gly Ile Leu Ala Lys Glu Val Gly Ile Gln Ser Glu Val Glu Leu Val
    130                 135                 140
Ala Asp Pro Met Pro Asn Leu Tyr Phe Thr Arg Asp Pro Phe Ala Ser
145                 150                 155                 160
Ile Gly Lys Gly Ile Thr Leu His Ser Met Phe His Pro Thr Arg Lys
                165                 170                 175
Arg Glu Thr Ile Phe Ala Asp Phe Ile Phe Ser His His Pro Glu Tyr
            180                 185                 190
Lys Asn Ala Pro Lys Tyr Tyr Ser Arg Glu Asp Lys Tyr Ser Ile Glu
        195                 200                 205
Gly Gly Asp Leu Phe Val Tyr Asp Asp Lys Thr Leu Val Ile Gly Val
    210                 215                 220
Ser Glu Arg Thr Glu Lys Lys Ala Ile Gln Ser Leu Ala Glu Lys Leu
225                 230                 235                 240
Arg Gln Asn Asp Glu Thr Ser Phe Glu Lys Ile Tyr Ala Ile Asn Val
                245                 250                 255
```

```
Pro Lys Met Ser Asn Leu Met His Leu Asp Thr Trp Leu Thr Met Leu
            260                 265                 270

Asp Tyr Asp Lys Phe Leu Tyr Ser Pro Asn Met Met Gly Val Leu Lys
            275                 280                 285

Ile Trp Glu Ile Asp Leu Ile His Pro Thr Leu Ile Trp Arg Glu Leu
    290                 295                 300

Asn Glu Ser Leu Glu Gly Phe Leu Ser Met Val Ile Gly Lys Lys Ala
305                 310                 315                 320

Thr Leu Ile Pro Val Ala Gly Glu Asp Ser Thr Gln Ile Glu Ile Asp
                325                 330                 335

Val Glu Thr Asn Phe Asp Ala Thr Asn Phe Leu Val Ile Gln Pro Gly
            340                 345                 350

Val Val Val Gly Tyr Asp Arg Asn Tyr Lys Thr Asn Gln Ala Leu Arg
            355                 360                 365

Asp Ala Gly Val Lys Val Ile Ser Trp Asn Gly Asp Gln Leu Ser Leu
            370                 375                 380

Gly Met Gly Ser Ala Arg Cys Met Ser Met Pro Leu Tyr Arg Asp Pro
385                 390                 395                 400

Ile Lys Lys

<210> SEQ ID NO 15
<211> LENGTH: 402
<212> TYPE: PRT
<213> ORGANISM: Mycoplasma alligatoris

<400> SEQUENCE: 15

Met Ser Lys Ile Asn Val Tyr Ser Glu Val Gly Arg Leu Lys Glu Val
1               5                   10                  15

Leu Val His Thr Pro Gly Asp Glu Ile Arg Arg Ile Ser Pro Thr Arg
            20                  25                  30

Leu Glu Glu Leu Leu Phe Ser Ala Ile Leu Glu Pro Asp Thr Ala Ile
            35                  40                  45

Glu Glu His Lys Arg Phe Leu Asn Val Leu Glu Lys Asn Gly Ile Lys
    50                  55                  60

Ala Ile Gln Leu Asp Glu Leu Val Ala Gln Thr Tyr Asp Gln Val Asp
65                  70                  75                  80

Gln Lys Ile Lys Asp Glu Phe Ile Asp Gln Trp Leu Gln Glu Ala Lys
                85                  90                  95

Pro Val Leu Asn Asp Gln Leu Lys Lys Leu Val Lys Asn Tyr Leu Leu
            100                 105                 110

Lys Ser Gln Lys Glu Phe Ser Thr Lys Lys Met Val Arg Ile Met Met
            115                 120                 125

Ala Gly Ile Asp Lys Lys Glu Ile Asn Ile Asp Leu Asp Arg Asp Leu
130                 135                 140

Val Val Asp Pro Met Pro Asn Leu Tyr Phe Thr Arg Asp Pro Phe Ala
145                 150                 155                 160

Ser Val Gly Asn Gly Ile Ser Leu His Asn Met Lys Tyr Gln Thr Arg
                165                 170                 175

Lys Arg Glu Thr Ile Phe Ala Gln Phe Ile Phe Lys Tyr Asn Lys Asp
            180                 185                 190

Tyr Lys Thr Thr Pro His Trp Phe Asp Arg Phe Asp His Gly Ser Ile
            195                 200                 205

Glu Gly Gly Asp Val Phe Val Tyr Thr Lys Asp Thr Leu Val Ile Gly
    210                 215                 220
```

```
Ile Ser Glu Arg Thr Thr Lys Glu Ala Val Leu Asn Ile Ala Lys Lys
225                 230                 235                 240

Ile Lys Ala Asn Thr Asp Ser Lys Phe Lys Ile Val Ala Ile Asn
            245                 250                 255

Val Pro Pro Met Pro Asn Leu Met His Leu Asp Thr Trp Ile Thr Met
                260                 265                 270

Val Asp His Asp Lys Phe Leu Tyr Ser Pro Asn Met Met Lys Ser Leu
            275                 280                 285

Lys Phe Trp Leu Ile Asp Leu Ser Lys Glu Ile Lys Met Val Glu Leu
            290                 295                 300

Glu Glu Ser Leu Ser Asn Met Leu Glu Ala Ile Ile Gly Lys Lys Pro
305                 310                 315                 320

Ile Leu Ile Pro Ile Ala Gly Lys Asn Ala Ser Gln Leu Asp Ile Asp
                325                 330                 335

Ile Glu Thr His Phe Asp Gly Thr Asn Tyr Leu Thr Ile Ala Pro Gly
                340                 345                 350

Val Val Val Gly Tyr Ser Arg Asn Lys Leu Thr Gln Lys Ala Leu Glu
            355                 360                 365

Asp Ala Gly Val Lys Val Leu Ser Phe Asp Gly Asn Gln Leu Ser Leu
370                 375                 380

Gly Met Gly Ser Ala Arg Cys Met Ser Met Pro Leu Val Arg Glu Asp
385                 390                 395                 400

Ile Lys

<210> SEQ ID NO 16
<211> LENGTH: 438
<212> TYPE: PRT
<213> ORGANISM: Mycoplasma pneumoniae

<400> SEQUENCE: 16

Met Ser Lys Lys Gln Leu Val Lys Thr Asp Gly His Asn Gln Leu Asp
1               5                   10                  15

Gln Pro Asn Thr Lys Ala Leu Gln Leu Lys Lys Gln Phe Asn Ser
            20                  25                  30

Gly Val Arg Val Thr Ser Glu Ile Ser Phe Leu Arg Glu Val Ile Ala
            35                  40                  45

His His Pro Gly Ile Glu Thr Glu Arg Val Ile Asp Asn Gln Thr Phe
        50                  55                  60

Gly Ser Ala Met Tyr Leu Glu Arg Ala Gln Lys Glu His Gln Leu Phe
65                  70                  75                  80

Ile Lys Ile Leu Arg Gln His Gly Thr Lys Val His Tyr Leu Gln Asp
                85                  90                  95

Leu Leu Leu Glu Ala Leu Ser Ala Ala Asp Pro Asn Val Arg Gln Asp
            100                 105                 110

Phe Ile Lys Asn Phe Leu Leu Glu Ser Gly Ile Lys Ser Val Ser Thr
            115                 120                 125

Phe Glu Ala Cys Leu Asn Phe Phe Arg Ser Leu Asp Ser Leu Val Asp
            130                 135                 140

Val Ile Lys Val Met Phe Gly Gly Ile Lys Val Ser Asp Val Pro Pro
145                 150                 155                 160

Ile Thr Pro Gln Arg Phe Ala Asp Ile His Val Ser Asn Ser Pro Phe
                165                 170                 175

Leu Ile Lys Pro Leu Ser Phe Ser Leu Tyr Pro His Lys Phe Phe Asn
            180                 185                 190
```

-continued

```
Thr Leu Gly Thr Gly Val Ala Leu Phe Val Thr Asn Asp Ser Glu Leu
            195                 200                 205

Lys Arg His Ser Leu Val Tyr Glu Tyr Ile Met Arg Phe His Pro Arg
210                 215                 220

Phe Asp Gly Val Lys Leu Tyr Thr Asn Arg Asp Phe Lys Asn Cys Leu
225                 230                 235                 240

Ile Asn Ser Ser Asp Ile Ile Gln Ile Ser Asn Glu Ile Leu Leu Ile
            245                 250                 255

Gly Ile Ser His Asp Thr Asp Val Leu Gly Ile Glu Ser Leu Ala Arg
            260                 265                 270

Asn Leu Leu Ser Asp His Thr Asn Pro Ile Lys Gln Ile Ile Ala Ile
            275                 280                 285

Asn Ile His Lys Phe Gly Ala Lys Thr Asn Leu Asn Lys Leu Ile Ala
            290                 295                 300

Met Val Asp Val Asp Lys Phe Ile Ile Ala Arg Lys Val Leu Gln Ala
305                 310                 315                 320

Thr Glu Ile Phe Glu Leu Thr Ala Thr Ala Gln Arg Asp Val Asp Gly
            325                 330                 335

Leu Ala Gln Ile Lys Phe Lys Pro Leu Lys Phe Asn Phe Gly Glu Ile
            340                 345                 350

Ile Glu Ala Ile Ile Asp Lys Gln Pro Arg Phe Val Ile Ile Gly Gly
            355                 360                 365

Gly Asp Glu Val Ala Glu Arg Lys Glu Leu Leu Asp Cys Gly Met Gly
            370                 375                 380

Val Leu Asn Leu Ser Pro Gly Glu Ile Val Val Phe Asp Arg Asn His
385                 390                 395                 400

Tyr Thr Asn Asn Leu Leu Asn Glu Leu Gly Leu Ile Ile His Lys Ile
            405                 410                 415

Pro Ala Ser Glu Leu Ser Arg Gly Pro Ser Gly Pro Leu Glu Met Val
            420                 425                 430

Cys Ser Leu Trp Arg Glu
            435

<210> SEQ ID NO 17
<211> LENGTH: 409
<212> TYPE: PRT
<213> ORGANISM: Mycoplasma mobile

<400> SEQUENCE: 17

Met Lys Asp Thr Lys Asp Ile Ile Asn Val Phe Ser Glu Ile Gly Glu
1               5                   10                  15

Leu Lys Lys Val Leu Ile His Thr Pro Gly Asn Glu Leu Lys Tyr Val
            20                  25                  30

Ser Pro Tyr Arg Leu Asp Glu Leu Phe Ser Asn Val Leu Glu Trp
            35                  40                  45

Arg Glu Ala Lys Lys Glu His Asn Glu Phe Ile Gln Lys Leu Lys Ser
            50                  55                  60

Glu Gly Val Glu Pro Val Leu Thr Asp Leu Val Ala Glu Ser Phe
65                  70                  75                  80

Glu Glu Ser Ser Ile Lys Val Lys Asn Asp Phe Ile Arg Gln Tyr Leu
            85                  90                  95

Asp Glu Ala Thr Pro Ile Leu Asp Gly Leu Thr Lys Gln Lys Leu Leu
            100                 105                 110

Pro Phe Phe Leu Asp Ile Lys His Ser Thr Arg Lys Thr Ile Glu Leu
            115                 120                 125
```

```
Met Met Ser Gly Ile Thr Gln Lys Asp Ile Ser Ile Ser His Ile Glu
            130                 135                 140

Arg Glu Leu Ile Ile Asp Pro Met Pro Asn Leu Tyr Phe Ser Arg Asp
145                 150                 155                 160

Asn Phe Ile Ser Ile Gly Asn Ser Val Ile Ser Asn Met Lys Tyr
                165                 170                 175

Lys Thr Arg Lys Arg Glu Thr Ile Phe Thr Asp Phe Ile Phe Lys Asn
                180                 185                 190

His Pro Leu Tyr Lys Lys Val Asn Met Ala Phe Glu Arg Lys Asp Leu
                195                 200                 205

Asn Asn Gln Ile Ser Ile Ile Glu Gly Gly Asp Val Leu Val Tyr Ser
210                 215                 220

Lys Glu Ile Leu Ile Ile Gly Ile Ser Glu Arg Thr Thr Met Ser Ala
225                 230                 235                 240

Ile Leu Glu Leu Ala Glu Asn Phe Lys Lys Thr Lys Arg Ser Phe Lys
                245                 250                 255

Lys Ile Tyr Gly Val Glu Val Pro Lys Met Lys Asn Leu Met His Leu
                260                 265                 270

Asp Thr Trp Leu Thr Met Ile Asp Tyr Asp Lys Phe Ile Tyr Ser Pro
                275                 280                 285

Asn Val Leu Thr Asp Leu Lys Phe Trp Glu Ile Asn Leu Asp Tyr Glu
                290                 295                 300

Lys Ile Ser Ser Lys Glu Leu His Ala Ser Leu Ser Glu Phe Leu Lys
305                 310                 315                 320

Leu Ile Ile Gly Lys Asp Pro Ile Leu Ile Pro Ile Gly Gly Lys Gly
                325                 330                 335

Ala Ser Gln Ile Thr Ile Asp Ile Glu Thr Asn Phe Val Ala Ala Asn
                340                 345                 350

Tyr Leu Val Ile Arg Pro Gly Val Val Ile Gly Tyr Ser Arg Asn Tyr
                355                 360                 365

Glu Thr Gln Lys Ala Leu Glu Gly His Gly Val Lys Val Ile Ala Phe
                370                 375                 380

Glu Gly Asn Gln Leu Ser Leu Gly Met Gly Ser Ser Arg Cys Met Ser
385                 390                 395                 400

Met Pro Leu Ile Arg Ser Asn Leu Lys
                405

<210> SEQ ID NO 18
<211> LENGTH: 411
<212> TYPE: PRT
<213> ORGANISM: Streptococcus pyogenes

<400> SEQUENCE: 18

Met Thr Ala Gln Thr Pro Ile His Val Tyr Ser Glu Ile Gly Lys Leu
1               5                   10                  15

Lys Lys Val Leu Leu His Arg Pro Gly Lys Glu Ile Glu Asn Leu Met
                20                  25                  30

Pro Asp Tyr Leu Glu Arg Leu Leu Phe Asp Asp Ile Pro Phe Leu Glu
                35                  40                  45

Asp Ala Gln Lys Glu His Asp Ala Phe Ala Gln Ala Leu Arg Asp Glu
                50                  55                  60

Gly Ile Glu Val Leu Tyr Leu Glu Thr Leu Ala Ala Glu Ser Leu Val
65                  70                  75                  80

Thr Pro Glu Ile Arg Glu Ala Phe Ile Asp Glu Tyr Leu Ser Glu Ala
```

```
                    85                  90                  95
Asn Ile Arg Gly Arg Ala Thr Lys Lys Ala Ile Arg Glu Leu Leu Met
                100                 105                 110

Ala Ile Glu Asp Asn Gln Glu Leu Ile Glu Lys Thr Met Ala Gly Val
                115                 120                 125

Gln Lys Ser Glu Leu Pro Glu Ile Pro Ala Ser Glu Lys Gly Leu Thr
            130                 135                 140

Asp Leu Val Glu Ser Asn Tyr Pro Phe Ala Ile Asp Pro Met Pro Asn
145                 150                 155                 160

Leu Tyr Phe Thr Arg Asp Pro Phe Ala Thr Ile Gly Thr Gly Val Ser
                165                 170                 175

Leu Asn His Met Phe Ser Glu Thr Arg Asn Arg Glu Thr Leu Tyr Gly
            180                 185                 190

Lys Tyr Ile Phe Thr His His Pro Ile Tyr Gly Gly Lys Val Pro
                195                 200                 205

Met Val Tyr Asp Arg Asn Glu Thr Thr Arg Ile Glu Gly Gly Asp Glu
            210                 215                 220

Leu Val Leu Ser Lys Asp Val Leu Ala Val Gly Ile Ser Gln Arg Thr
225                 230                 235                 240

Asp Ala Ala Ser Ile Glu Lys Leu Leu Val Asn Ile Phe Lys Gln Asn
                245                 250                 255

Leu Gly Phe Lys Lys Val Leu Ala Phe Glu Phe Ala Asn Asn Arg Lys
            260                 265                 270

Phe Met His Leu Asp Thr Val Phe Thr Met Val Asp Tyr Asp Lys Phe
                275                 280                 285

Thr Ile His Pro Glu Ile Glu Gly Asp Leu Arg Val Tyr Ser Val Thr
            290                 295                 300

Tyr Asp Asn Glu Glu Leu His Ile Val Glu Glu Lys Gly Asp Leu Ala
305                 310                 315                 320

Glu Leu Leu Ala Ala Asn Leu Gly Val Glu Lys Val Asp Leu Ile Arg
                325                 330                 335

Cys Gly Gly Asp Asn Leu Val Ala Ala Gly Arg Glu Gln Trp Asn Asp
            340                 345                 350

Gly Ser Asn Thr Leu Thr Ile Ala Pro Gly Val Val Val Tyr Asn
            355                 360                 365

Arg Asn Thr Ile Thr Asn Ala Ile Leu Glu Ser Lys Gly Leu Lys Leu
            370                 375                 380

Ile Lys Ile His Gly Ser Glu Leu Val Arg Gly Arg Gly Gly Pro Arg
385                 390                 395                 400

Cys Met Ser Met Pro Phe Glu Arg Glu Asp Ile
                405                 410

<210> SEQ ID NO 19
<211> LENGTH: 408
<212> TYPE: PRT
<213> ORGANISM: Enterococcus faecalis

<400> SEQUENCE: 19

Met Ser His Pro Ile Asn Val Phe Ser Glu Ile Gly Lys Leu Lys Thr
1               5                   10                  15

Val Met Leu His Arg Pro Gly Lys Glu Leu Glu Asn Leu Met Pro Asp
                20                  25                  30

Tyr Leu Glu Arg Leu Leu Phe Asp Asp Ile Pro Phe Leu Glu Lys Ala
            35                  40                  45
```

```
Gln Ala Glu His Asp Ala Phe Ala Glu Leu Leu Arg Ser Lys Asp Ile
 50                  55                  60

Glu Val Val Tyr Leu Glu Asp Leu Ala Ala Glu Ala Leu Ile Asn Glu
 65                  70                  75                  80

Glu Val Arg Arg Gln Phe Ile Asp Gln Phe Leu Glu Glu Ala Asn Ile
                 85                  90                  95

Arg Ser Glu Ser Ala Lys Glu Lys Val Arg Glu Leu Met Leu Glu Ile
                100                 105                 110

Asp Asp Asn Glu Glu Leu Ile Gln Lys Ala Ile Ala Gly Ile Gln Lys
            115                 120                 125

Gln Glu Leu Pro Lys Tyr Glu Gln Glu Phe Leu Thr Asp Met Val Glu
130                 135                 140

Ala Asp Tyr Pro Phe Ile Ile Asp Pro Met Pro Asn Leu Tyr Phe Thr
145                 150                 155                 160

Arg Asp Asn Phe Ala Thr Met Gly His Gly Ile Ser Leu Asn His Met
                165                 170                 175

Tyr Ser Val Thr Arg Gln Arg Glu Thr Ile Phe Gly Tyr Ile Phe
                180                 185                 190

Asp Tyr His Pro Arg Phe Ala Gly Lys Glu Val Pro Arg Val Tyr Asp
            195                 200                 205

Arg Ser Glu Ser Thr Arg Ile Glu Gly Gly Asp Glu Leu Ile Leu Ser
210                 215                 220

Lys Glu Val Val Ala Ile Gly Ile Ser Gln Arg Thr Asp Ala Ala Ser
225                 230                 235                 240

Ile Glu Lys Ile Ala Arg Asn Ile Phe Glu Gln Lys Leu Gly Phe Lys
                245                 250                 255

Asn Ile Leu Ala Phe Asp Ile Gly Glu His Arg Lys Phe Met His Leu
            260                 265                 270

Asp Thr Val Phe Thr Met Ile Asp Tyr Asp Lys Phe Thr Ile His Pro
            275                 280                 285

Glu Ile Glu Gly Gly Leu Val Val Tyr Ser Ile Thr Glu Lys Ala Asp
290                 295                 300

Gly Asp Ile Gln Ile Thr Lys Glu Lys Asp Thr Leu Asp Asn Ile Leu
305                 310                 315                 320

Cys Lys Tyr Leu His Leu Asp Asn Val Gln Leu Ile Arg Cys Gly Ala
                325                 330                 335

Gly Asn Leu Thr Ala Ala Arg Glu Gln Trp Asn Asp Gly Ser Asn
            340                 345                 350

Thr Leu Ala Ile Ala Pro Gly Glu Val Val Tyr Asp Arg Asn Thr
            355                 360                 365

Ile Thr Asn Lys Ala Leu Glu Glu Ala Gly Val Lys Leu Asn Tyr Ile
370                 375                 380

Pro Gly Ser Glu Leu Val Arg Gly Arg Gly Pro Arg Cys Met Ser
385                 390                 395                 400

Met Pro Leu Tyr Arg Glu Asp Leu
                405

<210> SEQ ID NO 20
<211> LENGTH: 403
<212> TYPE: PRT
<213> ORGANISM: Mycoplasma capricolum

<400> SEQUENCE: 20

Met Glu Lys Lys Ile Asn Val Phe Ser Glu Ile Gly Thr Leu Lys Thr
 1               5

Val Leu Val His Arg Pro Gly Asp Glu Ile Glu Asn Leu Thr Pro Glu
            20                  25                  30

Leu Leu Glu Arg Leu Phe Asp Asp Val Pro Phe Lys Asp Val Ala
        35                  40                  45

Val Lys Glu His Asp Ala Phe Thr Lys Ile Met Arg Asp Asn Gly Val
 50                  55                  60

Glu Val Leu Tyr Ile Glu Lys Leu Ala Ala Glu Thr Leu Asp Gln His
65                  70                  75                  80

Pro Asp Leu Arg Glu Lys Phe Ile Asp Gln Phe Ile Ser Glu Ala Asn
                85                  90                  95

Ile Glu Asp Lys Tyr Lys Glu Lys Tyr Arg Asp Phe Ile Ser Ser Leu
            100                 105                 110

Asp Asn Tyr Arg Met Ile Lys Lys Met Ile Ala Gly Thr Lys Lys Leu
        115                 120                 125

Glu Leu Gly Ile Asp Glu Gly Tyr Lys Ala Tyr Pro Phe Ile Ala Asp
130                 135                 140

Pro Leu Pro Asn Val Leu Phe Gln Arg Asp Pro Phe Ser Ser Val Gly
145                 150                 155                 160

Phe Gly Ile Thr Met Asn Arg Met Trp Ser Val Thr Arg Asn Arg Glu
                165                 170                 175

Thr Ile Phe Pro Asp Leu Val Phe Lys His His Asn Arg Phe Ala Asn
            180                 185                 190

Gln Val Pro Tyr Tyr Tyr Glu Arg Asp Trp Lys Glu Glu Thr Ile Glu
        195                 200                 205

Gly Gly Asp Ile Leu Val Leu Asn Lys Glu Thr Leu Ile Ile Gly Val
210                 215                 220

Thr Gln Arg Thr Thr Leu Lys Ala Ile Glu Lys Phe Ser Glu Arg Leu
225                 230                 235                 240

Phe Asn Asp Pro Glu Ser Ser Tyr Ser Lys Val Ile Ala Leu Asp Leu
                245                 250                 255

Pro Lys Ser Arg Ala Phe Met His Leu Asp Thr Val Phe Thr Asn Ile
            260                 265                 270

Asp Tyr Asp Lys Phe Ile Ala His Pro Leu Ile Phe Asp Cys Ile Asp
        275                 280                 285

Glu Phe Lys Ile Tyr Glu Val Ser Lys Gln Gly Thr Lys Glu Val Lys
290                 295                 300

Lys Thr Leu Ile Glu Leu Leu Ser Asp Ala Ala Gly Arg Glu Val Gln
305                 310                 315                 320

Ile Ile Arg Cys Gly Gly Asn Asp Val Val Gly Ala Ser Arg Glu Gln
                325                 330                 335

Trp Asn Asp Gly Thr Asn Val Val Ala Leu Arg Pro Gly Lys Val Ile
            340                 345                 350

Ala Tyr Glu Arg Asn Trp Ile Thr Ile Asp Leu Leu Arg Lys Ala Gly
        355                 360                 365

Val Glu Val Leu Thr Ile Ala Ser Ser Glu Leu Ser Arg Gly Arg Gly
370                 375                 380

Gly Pro Arg Cys Met Thr Met Pro Leu Trp Arg Glu Asp Leu Gln Glu
385                 390                 395                 400

Ile Lys Arg

<210> SEQ ID NO 21
<211> LENGTH: 410
<212> TYPE: PRT

<213> ORGANISM: Halothermothrix orenii

<400> SEQUENCE: 21

```
Met Phe Lys Lys Ser Pro Leu Asn Val Thr Ser Glu Ile Gly Lys Leu
1               5                   10                  15

Lys Lys Val Leu Leu His Arg Pro Gly His Glu Ile Glu Asn Leu Thr
            20                  25                  30

Pro Asp Leu Leu Glu Arg Leu Leu Phe Asp Asp Ile Pro Tyr Leu Lys
        35                  40                  45

Val Ala Gln Glu Glu His Asp Ala Phe Ala Gln Thr Leu Arg Asp Asn
    50                  55                  60

Gly Val Glu Val Leu Tyr Leu His Glu Leu Ala Ala Glu Ala Ile Gln
65                  70                  75                  80

Glu Asp Glu Ile Arg Lys Lys Phe Ile Glu Gln Phe Leu Asp Glu Ala
                85                  90                  95

Gly Val Ile Gly Lys Gly Ala Arg Gln Val Leu Lys Glu Tyr Phe Ala
            100                 105                 110

Asp Met Asp Asn Glu Thr Leu Ile Arg Lys Met Met Ala Gly Val Arg
        115                 120                 125

Lys Lys Glu Ile Pro Ala Ile Glu Lys Val Ala Ser Leu Asn Asp Met
130                 135                 140

Val Glu Glu Asp Tyr Pro Phe Val Leu Asp Pro Met Pro Asn Leu Tyr
145                 150                 155                 160

Phe Thr Arg Asp Pro Phe Ala Thr Ile Gly Thr Gly Ile Thr Leu Asn
                165                 170                 175

His Met Arg Thr Glu Thr Arg Asn Arg Glu Val Ile Phe Ala Glu Tyr
            180                 185                 190

Ile Phe Ser Tyr His Pro Asp Phe Lys Asp Thr Glu Ile Pro Phe Trp
        195                 200                 205

Phe Asp Arg Asn Glu Thr Thr Ser Ile Glu Gly Gly Asp Glu Leu Ile
    210                 215                 220

Leu Ser Asp Lys Val Leu Ala Met Gly Ile Ser Glu Arg Thr Asp Ala
225                 230                 235                 240

Ala Ser Ile Glu Lys Val Ala Arg Asn Ile Phe Thr Asp Gly Gln Pro
                245                 250                 255

Phe Glu Thr Ile Leu Ala Phe Lys Ile Pro Glu Lys Arg Ala Phe Met
            260                 265                 270

His Leu Asp Thr Val Phe Thr Met Val Asp Tyr Asp Lys Phe Thr Ile
        275                 280                 285

His Ala Glu Ile Glu Gly Pro Leu Lys Val Tyr Ser Ile Thr Lys Gly
    290                 295                 300

Asp Asn Asp Glu Leu Lys Ile Asp Glu Lys Ala Thr Leu Glu Asp
305                 310                 315                 320

Thr Leu Lys Lys Tyr Leu Gly Leu Asp Glu Val Thr Leu Ile Arg Cys
                325                 330                 335

Ala Gly Gly Asp Tyr Ile Asp Ala Gly Arg Glu Gln Trp Asn Asp Gly
            340                 345                 350

Ser Asn Thr Leu Ala Ile Ala Pro Gly Glu Val Val Tyr Asn Arg
        355                 360                 365

Asn His Thr Thr Asn Arg Leu Leu Glu Glu His Gly Ile Lys Leu His
    370                 375                 380

Val Ile Pro Ser Ser Glu Leu Ser Arg Gly Arg Gly Gly Pro Arg Cys
385                 390                 395                 400
```

Met Ser Met Pro Leu Val Arg Glu Asp Ile
            405                 410

<210> SEQ ID NO 22
<211> LENGTH: 411
<212> TYPE: PRT
<213> ORGANISM: Staphylococcus aureus

<400> SEQUENCE: 22

Met Thr Asp Gly Pro Ile Lys Val Asn Ser Glu Ile Gly Ala Leu Lys
1               5                   10                  15

Thr Val Leu Leu Lys Arg Pro Gly Lys Glu Leu Glu Asn Leu Val Pro
            20                  25                  30

Asp Tyr Leu Asp Gly Leu Leu Phe Asp Ile Pro Tyr Leu Glu Val
        35                  40                  45

Ala Gln Lys Glu His Asp His Phe Ala Gln Val Leu Arg Glu Glu Gly
    50                  55                  60

Val Glu Val Leu Tyr Leu Glu Lys Leu Ala Ala Glu Ser Ile Glu Asn
65                  70                  75                  80

Pro Gln Val Arg Ser Glu Phe Ile Asp Val Leu Ala Glu Ser Lys
            85                  90                  95

Lys Thr Ile Leu Gly His Glu Glu Ile Lys Ala Leu Phe Ala Thr
                100                 105                 110

Leu Ser Asn Gln Glu Leu Val Asp Lys Ile Met Ser Gly Val Arg Lys
            115                 120                 125

Glu Glu Ile Asn Pro Lys Cys Thr His Leu Val Glu Tyr Met Asp Asp
    130                 135                 140

Lys Tyr Pro Phe Tyr Leu Asp Pro Met Pro Asn Leu Tyr Phe Thr Arg
145                 150                 155                 160

Asp Pro Gln Ala Ser Ile Gly His Gly Ile Thr Ile Asn Arg Met Phe
            165                 170                 175

Trp Arg Ala Arg Arg Glu Ser Ile Phe Ile Gln Tyr Ile Val Lys
                180                 185                 190

His His Pro Arg Phe Lys Asp Ala Asn Ile Pro Ile Trp Leu Asp Arg
            195                 200                 205

Asp Cys Pro Phe Asn Ile Glu Gly Gly Asp Glu Leu Val Leu Ser Lys
    210                 215                 220

Asp Val Leu Ala Ile Gly Val Ser Glu Arg Thr Ser Ala Gln Ala Ile
225                 230                 235                 240

Glu Lys Leu Ala Arg Arg Ile Phe Glu Asn Pro Gln Ala Thr Phe Lys
            245                 250                 255

Lys Val Val Ala Ile Glu Ile Pro Thr Ser Arg Thr Phe Met His Leu
                260                 265                 270

Asp Thr Val Phe Thr Met Ile Asp Tyr Asp Lys Phe Thr Met His Ser
            275                 280                 285

Ala Ile Leu Lys Ala Glu Gly Asn Met Asn Ile Phe Ile Ile Glu Tyr
    290                 295                 300

Asp Asp Val Asn Lys Asp Ile Ala Ile Lys Gln Ser Ser His Leu Lys
305                 310                 315                 320

Asp Thr Leu Glu Asp Val Leu Gly Ile Asp Asp Ile Gln Phe Ile Pro
            325                 330                 335

Thr Gly Asn Gly Asp Val Ile Asp Gly Ala Arg Glu Gln Trp Asn Asp
                340                 345                 350

Gly Ser Asn Thr Leu Cys Ile Arg Pro Gly Val Val Thr Tyr Asp
            355                 360                 365

-continued

Arg Asn Tyr Val Ser Asn Asp Leu Leu Arg Gln Lys Gly Ile Lys Val
    370                 375                 380

Ile Glu Ile Ser Gly Ser Glu Leu Val Arg Gly Arg Gly Gly Pro Arg
385                 390                 395                 400

Cys Met Ser Gln Pro Leu Phe Arg Glu Asp Ile
                405                 410

<210> SEQ ID NO 23
<211> LENGTH: 417
<212> TYPE: PRT
<213> ORGANISM: Pseudomonas plecoglossicida

<400> SEQUENCE: 23

Met Ser Ala Glu Lys Gln Lys Tyr Gly Val His Ser Glu Ala Gly Lys
1               5                   10                  15

Leu Arg Lys Val Met Val Cys Ala Pro Gly Leu Ala His Lys Arg Leu
                20                  25                  30

Thr Pro Ser Asn Cys Asp Glu Leu Leu Phe Asp Asp Val Ile Trp Val
            35                  40                  45

Asp Gln Ala Lys Arg Asp His Phe Asp Phe Val Thr Lys Met Arg Glu
    50                  55                  60

Arg Gly Val Asp Val Leu Glu Met His Asn Leu Leu Thr Asp Ile Val
65                  70                  75                  80

Gln Asn Pro Glu Ala Leu Lys Trp Ile Leu Asp Arg Lys Ile Thr Pro
                85                  90                  95

Asp Thr Val Gly Val Gly Leu Thr Asn Glu Val Arg Ser Trp Leu Glu
            100                 105                 110

Gly Gln Glu Pro Arg His Leu Ala Glu Phe Leu Ile Gly Gly Val Ala
        115                 120                 125

Gly Gln Asp Leu Pro Glu Ser Glu Gly Ala Ser Val Val Lys Met Tyr
    130                 135                 140

Asn Asp Tyr Leu Gly His Ser Ser Phe Ile Leu Pro Pro Leu Pro Asn
145                 150                 155                 160

Thr Gln Phe Thr Arg Asp Thr Thr Cys Trp Ile Tyr Gly Gly Val Thr
                165                 170                 175

Leu Asn Pro Met Tyr Trp Pro Ala Arg Arg Gln Glu Thr Leu Leu Thr
            180                 185                 190

Thr Ala Ile Tyr Lys Phe His Pro Glu Phe Thr Lys Ala Asp Phe Gln
        195                 200                 205

Val Trp Tyr Gly Asp Pro Asp Gln Glu His Gly Gln Ala Thr Leu Glu
    210                 215                 220

Gly Gly Asp Val Met Pro Ile Gly Lys Gly Ile Val Leu Ile Gly Met
225                 230                 235                 240

Gly Glu Arg Thr Ser Arg Gln Ala Ile Gly Gln Leu Ala Gln Asn Leu
                245                 250                 255

Phe Ala Lys Gly Ala Val Glu Gln Val Ile Val Ala Gly Leu Pro Lys
            260                 265                 270

Ser Arg Ala Ala Met His Leu Asp Thr Val Phe Ser Phe Cys Asp Arg
        275                 280                 285

Asp Leu Val Thr Val Phe Pro Glu Val Val Arg Glu Ile Val Pro Phe
    290                 295                 300

Ile Ile Arg Pro Asp Glu Ser Lys Pro Tyr Gly Met Asp Val Arg Arg
305                 310                 315                 320

Glu Asn Lys Ser Phe Ile Glu Val Val Gly Glu Gln Leu Gly Val Lys

```
                    325                 330                 335
Leu Arg Val Val Glu Thr Gly Gly Asn Ser Phe Ala Ala Glu Arg Glu
                340                 345                 350

Gln Trp Asp Asp Gly Asn Asn Val Val Ala Leu Glu Pro Gly Val Val
                355                 360                 365

Ile Gly Tyr Asp Arg Asn Thr Tyr Thr Asn Thr Leu Leu Arg Lys Ala
                370                 375                 380

Gly Ile Glu Val Ile Thr Ile Ser Ala Gly Glu Leu Gly Arg Gly Arg
385                 390                 395                 400

Gly Gly Gly His Cys Met Thr Cys Pro Ile Val Arg Asp Pro Ile Asn
                405                 410                 415

Tyr

<210> SEQ ID NO 24
<211> LENGTH: 417
<212> TYPE: PRT
<213> ORGANISM: Pseudomonas putida

<400> SEQUENCE: 24

Met Ser Ala Glu Lys Gln Lys Tyr Gly Val His Ser Glu Ala Gly Lys
1               5                   10                  15

Leu Arg Lys Val Met Val Cys Ala Pro Gly Leu Ala His Lys Arg Leu
                20                  25                  30

Thr Pro Ser Asn Cys Asp Glu Leu Leu Phe Asp Asp Val Ile Trp Val
                35                  40                  45

Asp Gln Ala Lys Arg Asp His Phe Asp Phe Val Thr Lys Met Arg Glu
                50                  55                  60

Arg Gly Val Asp Val Leu Glu Met His Asn Leu Leu Thr Asp Ile Val
65                  70                  75                  80

Gln Asn Lys Asp Ala Leu Lys Trp Ile Leu Asp Arg Lys Ile Thr Pro
                85                  90                  95

Asp Thr Val Gly Val Gly Leu Thr Asn Glu Val Arg Ser Trp Leu Glu
                100                 105                 110

Gly Leu Glu Pro Arg His Leu Ala Glu Phe Leu Ile Gly Gly Val Ala
                115                 120                 125

Gly Gln Asp Leu Pro Gln Ser Glu Gly Ala Asp Val Val Lys Met Tyr
                130                 135                 140

Asn Asp Tyr Leu Gly His Ser Ser Phe Ile Leu Pro Pro Leu Pro Asn
145                 150                 155                 160

Thr Gln Phe Thr Arg Asp Thr Thr Cys Trp Ile Tyr Gly Gly Val Thr
                165                 170                 175

Leu Asn Pro Met Tyr Trp Pro Ala Arg Arg Gln Glu Thr Leu Leu Thr
                180                 185                 190

Thr Ala Ile Tyr Lys Phe His Pro Gln Phe Thr Gly Ala Asp Phe Gln
                195                 200                 205

Val Trp Tyr Gly Asp Pro Asp Lys Asp His Gly Asn Ala Thr Leu Glu
                210                 215                 220

Gly Gly Asp Val Met Pro Ile Gly Lys Gly Ile Val Leu Ile Gly Met
225                 230                 235                 240

Gly Glu Arg Thr Ser Arg Gln Ala Ile Gly Gln Leu Ala Gln Asn Leu
                245                 250                 255

Phe Ala Lys Gly Ala Val Glu Lys Val Ile Val Ala Gly Leu Pro Lys
                260                 265                 270

Ser Arg Ala Ala Met His Leu Asp Thr Val Phe Ser Phe Cys Asp Arg
```

```
            275                 280                 285
Asp Leu Val Thr Ile Phe Pro Glu Val Val Lys Glu Ile Val Pro Phe
            290                 295                 300
Ile Ile Arg Pro Asp Glu Ser Lys Pro Tyr Gly Met Asp Val Arg Arg
305                 310                 315                 320
Glu Asn Lys Ser Phe Ile Glu Val Val Gly Glu Gln Leu Gly Val Lys
                325                 330                 335
Leu Arg Val Val Glu Thr Gly Gly Asn Ser Phe Ala Ala Glu Arg Glu
            340                 345                 350
Gln Trp Asp Asp Gly Asn Asn Val Val Ala Val Glu Pro Gly Val Val
        355                 360                 365
Ile Gly Tyr Asp Arg Asn Thr Tyr Thr Asn Thr Leu Leu Arg Lys Ala
        370                 375                 380
Gly Ile Glu Val Ile Thr Ile Ser Ala Gly Leu Gly Arg Gly Arg
385                 390                 395                 400
Gly Gly Gly His Cys Met Thr Cys Pro Ile Val Arg Asp Pro Ile Asp
                405                 410                 415
Tyr

<210> SEQ ID NO 25
<211> LENGTH: 418
<212> TYPE: PRT
<213> ORGANISM: Pseudomonas aeruginosa

<400> SEQUENCE: 25

Met Ser Thr Glu Lys Thr Lys Leu Gly Val His Ser Glu Ala Gly Lys
1               5                   10                  15
Leu Arg Lys Val Met Val Cys Ser Pro Gly Leu Ala His Gln Arg Leu
            20                  25                  30
Thr Pro Ser Asn Cys Asp Glu Leu Leu Phe Asp Val Ile Trp Val
        35                  40                  45
Asn Gln Ala Lys Arg Asp His Phe Asp Phe Val Thr Lys Met Arg Glu
    50                  55                  60
Arg Gly Ile Asp Val Leu Glu Met His Asn Leu Leu Thr Glu Thr Ile
65                  70                  75                  80
Gln Asn Pro Glu Ala Leu Lys Trp Ile Leu Asp Arg Lys Ile Thr Ala
                85                  90                  95
Asp Ser Val Gly Leu Gly Leu Thr Ser Glu Leu Arg Ser Trp Leu Glu
            100                 105                 110
Ser Leu Glu Pro Arg Lys Leu Ala Glu Tyr Leu Ile Gly Gly Val Ala
        115                 120                 125
Ala Asp Asp Leu Pro Ala Ser Glu Gly Ala Asn Ile Leu Lys Met Tyr
    130                 135                 140
Arg Glu Tyr Leu Gly His Ser Ser Phe Leu Leu Pro Pro Leu Pro Asn
145                 150                 155                 160
Thr Gln Phe Thr Arg Asp Thr Thr Cys Trp Ile Tyr Gly Gly Val Thr
                165                 170                 175
Leu Asn Pro Met Tyr Trp Pro Ala Arg Arg Gln Glu Thr Leu Leu Thr
            180                 185                 190
Thr Ala Ile Tyr Lys Phe His Pro Glu Phe Ala Asn Ala Glu Phe Glu
        195                 200                 205
Ile Trp Tyr Gly Asp Pro Asp Lys Asp His Gly Ser Ser Thr Leu Glu
    210                 215                 220
Gly Gly Asp Val Met Pro Ile Gly Asn Gly Val Val Leu Ile Gly Met
```

-continued

```
225                 230                 235                 240
Gly Glu Arg Ser Ser Arg Gln Ala Ile Gly Gln Val Ala Gln Ser Leu
                245                 250                 255

Phe Ala Lys Gly Ala Ala Glu Arg Val Ile Val Ala Gly Leu Pro Lys
                260                 265                 270

Ser Arg Ala Ala Met His Leu Asp Thr Val Phe Ser Phe Cys Asp Arg
                275                 280                 285

Asp Leu Val Thr Val Phe Pro Glu Val Val Lys Glu Ile Val Pro Phe
                290                 295                 300

Ser Leu Arg Pro Asp Ala Ser Ser Pro Tyr Gly Met Ser Ile Arg Arg
305                 310                 315                 320

Glu Glu Lys Thr Phe Leu Glu Val Val Ala Glu Ser Leu Gly Leu Lys
                325                 330                 335

Lys Leu Arg Val Val Glu Thr Gly Gly Asn Ser Phe Ala Ala Glu Arg
                340                 345                 350

Glu Gln Trp Asp Asp Gly Asn Asn Val Val Cys Leu Glu Pro Gly Val
                355                 360                 365

Val Val Gly Tyr Asp Arg Asn Thr Tyr Thr Asn Thr Leu Leu Arg Lys
                370                 375                 380

Ala Gly Val Glu Val Ile Thr Ile Ser Ala Ser Glu Leu Gly Arg Gly
385                 390                 395                 400

Arg Gly Gly Gly His Cys Met Thr Cys Pro Ile Ile Arg Asp Pro Ile
                405                 410                 415

Asp Tyr

<210> SEQ ID NO 26
<211> LENGTH: 402
<212> TYPE: PRT
<213> ORGANISM: Mycobacterium tuberculosis complex

<400> SEQUENCE: 26

Met Gly Val Glu Leu Gly Ser Asn Ser Glu Val Gly Ala Leu Arg Val
1               5                   10                  15

Val Ile Leu His Arg Pro Gly Ala Glu Leu Arg Arg Leu Thr Pro Arg
                20                  25                  30

Asn Thr Asp Gln Leu Leu Phe Asp Gly Leu Pro Trp Val Ser Arg Ala
                35                  40                  45

Gln Asp Glu His Asp Glu Phe Ala Glu Leu Leu Ala Ser Arg Gly Ala
                50                  55                  60

Glu Val Leu Leu Leu Ser Asp Leu Leu Thr Glu Ala Leu His His Ser
65                  70                  75                  80

Gly Ala Ala Arg Met Gln Gly Ile Ala Ala Val Asp Ala Pro Arg
                85                  90                  95

Leu Gly Leu Pro Leu Ala Gln Glu Leu Ser Ala Tyr Leu Arg Ser Leu
                100                 105                 110

Asp Pro Gly Arg Leu Ala His Val Leu Thr Ala Gly Met Thr Phe Asn
                115                 120                 125

Glu Leu Pro Ser Asp Thr Arg Thr Asp Val Ser Leu Val Leu Arg Met
                130                 135                 140

His His Gly Gly Asp Phe Val Ile Glu Pro Leu Pro Asn Leu Val Phe
145                 150                 155                 160

Thr Arg Asp Ser Ser Ile Trp Ile Gly Pro Arg Val Val Ile Pro Ser
                165                 170                 175

Leu Ala Leu Arg Ala Arg Val Arg Glu Ala Ser Leu Thr Asp Leu Ile
```

```
            180                 185                 190
Tyr Ala His His Pro Arg Phe Thr Gly Val Arg Arg Ala Tyr Glu Ser
            195                 200                 205
Arg Thr Ala Pro Val Glu Gly Gly Asp Val Leu Leu Leu Ala Pro Gly
        210                 215                 220
Val Val Ala Val Gly Val Gly Glu Arg Thr Thr Pro Ala Gly Ala Glu
225                 230                 235                 240
Ala Leu Ala Arg Ser Leu Phe Asp Asp Leu Ala His Thr Val Leu
                245                 250                 255
Ala Val Pro Ile Ala Gln Gln Arg Ala Gln Met His Leu Asp Thr Val
            260                 265                 270
Cys Thr Met Val Asp Thr Asp Thr Met Val Met Tyr Ala Asn Val Val
            275                 280                 285
Asp Thr Leu Glu Ala Phe Thr Ile Gln Arg Thr Pro Asp Gly Val Thr
            290                 295                 300
Ile Gly Asp Ala Ala Pro Phe Ala Glu Ala Ala Lys Ala Met Gly
305                 310                 315                 320
Ile Asp Lys Leu Arg Val Ile His Thr Gly Met Asp Pro Val Val Ala
                325                 330                 335
Glu Arg Glu Gln Trp Asp Asp Gly Asn Asn Thr Leu Ala Leu Ala Pro
            340                 345                 350
Gly Val Val Val Ala Tyr Glu Arg Asn Val Gln Thr Asn Ala Arg Leu
            355                 360                 365
Gln Asp Ala Gly Ile Glu Val Leu Thr Ile Ala Gly Ser Glu Leu Gly
            370                 375                 380
Thr Gly Arg Gly Gly Pro Arg Cys Met Ser Cys Pro Ala Ala Arg Asp
385                 390                 395                 400
Pro Leu

<210> SEQ ID NO 27
<211> LENGTH: 409
<212> TYPE: PRT
<213> ORGANISM: Mycoplasma arthritidis

<400> SEQUENCE: 27

Met Ser Val Phe Asp Ser Lys Phe Lys Gly Ile His Val Tyr Ser Glu
1               5                   10                  15
Ile Gly Glu Leu Glu Thr Val Leu Val His Glu Pro Gly Lys Glu Ile
                20                  25                  30
Asp Tyr Ile Thr Pro Ala Arg Leu Asp Glu Leu Leu Phe Ser Ala Ile
            35                  40                  45
Leu Glu Ser His Asp Ala Arg Lys Glu His Lys Glu Phe Val Ala Glu
        50                  55                  60
Leu Lys Lys Arg Gly Ile Asn Val Val Glu Leu Val Asp Leu Ile Val
65                  70                  75                  80
Glu Thr Tyr Asp Leu Ala Ser Lys Glu Ala Lys Glu Lys Leu Leu Glu
                85                  90                  95
Glu Phe Leu Asp Asp Ser Val Pro Val Leu Ser Asp Glu His Arg Ala
            100                 105                 110
Ala Val Lys Lys Phe Leu Gln Ser Gln Lys Ser Thr Arg Ser Leu Val
        115                 120                 125
Glu Tyr Met Ile Ala Gly Ile Thr Lys His Asp Leu Lys Ile Glu Ser
    130                 135                 140
Asp Leu Glu Leu Ile Val Asp Pro Met Pro Asn Leu Tyr Phe Thr Arg
```

```
            145                 150                 155                 160
    Asp Pro Phe Ala Ser Val Gly Asn Gly Val Thr Ile His Tyr Met Arg
                    165                 170                 175

Tyr Lys Val Arg Gln Arg Glu Thr Leu Phe Ser Arg Phe Val Phe Ser
                    180                 185                 190

Asn His Pro Lys Leu Val Asn Thr Pro Trp Tyr Tyr Asp Pro Ala Glu
                    195                 200                 205

Gly Leu Ser Ile Glu Gly Gly Asp Val Phe Ile Tyr Asn Asn Asp Thr
                    210                 215                 220

Leu Val Gly Val Ser Glu Arg Thr Asp Leu Gln Thr Ile Thr Leu
    225                 230                 235                 240

Leu Ala Lys Asn Ile Lys Ala Asn Lys Glu Cys Glu Phe Lys Arg Ile
                    245                 250                 255

Val Ala Ile Asn Val Pro Lys Trp Thr Asn Leu Met His Leu Asp Thr
                    260                 265                 270

Trp Leu Thr Met Leu Asp Lys Asp Lys Phe Leu Tyr Ser Pro Ile Ala
                    275                 280                 285

Asn Asp Val Phe Lys Phe Trp Asp Tyr Asp Leu Val Asn Gly Gly Asp
                    290                 295                 300

Ala Pro Gln Pro Val Asp Asn Gly Leu Pro Leu Glu Asp Leu Leu Lys
    305                 310                 315                 320

Ser Ile Ile Gly Lys Lys Pro Thr Leu Ile Pro Ile Ala Gly Ala Gly
                    325                 330                 335

Ala Ser Gln Ile Asp Ile Glu Arg Glu Thr His Phe Asp Gly Thr Asn
                    340                 345                 350

Tyr Leu Ala Val Ala Pro Gly Ile Val Ile Gly Tyr Ala Arg Asn Glu
                    355                 360                 365

Lys Thr Asn Ala Ala Leu Glu Ala Ala Gly Ile Thr Val Leu Pro Phe
                    370                 375                 380

Arg Gly Asn Gln Leu Ser Leu Gly Met Gly Asn Ala Arg Cys Met Ser
    385                 390                 395                 400

Met Pro Leu Ser Arg Lys Asp Val Lys
                    405

<210> SEQ ID NO 28
<211> LENGTH: 410
<212> TYPE: PRT
<213> ORGANISM: Artificial Sequence
<220> FEATURE:
<223> OTHER INFORMATION: Artificial full length of Mycoplasma
      phocicerebrale

<400> SEQUENCE: 28

Met Ser Val Phe Asp Ser Lys Phe Asn Gly Ile His Val Tyr Ser Glu
    1               5                   10                  15

Ile Gly Glu Leu Glu Thr Val Leu Val

```
Glu Phe Leu Glu Asp Ser Glu Pro Val Leu Ser Glu Ala His Lys Thr
                100                 105                 110

Ala Val Arg Lys Phe Leu Thr Ser Arg Lys Ser Thr Arg Glu Met Val
            115                 120                 125

Glu Phe Met Met Ala Gly Ile Thr Lys Tyr Asp Leu Gly Ile Glu Ala
        130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Lys Thr Pro Trp Tyr Tyr Asp Pro Ala Met
        195                 200                 205

Lys Met Ser Ile Glu Gly Gly Asp Val Phe Ile Tyr Asn Asn Asp Thr
210                 215                 220

Leu Val Val Gly Val Ser Glu Arg Thr Asp Leu Glu Thr Ile Thr Leu
225                 230                 235                 240

Leu Ala Lys Asn Ile Lys Ala Asn Lys Glu Val Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Ala
290                 295                 300

Glu Pro Gln Pro Lys Glu Asn Gly Leu Pro Leu Glu Gly Leu Leu Gln
305                 310                 315                 320

Ser Ile Ile Asn Lys Lys Pro Val Leu Ile Pro Ile Ala Gly Asn Asn
                325                 330                 335

Ala Ser His Ile Asp Ile Glu Arg Glu Thr His Phe Asp Gly Thr Asn
            340                 345                 350

Tyr Leu Ala Ile Lys Pro Gly Val Val Ile Gly Tyr Ala Arg Asn Glu
        355                 360                 365

Lys Thr Asn Ala Ala Leu Ala Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 29
<211> LENGTH: 410
<212> TYPE: PRT
<213> ORGANISM: Artificial Sequence
<220> FEATURE:
<223> OTHER INFORMATION: Artificial full length of Mycoplasma gateae

<400> SEQUENCE: 29

Met Ser Val Phe Asp Ser Lys Phe As

Leu Glu Ser His Asp Ala Arg Lys Glu His Lys Leu Phe Val Ser Glu
 50                  55                  60

Leu Lys Ala Asn Asp Ile Asn Val Val Glu Leu Thr Asp Leu Val Thr
 65                  70                  75                  80

Glu Thr Tyr Asp Leu Ala Ser Gln Glu Ala Lys Asp Asn Leu Ile Glu
                 85                  90                  95

Glu Phe Leu Glu Asp Ser Pro Val Leu Thr Glu Glu Leu Lys Ser
            100                 105                 110

Val Val Arg Thr Tyr Leu Lys Ser Ile Lys Ser Thr Arg Glu Leu Ile
            115                 120                 125

Gln Met Met Met Ala Gly Ile Thr Lys Tyr Asp Leu Gly Ile Glu Ala
130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ser Leu
            195                 200                 205

Lys Leu Ser Ile Glu Gly Gly Asp Val Phe Ile Tyr Asn Asn Asn Thr
210                 215                 220

Leu Val Val Gly Val Ser Glu Arg Thr Asp Leu Glu Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Glu
290                 295                 300

Glu Pro Gln Pro Val Glu Asn Gly Leu Pro Leu Glu Gly Leu Leu Glu
305                 310                 315                 320

Ser Ile Ile Asn Lys Lys Pro Ile Leu Ile Pro Ile Ala Gly Glu Gly
                325                 330                 335

Ala Ser Gln Ile Asp Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 30
<211> LENGTH: 410
<212> TYPE: PRT
<213> ORGANISM: Artificial Sequence
<220> FEATURE:
<223> OTHER INFORMATION: Artificial full length of Mycoplasma phocidae

<400> SEQUENCE: 30

```
Met Ser Val Phe Asp Ser Lys Phe Asn Gly Ile His Val Tyr Ser Glu
1               5                   10                  15

Ile Gly Glu Leu Gln Thr Val Leu Val His Glu Pro Gly Arg Glu Ile
            20                  25                  30

Glu Tyr Ile Thr Pro Ala Arg Leu Asp Glu Leu Leu Phe Ser Ala Ile
            35                  40                  45

Leu Glu Ser His Asp Ala Arg Lys Glu His Gln Glu Phe Val Ala Glu
        50                  55                  60

Leu Lys Lys Asn Asn Ile Asn Val Val Glu Leu Thr Asp Leu Val Ser
65                  70                  75                  80

Glu Thr Tyr Asp Met Val Ser Lys Glu Lys Gln Glu Lys Leu Ile Glu
                85                  90                  95

Glu Phe Leu Glu Asp Ser Glu Pro Val Leu Ser Glu Glu His Lys Gly
            100                 105                 110

Leu Val Arg Lys Phe Leu Lys Ser Leu Lys Ser Ser Lys Glu Leu Ile
            115                 120                 125

Gln Tyr Met Met Ala Gly Ile Thr Lys His Asp Leu Asn Ile Glu Ala
        130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Ala
            180                 185                 190

Asn His Pro Lys Leu Met Asn Thr Pro Leu Tyr Tyr Asn Pro Asp Met
        195                 200                 205

Lys Leu Ser Ile Glu Gly Gly Asp Val Phe Val Tyr Asn Asn Glu Thr
        210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Arg Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Val Phe Lys Phe Trp Asp Tyr Asp Leu Val Asn Gly Gly Asp
        290                 295                 300

Glu Pro Gln Pro Lys Val Asn Gly Leu Pro Leu Glu Lys Leu Leu Glu
305                 310                 315                 320

Ser Ile Ile Asn Lys Lys Pro Ile Leu Ile Pro Ile Ala Gly Thr Ser
                325                 330                 335

Ala Ser Asn Ile Asp Val Glu Arg Glu Thr His Phe Asp Gly Thr Asn
            340                 345                 350

Tyr Leu Ala Ile Ala Pro Gly Val Val Ile Gly Tyr Ser Arg Asn Val
        355                 360                 365

Lys Thr Asn Glu Ala Leu Glu Ala Ala Gly Ile Lys Val Leu Pro Phe
        370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410
```

```
<210> SEQ ID NO 31
<211> LENGTH: 410
<212> TYPE: PRT
<213> ORGANISM: Mycoplasma salivarium

<400> SEQUENCE: 31
```

| | | | | | | | | | | | | | | |
|---|---|---|---|---|---|---|---|---|---|---|---|---|---|---|
| Met | Ser | Val | Phe | Ser | Ser | Lys | Phe | Asn | Gly | Ile | His | Val | Tyr | Ser | Glu |
| 1 | | | | 5 | | | | | 10 | | | | | 15 | |

Ile Gly Glu Leu Glu Thr Val Leu Val His Glu Pro Gly Lys Glu Ile
           20                  25                  30

Asp Tyr Ile Thr Pro Ser Arg Leu Asp Glu Leu Leu Phe Ser Ala Ile
            35                  40                  45

Leu Glu Ser His Asp Ala Arg Lys Glu His Gln Glu Phe Val Ala Thr
 50                  55                  60

Leu Lys Lys Glu Lys Ile Asn Val Val Glu Leu Thr Asp Leu Val Thr
65                  70                  75                  80

Glu Thr Tyr Asp Leu Val Asp Gln Lys Thr Lys Asp Lys Leu Ile Asp
                85                  90                  95

Glu Phe Leu Glu Asp Ser Glu Pro Val Leu Thr Ala Glu Leu Lys Ala
            100                 105                 110

Thr Val Lys Lys Phe Leu Lys Ser Phe Lys Glu Thr Arg Lys Leu Ile
            115                 120                 125

Glu Val Met Met Ala Gly Ile Thr Lys Tyr Asp Leu Gly Ile Lys Ala
            130                 135                 140

Asp Arg Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Asn
            180                 185                 190

Asn His Pro Lys Leu Val Lys Thr Pro Trp Tyr Tyr Asp Pro Ala Met
            195                 200                 205

Lys Met Ser Ile Glu Gly Gly Asp Val Phe Ile Tyr Asn Asn Asp Thr
210                 215                 220

Leu Val Val Gly Val Ser Glu Arg Thr Asp Leu Asp Thr Ile Thr Leu
225                 230                 235                 240

Leu Ala Lys Asn Ile Lys Ala Asn Lys Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asp Lys Phe Leu Tyr Ser Pro Ile Ala
            275                 280                 285

Asn Asp Ile Phe Lys Phe Trp Asp Tyr Asp Leu Val Asn Gly Gly Ala
            290                 295                 300

Asn Pro Gln Pro Lys Asp Asn Gly Leu Pro Leu Asp Lys Leu Leu Lys
305                 310                 315                 320

Ser Ile Ile Gly Lys Glu Pro Val Leu Ile Pro Ile Ala Gly His His
                325                 330                 335

Ala Thr Glu Ile Glu Val Ala Arg Glu Thr His Phe Asp Gly Thr Asn
            340                 345                 350

Tyr Leu Ala Ile Arg Pro Gly Val Val Ile Gly Tyr Ala Arg Asn Glu
            355                 360                 365

Lys Thr Asn Glu Ala Leu Lys Asp Ala Gly Ile Thr Val Leu Pro Phe
370                 375                 380

```
Lys Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 32
<211> LENGTH: 411
<212> TYPE: PRT
<213> ORGANISM: Mycoplasma spumans

<400> SEQUENCE: 32

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gly Phe Val Ala Glu
        50                  55                  60

Leu Lys Lys Gln Asn Val Asn Val Ile Glu Leu Thr Asp Leu Val Ala
65                  70                  75                  80

Glu Thr Tyr Glu Leu Ala Ser Lys Glu Ala Gln Ala Lys Leu Ile Glu
                85                  90                  95

Asp Phe Ile Glu Asp Ser Glu Pro Val Leu Asn Ala Glu Glu Ala Gln
            100                 105                 110

Ala Val Arg Lys Phe Leu Ser Glu Arg Lys Ser Thr Arg Glu Met Val
        115                 120                 125

Glu Tyr Met Met Ser Gly Leu Thr Lys Tyr Glu Leu Gly Leu Glu Ser
130                 135                 140

Ala Asp Arg Glu Leu Ile Val Asp Pro Met Pro Asn Leu Tyr Phe Thr
145                 150                 155                 160

Arg Asp Pro Phe Ala Ser Val Gly Asn Gly Val Thr Ile His Tyr Met
                165                 170                 175

Lys Tyr Lys Val Arg Gln Arg Glu Thr Leu Phe Ala Lys Phe Val Phe
            180                 185                 190

Ser Asn His Pro Lys Leu Val Asn Thr Pro Arg Tyr Tyr Asp Pro Ser
        195                 200                 205

Met Lys Leu Pro Ile Glu Gly Gly Asp Val Phe Ile Tyr Asn Asn Glu
210                 215                 220

Thr Leu Val Val Gly Cys Ser Glu Arg Thr Glu Leu Glu Thr Ile Thr
225                 230                 235                 240

Leu Leu Ala Lys Asn Ile Lys Ala Asn Lys Glu Val Glu Phe Lys Arg
                245                 250                 255

Ile Val Ala Ile Asn Val Pro Lys Trp Thr Asn Leu Met His Leu Asp
            260                 265                 270

Thr Trp Leu Thr Met Leu Asp Lys Asp Lys Phe Leu Tyr Ser Pro Ile
        275                 280                 285

Ala Asn Asp Val Phe Lys Phe Trp Asp Tyr Asp Leu Val Asn Gly Gly
        290                 295                 300

Glu Glu Pro Gln Pro Val Glu Asn Gly Leu Pro Leu Glu Glu Leu Leu
305                 310                 315                 320

Ala Ser Ile Ile Asn Lys Lys Pro Thr Leu Ile Pro Ile Ala Gly Glu
                325                 330                 335

Gly Ala Thr His Ile Asp Val Glu Arg Glu Thr His Phe Asp Gly Thr
            340                 345                 350
```

-continued

Asn Tyr Leu Ala Ile Ala Pro Ala Leu Ile Ile Gly Tyr Ser Arg Asn
            355                 360                 365

Glu Lys Thr Asn Ala Ala Leu Glu Lys Ala Gly Ile Thr Val Leu Pro
    370                 375                 380

Phe His Gly Asn Gln Leu Ser Leu Gly Met Gly Asn Ala Arg Cys Met
385                 390                 395                 400

Ser Met Pro Leu Ser Arg Lys Asp Val Lys Trp
                405                 410

<210> SEQ ID NO 33
<211> LENGTH: 410
<212> TYPE: PRT
<213> ORGANISM: Mycoplasma auris

<400> SEQUENCE: 33

Met Ser Val Phe Asp Ser Lys Phe Lys Gly Ile His Val Tyr Ser Glu
1               5                   10                  15

Ile Gly Glu Leu Glu Thr Val Leu Val His Glu Pro Gly Arg Glu Ile
            20                  25                  30

Asp Tyr Ile Thr Pro Lys Arg Leu Asp Glu Leu Leu Phe Ser Ala Ile
        35                  40                  45

Leu Glu Ser His Glu Ala Arg Lys Glu His Lys Gln Phe Val Ala Glu
    50                  55                  60

Leu Lys Ala Asn Asp Ile Asn Val Val Glu Leu Thr Asp Leu Val Ala
65                  70                  75                  80

Glu Thr Tyr Asp Leu Val Ser Gln Glu Leu Lys Asp Lys Leu Ile Glu
                85                  90                  95

Glu Phe Leu Asp Asp Ser Tyr Pro Val Leu Thr Glu Glu His Lys Lys
            100                 105                 110

Ala Val Arg Ser Phe Leu Lys Ser Arg Ser Thr Arg Glu Leu Ile
        115                 120                 125

Glu Tyr Met Met Ala Gly Ile Thr Lys Tyr Asp Leu Gly Ile Glu Ala
    130                 135                 140

Glu Gly Asp Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Asp
            180                 185                 190

Asn His Pro Lys Leu Val Asn Thr Pro Arg Tyr Tyr Asp Pro Ser Leu
        195                 200                 205

Lys Leu Ser Ile Glu Gly Gly Asp Val Phe Ile Tyr Asn Asn Asp Thr
    210                 215                 220

Leu Val Met Gly Val Ser Glu Arg Thr Asp Leu Glu Thr Val Thr Leu
225                 230                 235                 240

Leu Ala Lys Asn Ile Val Ala Asn Lys Glu Cys Glu Phe Lys Arg Ile
                245                 250                 255

Val Ala Ile Asn Val Pro His Trp Thr Asn Leu Met His Leu Asp Thr
            260                 265                 270

Trp Leu Thr Met Leu Asp Lys Asp Lys Phe Leu Tyr Ser Pro Ile Ala
        275                 280                 285

Asn Asp Tyr Phe Lys Phe Trp Asp Tyr Asp Leu Val Asn Gly Gly Ala
    290                 295                 300

Glu Pro Gln Pro Val Val Asn Glu Leu Pro Leu Asp Lys Leu Leu Glu

```
                305                 310                 315                 320
        Ser Ile Ile His Lys Lys Pro Ile Leu Ile Pro Ile Ala Gly Glu Gly
                        325                 330                 335

Ala Ser Gln Ile Asp Leu Glu Arg Glu Thr His Phe Asp Gly Thr Asn
                        340                 345                 350

Tyr Leu Val Leu Arg Pro Gly Val Val Gly Tyr Ala Arg Asn Glu
                        355                 360                 365

Lys Thr Asn Ala Ala Leu Glu Ala Val Gly Ile Lys Val Leu Pro Phe
                370                 375                 380

Tyr Gly Asn Gln Leu Ser Leu Gly Met Gly Asn Ser Arg Cys Met Ser
        385                 390                 395                 400

Met Pro Leu Ser Arg Lys Asp Val Lys Trp
                        405                 410

<210> SEQ ID NO 34
<211> LENGTH: 410
<212> TYPE: PRT
<213> ORGANISM: Mycoplasma hyosynoviae

<400> SEQUENCE: 34

Met Ser Val Phe Asn Ser Lys Phe Lys Gly Ile His Val Tyr Ser Glu
        1               5                   10                  15

Ile Gly Asp Leu Glu Ser Val Leu Val His Glu Pro Gly Lys Glu Ile
                        20                  25                  30

Asp Tyr Ile Thr Pro Ser Arg Leu Asp Glu Leu Leu Phe Ser Ala Ile
                        35                  40                  45

Leu Glu Ser Asn Asp Ala Arg Lys Glu His Lys Glu Phe Val Glu Ile
                50                  55                  60

Leu Lys Lys Glu Gly Val Asn Val Val Glu Leu Val Asp Leu Ile Ala
        65                  70                  75                  80

Glu Thr Ile Asp Leu Val Asp Ala Lys Lys Glu Ala Leu Ile Asp
                        85                  90                  95

Glu Tyr Ile Glu Asp Ser Glu Pro Val Val Asp Ala Lys Val Lys Pro
                        100                 105                 110

Leu Val Lys Lys Leu Leu Leu Gly Ile Lys Asp Thr Lys Glu Leu Val
                        115                 120                 125

Lys Leu Met Met Ala Gly Ile Thr Lys Tyr Asp Leu Glu Ile Glu Ser
                130                 135                 140

Glu Lys Glu Leu Ile Ile Asp Pro Met Pro Asn Leu Tyr Phe Thr Arg
        145                 150                 155                 160

Asp Pro Phe Ala Ser Val Gly Asn Gly Val Thr Ile His Tyr Met Arg
                        165                 170                 175

Tyr Lys Val Arg Gln Arg Glu Thr Leu Phe Ser Arg Phe Val Phe Arg
                        180                 185                 190

Asn His Pro Lys Leu Thr Ser Thr Pro Trp Tyr Tyr Asp Pro Ala Met
                        195                 200                 205

Lys Leu Ser Ile Glu Gly Gly Asp Val Phe Ile Tyr Asn Asn Asp Thr
                210                 215                 220

Leu Val Val Gly Val Ser Glu Arg Thr Asp Leu Asp Thr Ile Thr Leu
        225                 230                 235                 240

Leu Ala Lys Asn Ile Lys Ala Asn Lys Glu Cys Glu Phe Lys Arg Ile
                        245                 250                 255

Val Ala Ile Asn Val Pro Lys Trp Thr Asn Leu Met His Leu Asp Thr
                        260                 265                 270
```

```
Trp Leu Thr Met Leu Asp Lys Asp Lys Phe Leu Tyr Ser Pro Ile Ala
            275                 280                 285

Asn Asp Ile Phe Lys Phe Trp Asp Tyr Asp Leu Val Asn Gly Gly Ser
            290                 295                 300

Glu Pro Gln Pro Lys Asp Asn Gly Leu Pro Leu Glu Lys Leu Leu Glu
305                 310                 315                 320

Ser Ile Ile Gly Lys Lys Pro Val Leu Ile Pro Ile Ala Gly Cys Cys
            325                 330                 335

Ala Ser Asp Ile Glu Ile Ala Arg Glu Thr His Phe Asp Gly Thr Asn
            340                 345                 350

Tyr Leu Ala Ile Lys Pro Gly Val Val Ile Gly Tyr Ala Arg Asn Glu
            355                 360                 365

Lys Thr Asn Lys Ala Leu Glu Lys Ala Gly Ile Lys Val Leu Pro Phe
            370                 375                 380

Lys Gly Asn Gln Leu Ser Leu Gly Met Gly Asn Ala Arg Cys Met Ser
385                 390                 395                 400

Met Pro Leu Ser Arg Lys Asp Val Lys Trp
            405                 410

<210> SEQ ID NO 35
<211> LENGTH: 409
<212> TYPE: PRT
<213> ORGANISM: Mycoplasma cloacale

<400> SEQUENCE: 35

Met Ser Val Phe Asp Lys Arg Phe Lys Gly Ile His Val Tyr Ser Glu
1               5                   10                  15

Ile Gly Glu Leu Gln Thr Val Leu Val His Glu Pro Gly Arg Glu Ile
            20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Glu Phe Val Lys Ile
        50                  55                  60

Leu Glu Ser Gln Gly Ile Asn Val Val Glu Leu Thr Asp Leu Ile Ala
65                  70                  75                  80

Glu Thr Tyr Glu Leu Ala Ser Glu Glu Ala Lys Asp Asn Leu Ile Glu
                85                  90                  95

Glu Phe Leu Asp Glu Ser Glu Pro Val Leu Ser Glu Glu His Arg Ile
            100                 105                 110

Leu Val Arg Asn Phe Leu Lys Gly Ile Thr Lys Thr Lys Glu Leu Val
            115                 120                 125

Lys Met Met Met Ala Gly Ile Thr Lys Tyr Asp Leu Gly Ile Glu Ala
130                 135                 140

Asp Arg Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
            165                 170                 175

Tyr Lys Val Arg Gln Arg Glu Thr Leu Phe Ser Arg Phe Ile Phe Glu
            180                 185                 190

Asn His Pro Lys Leu Val Ser Thr Pro Ile Tyr Tyr His Pro Ser Gln
            195                 200                 205

Gly Leu Ser Ile Glu Gly Gly Asp Val Phe Ile Tyr Asn Asn Asp Thr
            210                 215                 220

Leu Val Val Gly Val Ser Glu Arg Thr Asp Leu Gln Thr Ile Thr Leu
225                 230                 235                 240
```

-continued

```
Leu Ala Lys Asn Ile Lys Ala Asn Glu Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Lys Asn Lys Phe Leu Tyr Ser Pro Ile Ala
        275                 280                 285

Asn Asp Val Phe Lys Phe Trp Asp Tyr Asp Leu Val Asn Gly Gly Asp
    290                 295                 300

Glu Pro Gln Pro Val Asp Asn Gly Leu Pro Leu Asn Glu Leu Leu Ala
305                 310                 315                 320

Ser Ile Ile Gly Glu Glu Pro Val Leu Val Pro Ile Ala Gly Glu Gly
                325                 330                 335

Ala Ser Lys Met Asp Ile Glu Arg Glu Thr His Phe Asp Gly Thr Asn
            340                 345                 350

Tyr Leu Ala Ile Ala Pro Gly Val Val Gly Tyr Ser Arg Asn Glu
        355                 360                 365

Lys Thr Asn Ala Ala Leu Glu Lys Ala Gly Ile Lys Val Leu Pro Phe
    370                 375                 380

Lys Gly His Gln Leu Ser Leu Gly Met Gly Asn Ala Arg Cys Met Ser
385                 390                 395                 400

Met Pro Leu Tyr Arg Lys Asp Val Lys
                405

<210> SEQ ID NO 36
<211> LENGTH: 412
<212> TYPE: PRT
<213> ORGANISM: Mycoplasma alkalescens

<400> SEQUENCE: 36

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly His Glu Ile
                20                  25                  30

Asp Tyr Ile Thr Pro Ser Arg Leu Asp Glu Leu Leu Phe Ser Ala Met
            35                  40                  45

Leu Glu Ser His Asp Ala Arg Lys Glu His Lys Gln Phe Val Ala Glu
        50                  55                  60

Leu Lys Ala Asn Asn Val Asn Val Ile Glu Leu Thr Asp Leu Val Ala
65                  70                  75                  80

Glu Thr Tyr Asp Leu Ala Ser Gln Glu Ala Lys Asp Lys Leu Ile Glu
                85                  90                  95

Glu Phe Leu Glu Asp Ser Glu Pro Val Leu Ser Glu Glu Asn Lys Ile
            100                 105                 110

Ala Val Arg Asp Phe Leu Lys Ser Arg Lys Thr Thr Arg Glu Leu Ile
        115                 120                 125

Glu Val Met Met Ala Gly Ile Thr Lys Tyr Asp Leu Gly Ile Lys Asn
    130                 135                 140

Cys Lys Cys Gln Asp Leu Val Val Asp Pro Met Pro Asn Leu Tyr Phe
145                 150                 155                 160

Thr Arg Asp Pro Phe Ala Ser Val Gly Asn Gly Ile Thr Ile His Tyr
                165                 170                 175

Met Arg Tyr Lys Val Arg Gln Arg Glu Thr Leu Phe Ser Arg Phe Ile
            180                 185                 190

Phe Ala Asn His Pro Lys Leu Val Asn Thr Pro Ile Tyr Tyr His Pro
```

```
                195                 200                 205
Ser Leu Lys Leu Ser Ile Glu Gly Gly Asp Val Phe Ile Tyr Asn Asn
210                 215                 220

Asp Thr Leu Val Val Gly Val Ser Glu Arg Thr Asp Leu Glu Thr Ile
225                 230                 235                 240

Thr Leu Leu Ala Lys Asn Ile Val Ala Asn Lys Glu Cys Glu Phe Lys
                245                 250                 255

Arg Ile Val Ala Ile Asn Val Pro Lys Trp Thr Asn Leu Met His Leu
                260                 265                 270

Asp Thr Trp Leu Thr Met Leu Asp Lys Asp Lys Phe Leu Tyr Ser Pro
                275                 280                 285

Ile Ala Asn Asp Val Phe Lys Phe Trp Asp Tyr Asp Leu Val Asn Gly
290                 295                 300

Gly Ala Glu Pro Lys Pro Val Glu Asn Gly Ser Ser Leu Glu Ala Ile
305                 310                 315                 320

Leu Glu Ser Ile Ile His Lys Lys Pro Ile Leu Ile Pro Ile Gly Gly
                325                 330                 335

Asp Ser Ala Ser Gln Ile Glu Val Glu Arg Glu Thr His Phe Asp Gly
                340                 345                 350

Thr Asn Tyr Leu Ala Ile Arg Pro Gly Val Val Ile Gly Tyr Ser Arg
                355                 360                 365

Asn Val Lys Thr Asn Ala Ala Leu Glu Ala Ala Gly Ile Lys Val Ile
370                 375                 380

Pro Phe His Gly Asn Gln Leu Ser Leu Gly Met Gly Asn Ala Arg Cys
385                 390                 395                 400

Met Ser Met Pro Leu Ser Arg Lys Asp Val Lys Trp
                405                 410

<210> SEQ ID NO 37
<211> LENGTH: 401
<212> TYPE: PRT
<213> ORGANISM: Mycoplasma iners

<400> SEQUENCE: 37

Met Ser Lys Ile Asn Val Tyr Ser Glu Ile Gly Val Leu Lys Glu Val
1               5                   10                  15

Leu Val His Thr Pro Gly Asp Glu Ile Arg Arg Ile Ala Pro Ser Arg
                20                  25                  30

Leu Asp Glu Leu Leu Phe Ser Ala Ile Leu Glu Pro Ser Ala Ala Ile
                35                  40                  45

Gln Glu His Lys Ser Phe Leu Lys Ile Leu Gln Asp Arg Gly Ile Lys
                50                  55                  60

Thr Ile Gln Leu Ser Asp Leu Val Ala Glu Thr Tyr Lys His Tyr Ala
65                  70                  75                  80

Ser Glu Ala Glu Lys Glu Ala Phe Ile Glu Lys Tyr Leu Asp Glu Ala
                85                  90                  95

Thr Pro Val Leu Ser Lys Asp Met Arg Ala Lys Val Lys Asn Tyr Ile
                100                 105                 110

Leu Ser Met Gln Gly Glu Pro Val Lys Met Val Arg Thr Met Met Ala
                115                 120                 125

Gly Val Ser Lys Gln Glu Leu Asn Val Glu Ser Glu Val Glu Leu Ile
                130                 135                 140

Val Asp Pro Met Pro Asn Leu Tyr Phe Thr Arg Asp Pro Phe Ala Ser
145                 150                 155                 160
```

-continued

```
Ala Gly Asn Gly Ile Ser Leu Asn Asn Met Lys Tyr Val Val Arg Lys
                165                 170                 175

Arg Glu Thr Ile Phe Ala Glu Phe Ile Phe Ser Ile His Pro Glu Tyr
            180                 185                 190

Lys Lys Thr Pro His Trp Phe Asp Arg Leu Asp Asn Gly Ser Ile Glu
        195                 200                 205

Gly Gly Asp Val Phe Ile Tyr Asn Lys Asp Thr Leu Val Ile Gly Val
    210                 215                 220

Ser Glu Arg Thr Asn Lys Glu Ala Ile Ile Thr Ile Ala Lys His Ile
225                 230                 235                 240

Gln Asp Asn Lys Glu Ala Gln Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Leu Tyr Ser Pro Asn Met Leu Ser Val Leu Lys
        275                 280                 285

Val Trp Glu Ile Asp Leu Ser Lys Pro Ile Glu Met Val Glu Thr Asn
    290                 295                 300

Lys Pro Leu Ala Glu Val Leu Glu Ser Ile Ile Gly Glu Lys Pro Ile
305                 310                 315                 320

Leu Ile Pro Ile Ala Gly Lys Asp Ala Thr Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Val Lys Thr Glu Ala Ala Leu Arg Ala
        355                 360                 365

Ala Gly Val Thr Val Leu Ser Phe Glu Gly Asn Gln Leu Ser Leu Gly
    370                 375                 380

Met Gly Ser Ala Arg Cys Met Ser Met Pro Leu Val Arg Glu Asp Val
385                 390                 395                 400

Lys

<210> SEQ ID NO 38
<211> LENGTH: 401
<212> TYPE: PRT
<213> ORGANISM: Mycoplasma gallinarum

<400> SEQUENCE: 38

Met Ser Lys Ile Arg Val Tyr Ser Glu Ile Gly Asn Leu Lys Lys Val
1               5                   10                  15

Leu Val His Thr Pro Gly Asp Glu Ile Arg Arg Ile Ser Pro Ser Arg
            20                  25                  30

Leu Glu Glu Leu Leu Phe Ser Ala Val Leu Glu Pro Asn Ala Ala Ile
        35                  40                  45

Glu Glu His Lys Arg Phe Val Lys Leu Leu Glu Asp Arg Gly Ile Gln
    50                  55                  60

Ala Ile Gln Leu Ser Asp Leu Val Ala Glu Thr Tyr Val Lys Tyr Ala
65                  70                  75                  80

Thr Ala Glu Gln Lys Ala Ala Phe Ile Glu Lys Tyr Leu Asp Glu Ala
                85                  90                  95

Thr Pro Ala Leu Ser Ala Glu Asn Arg Glu Arg Ala Lys Lys Tyr Ile
            100                 105                 110

Leu Ser Leu Glu Met Gln Pro Val Lys Met Ile Arg Thr Met Met Ala
        115                 120                 125
```

```
Gly Leu Ser Lys Tyr Glu Leu Asn Val Glu Ser Asn Ile Glu Leu Ile
    130                 135                 140

Ile Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
                165                 170                 175

Arg Glu Thr Ile Phe Ala Glu Phe Ile Phe Ala Ile His Pro Glu Tyr
            180                 185                 190

Lys Glu Thr Pro His Trp Phe Asp Arg Leu Asp His Gly Ser Ile Glu
        195                 200                 205

Gly Gly Asp Val Phe Val Tyr Asn Lys Asp Thr Leu Val Ile Gly Val
    210                 215                 220

Ser Glu Arg Thr Asn Lys Glu Ala Ile Ile Thr Ile Ala Lys His Ile
225                 230                 235                 240

Gln Asp Asn Lys Glu Ala Glu Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Ile Tyr Ser Pro Asn Met Leu Ser Val Leu Lys
        275                 280                 285

Ile Trp Glu Ile Asp Leu Ala Lys Pro Ile Glu Met Val Glu Ser Asn
    290                 295                 300

Lys Ser Leu Thr Glu Val Leu Glu Ser Ile Ile Gly Glu Lys Pro Ile
305                 310                 315                 320

Leu Ile Pro Ile Ala Gly Glu Gly Ala Ser Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Glu Lys Thr Glu Lys Ala Leu Lys Ala
        355                 360                 365

Ala Gly Ile Thr Val Leu Ser Phe Glu Gly Asn Gln Leu Ser Leu Gly
    370                 375                 380

Met Gly Ser Ala Arg Cys Met Ser Met Pro Leu Val Arg Glu Asp Val
385                 390                 395                 400

Lys

<210> SEQ ID NO 39
<211> LENGTH: 405
<212> TYPE: PRT
<213> ORGANISM: Mycoplasma pirum

<400> SEQUENCE: 39

Met Asn Ser Asn Gln Lys Gly Ile His Val Tyr Ser Glu Ile Gly Lys
1               5                   10                  15

Leu Lys Glu Val Leu Val His Arg Pro Gly Arg Glu Leu Asp Phe Leu
            20                  25                  30

Asp Pro Thr Arg Leu Asp Glu Leu Leu Phe Ala Ala Thr Leu Glu Ala
        35                  40                  45

Glu Thr Ala Arg Leu Glu His Asp Asn Phe Thr Asn Ala Leu Lys Asn
    50                  55                  60

Gln Gly Val Thr Val Ile Glu Leu Ala Asp Leu Val Ala Gln Thr Tyr
65                  70                  75                  80

Ser Ser Ser Thr Pro Thr Ile Lys Ala Ala Phe Ile Asn Lys Tyr Leu
                85                  90                  95
```

```
Asp Glu Ala Thr Pro Ala Leu Thr Thr Lys Leu Arg Thr Leu Val Lys
            100                 105                 110

Asp Phe Leu Thr Lys Gln Lys Ser Val Arg Lys Met Val Asp Tyr Met
        115                 120                 125

Ile Gly Gly Ile Leu Ser Thr Asp Leu Asn Ile Lys Gly Lys Pro Glu
    130                 135                 140

Leu Ile Val Glu Pro Met Pro Asn Ala Tyr Phe Thr His Asp Pro Phe
145                 150                 155                 160

Ala Ser Val Gly Asn Gly Val Thr Leu His Tyr Met Lys His Asn Val
                165                 170                 175

Arg Arg Arg Glu Val Leu Phe Ser Glu Phe Ile Phe Asn Asn Asn Glu
            180                 185                 190

Arg Phe Gln Asn Thr Pro Arg Tyr Ile Val Pro Thr Lys Gly Leu Asp
        195                 200                 205

Ile Glu Gly Gly Asp Val Phe Val Tyr Asn Lys Asn Thr Leu Val Val
    210                 215                 220

Gly Val Ser Glu Arg Thr Lys Met Val Thr Ile Lys Glu Leu Ala Lys
225                 230                 235                 240

Asn Ile Leu Lys Asn Lys Glu Cys Leu Phe Lys Lys Ile Tyr Ala Ile
                245                 250                 255

Asn Val Pro Lys Met Pro Asn Leu Met His Leu Asp Thr Trp Leu Thr
            260                 265                 270

Met Leu Asp His Asn Lys Phe Leu Tyr Ser Pro Asn Met Leu Ser Val
        275                 280                 285

Leu Lys Ile Trp Glu Ile Asp Ile Ser Ser Gly Lys Ser Ile Ser Ser
    290                 295                 300

Pro Lys Glu Leu Asn Met Asp Leu Ser Lys Ala Leu Ser Ile Ile Ile
305                 310                 315                 320

Gly Lys Lys Pro Ile Leu Ile Pro Val Ala Gly Glu Asn Ala Ser Gln
                325                 330                 335

Ile Asp Ile Asn Ile Glu Thr Asn Phe Asp Ala Thr Asn Tyr Leu Val
            340                 345                 350

Thr Gln Pro Gly Val Val Val Gly Tyr Ser Arg Asn Lys Lys Thr Glu
        355                 360                 365

Ala Ala Leu Ile Lys Ala Gly Ile Glu Val Ile Pro Phe Gln Gly Asn
    370                 375                 380

Gln Leu Ser Leu Gly Met Gly Ser Ala Arg Cys Met Ser Met Pro Leu
385                 390                 395                 400

Ile Arg Glu Asp Val
                405
```

<210> SEQ ID NO 40
<211> LENGTH: 404
<212> TYPE: PRT
<213> ORGANISM: Mycoplasma primatum

<400> SEQUENCE: 40

```
Met Ser Lys Ser Lys Ile Asn Val Tyr Ser Glu Tyr Gly Asn Leu Lys
1               5                   10                  15

Glu Val Leu Val His Thr Pro Gly Asp Glu Ile Arg Arg Ile Thr Pro
            20                  25                  30

Ser Arg Leu Asp Glu Leu Leu Phe Ser Ala Ile Leu Glu Pro Lys Ser
        35                  40                  45

Ala Ile Ala Glu His Lys Ser Phe Cys Gln Ile Leu Lys Asp Asn Lys
    50                  55                  60
```

Val Lys Ala Ile Gln Leu Asp Glu Leu Val Ala Thr Tyr Lys Gly
65                  70                  75                  80

Val Ser Glu Ser Val Gln Asn Ser Phe Val Glu Arg Trp Leu Asp Glu
            85                  90                  95

Cys Glu Pro Lys Leu Glu Asn Asn Val Arg Pro Ile Val Lys Glu Tyr
                100                 105                 110

Leu Leu Lys Ala Ala Glu Gln Ser Val Lys Lys Met Ile Arg Ile Met
            115                 120                 125

Met Ala Gly Ile Asp Lys Arg Glu Ile Gly Val Glu Ser Glu Val Asp
        130                 135                 140

Phe Ile Val Asp Pro Met Pro Asn Leu Tyr Phe Thr Arg Asp Pro Phe
145                 150                 155                 160

Ala Ser Val Gly Asn Gly Ile Thr Leu His His Met Lys Tyr Val Val
                165                 170                 175

Arg Gln Arg Glu Thr Leu Phe Ser Glu Phe Ile Phe Asp Asn His Pro
            180                 185                 190

Asp Tyr Lys Phe Val Pro Arg Tyr Phe Asp Arg Asp Glu Gly Lys
        195                 200                 205

Ile Glu Gly Gly Asp Val Phe Ile Tyr Asn Ser Lys Thr Leu Val Val
210                 215                 220

Gly Ile Ser Glu Arg Thr Asn Lys Asp Ala Ile Arg Ile Val Ala Lys
225                 230                 235                 240

Lys Ile Gln Ala Asn Ala Asp Ala Lys Phe Glu Lys Ile Phe Ala Ile
                245                 250                 255

Asn Val Pro Pro Met Pro Asn Leu Met His Leu Asp Thr Trp Leu Thr
            260                 265                 270

Met Leu Asp Ser Asn Lys Phe Leu Tyr Ser Pro Asn Met Leu Ser Val
        275                 280                 285

Leu Lys Val Trp Glu Ile Asn Leu Asp Asp Pro Ala Leu Glu Trp Lys
290                 295                 300

Glu Ile Ser Gly Ser Leu Glu Glu Ile Leu Thr Tyr Ile Ile Gly Lys
305                 310                 315                 320

Lys Pro Ile Leu Ile Pro Ile Ala Gly Lys Gly Ala Ser Gln Phe Glu
                325                 330                 335

Ile Asp Ile Glu Thr His Phe Asp Gly Thr Asn Tyr Leu Ala Ile Ala
            340                 345                 350

Pro Ser Val Val Ile Gly Tyr Ser Arg Asn Glu Leu Thr Glu Lys Ala
        355                 360                 365

Leu Lys Lys Ala Gly Val Lys Val Leu Ser Leu Asp Gly Asn Gln Leu
370                 375                 380

Ser Leu Gly Met Gly Ser Ala Arg Cys Met Ser Met Pro Leu Ile Arg
385                 390                 395                 400

Glu Asp Val Lys

<210> SEQ ID NO 41
<211> LENGTH: 401
<212> TYPE: PRT
<213> ORGANISM: Mycoplasma lipofaciens

<400> SEQUENCE: 41

Met Ser Lys Ile Asn Val Tyr Ser Glu Val Gly Val Leu Lys Glu Val
1               5                   10                  15

Leu Val His Thr Pro Gly Asp Glu Ile Arg Arg Val Ala Pro Ser Arg
            20                  25                  30

Leu Asp Glu Leu Leu Phe Ser Ala Ile Leu Glu Pro Gln Asp Ala Ile
            35                  40                  45

Ala Glu His Lys Arg Phe Ile Lys Ile Leu Glu Asp Asn Asn Ile Lys
 50                  55                  60

Val Ile Gln Leu Asp Glu Leu Val Ser Glu Thr Trp Glu Lys Ala Thr
 65                  70                  75                  80

Ala Glu Gln Arg Asp Ala Phe Ile Glu Lys Trp Leu Asp Glu Ala Glu
                85                  90                  95

Pro Val Leu Asp Ala Lys Leu Arg Glu Thr Val Lys Lys Tyr Leu Leu
               100                 105                 110

Ser Leu Asn Pro Val Lys Lys Met Val Arg Thr Met Met Ala Gly Ile
           115                 120                 125

Asp Lys Lys Glu Leu Lys Ile Glu Leu Asp Arg Asp Leu Val Val Asp
130                 135                 140

Pro Met Pro Asn Leu Tyr Phe Thr Arg Asp Pro Phe Ala Ser Ala Gly
145                 150                 155                 160

Asn Gly Ile Ser Leu Asn Asn Met Lys Tyr Val Thr Arg Lys Arg Glu
                165                 170                 175

Thr Ile Phe Ala Glu Phe Ile Phe Asn Ile His Pro Tyr Lys Thr
                180                 185                 190

Thr Pro His Trp Phe Asp Arg Leu Asp Lys Gly Asn Ile Glu Gly Gly
            195                 200                 205

Asp Val Phe Ile Tyr Asn Lys Asp Thr Leu Val Leu Gly Val Ser Glu
210                 215                 220

Arg Thr Asn Lys Asp Ala Val Met Thr Ile Ala Lys His Ile Gln Ser
225                 230                 235                 240

Asn Glu Gln Ala Lys Phe Lys Lys Leu Val Ala Ile Asn Val Pro Pro
                245                 250                 255

Met Pro Asn Leu Met His Leu Asp Thr Trp Leu Thr Met Val Asp His
            260                 265                 270

Asp Lys Phe Leu Tyr Ser Pro Asn Met Leu Ser Val Leu Lys Ile Trp
            275                 280                 285

Glu Ile Asp Leu Thr Pro Gly Lys Glu Ile Glu Met Val Glu Ser Thr
290                 295                 300

Lys Ser Leu Ser Asp Met Leu Glu Ser Ile Ile Gly Lys Lys Pro Val
305                 310                 315                 320

Leu Ile Pro Ile Ala Gly Lys Asp Ala Ser Gln Leu Asp Ile Asp Ile
                325                 330                 335

Glu Thr His Phe Asp Gly Thr Asn Tyr Leu Thr Ile Arg Pro Gly Val
            340                 345                 350

Val Val Gly Tyr Ser Arg Asn Cys Leu Thr Glu Gln Ala Leu Lys Asp
            355                 360                 365

Ala Gly Val Thr Val Leu Ser Phe Asp Gly Asn Gln Leu Ser Leu Gly
370                 375                 380

Met Gly Ser Ala Arg Cys Met Ser Met Pro Leu Val Arg Glu Asp Ile
385                 390                 395                 400

Lys

<210> SEQ ID NO 42
<211> LENGTH: 405
<212> TYPE: PRT
<213> ORGANISM: Mycoplasma felifaucium

<400> SEQUENCE: 42

-continued

```
Met Asn Lys Ile Asn Val Tyr Ser Glu Ile Gly Lys Leu Lys Glu Val
1               5                   10                  15

Leu Val His Thr Pro Gly Asn Glu Ile Arg Arg Ile Ser Pro Ser Arg
                20                  25                  30

Leu Asp Glu Leu Leu Phe Ser Ala Leu Leu Glu Pro Asn Phe Ala Ala
            35                  40                  45

Lys Glu His Thr Ala Phe Cys Glu Ile Leu Lys Glu Asn Gly Ile Lys
        50                  55                  60

Ala Ile Gln Leu Val Asp Leu Val Ser Asp Thr Trp Arg Ile Ala Ser
65                  70                  75                  80

Glu Lys Ala Lys Thr Glu Phe Ile Glu Arg Trp Leu Asp Glu Cys Glu
                85                  90                  95

Pro Lys Leu Asp Ser Asn Leu Arg Glu Ile Val Arg Lys His Ile Tyr
                100                 105                 110

Ala Ile Glu Lys Arg Ser Val Lys Arg Met Val Lys Thr Met Met Ala
            115                 120                 125

Gly Ile Glu Arg Arg Glu Leu Pro Val Thr Ser Lys Glu Val Ala Arg
130                 135                 140

Glu Leu Val Val Asp Pro Met Pro Asn Leu Tyr Phe Thr Arg Asp Pro
145                 150                 155                 160

Phe Ala Ser Val Gly Asn Gly Ile Ser Leu His His Met Lys Tyr Val
                165                 170                 175

Thr Arg Gln Arg Glu Thr Ile Phe Ala Glu Phe Val Phe Gly Asn His
                180                 185                 190

Pro Asp Tyr Ile Asp Thr Pro Arg Trp Phe Asp Arg Ser Asp Asp Gly
            195                 200                 205

Arg Ile Glu Gly Gly Asp Val Phe Ile Tyr Gly Ser Lys Thr Leu Val
210                 215                 220

Ile Gly Val Ser Glu Arg Thr Asn Lys Glu Ala Ile Lys Val Met Ala
225                 230                 235                 240

Lys Lys Ile Gln Ala Asn Lys Glu Ala Thr Phe Glu Lys Ile Tyr Ala
                245                 250                 255

Ile Asn Val Pro Pro Met Pro Asn Leu Met His Leu Asp Thr Trp Leu
            260                 265                 270

Thr Met Leu Asp Lys Asn Lys Phe Leu Tyr Ser Pro Asn Met Leu Ala
        275                 280                 285

Val Leu Gln Val Trp Glu Ile Asp Leu Lys Asp Pro Glu Leu Thr Trp
    290                 295                 300

His Glu Leu Ser Gly Ser Leu Glu Ile Leu His Lys Ile Ile Gly
305                 310                 315                 320

Arg Lys Pro Ile Leu Ile Pro Ile Ala Gly His Gly Ala Gln Gln Ile
                325                 330                 335

Asp Ile Asp Ile Glu Thr His Phe Asp Gly Thr Asn Tyr Leu Ala Ile
            340                 345                 350

Ala Pro Gly Val Val Gly Tyr Asn Arg Asn Val Leu Thr Glu Arg
        355                 360                 365

Ala Leu Lys Lys Ala Gly Ile Lys Val Leu Ser Phe Glu Gly Asn Gln
    370                 375                 380

Leu Ser Leu Gly Met Gly Ser Ala Arg Cys Met Ser Met Pro Leu Ile
385                 390                 395                 400

Arg Glu Asn Leu Lys
            405
```

<210> SEQ ID NO 43
<211> LENGTH: 404
<212> TYPE: PRT
<213> ORGANISM: Mycoplasma imitans

<400> SEQUENCE: 43

```
Met Phe Asn Lys Ile Lys Val Tyr Ser Glu Ile Gly Arg Leu Arg Lys
1               5                   10                  15

Val Leu Val His Thr Pro Gly Lys Glu Leu Glu Tyr Val Thr Pro Gln
            20                  25                  30

Arg Leu Asp Glu Leu Leu Phe Ser Ser Leu Leu Asn Pro Val Lys Ala
        35                  40                  45

Arg Gln Glu His Glu Ala Phe Ile Lys Ile Leu Gln Asp Gln Gly Val
    50                  55                  60

Glu Cys Val Gln Leu Thr Thr Leu Thr Ala Gln Thr Phe Gln Ser Ala
65                  70                  75                  80

Thr Ser Glu Val Lys Glu Lys Phe Ile Asn Arg Trp Leu Asp Glu Cys
                85                  90                  95

Leu Pro Lys Leu Ser Asp Asp Asn Arg Ile Lys Val Tyr Ala Tyr Leu
            100                 105                 110

Lys Asp Leu Ser Ser Asp Pro Glu Val Met Ile Arg Lys Met Met Ser
        115                 120                 125

Gly Ile Leu Ala Lys Glu Val Asn Val Gln Ser Asp Val Glu Leu Ile
    130                 135                 140

Ala Asp Pro Met Pro Asn Leu Tyr Phe Thr Arg Asp Pro Phe Ala Ser
145                 150                 155                 160

Ile Gly Lys Gly Val Thr Leu His Ser Met Phe His Pro Thr Arg Lys
                165                 170                 175

Arg Glu Thr Ile Phe Ala Asp Phe Val Phe Ser His His Pro Glu Tyr
            180                 185                 190

Lys Gln Thr Pro Lys Tyr Tyr Ser Arg Leu Asn Glu Tyr Ser Ile Glu
        195                 200                 205

Gly Gly Asp Leu Phe Val Tyr Asp Asp Lys Thr Leu Val Ile Gly Val
    210                 215                 220

Ser Glu Arg Thr Glu Lys Lys Ala Ile Gln Phe Leu Ala Glu Lys Leu
225                 230                 235                 240

Arg Glu Asn Tyr Glu Thr Thr Phe Glu Lys Ile Tyr Ala Ile Asn Val
                245                 250                 255

Pro Lys Met Ser Asn Leu Met His Leu Asp Thr Trp Leu Thr Met Leu
            260                 265                 270

Asp Tyr Asp Lys Phe Leu Tyr Ser Pro Asn Met Met Gly Val Leu Lys
        275                 280                 285

Ile Trp Glu Ile Asp Leu Thr His Glu Gln Leu Ser Trp Arg Glu Leu
    290                 295                 300

Asn Glu Ser Leu Glu Glu Phe Leu Ser Met Val Ile Gly Lys Lys Ala
305                 310                 315                 320

Thr Thr Ile Pro Val Ala Gly Glu Asp Ser Thr Gln Ile Glu Ile Asp
                325                 330                 335

Val Glu Thr Asn Phe Asp Ala Thr Asn Phe Leu Val Ile Gln Pro Gly
            340                 345                 350

Val Val Val Gly Tyr Asp Arg Asn Tyr Lys Thr Asn Gln Ala Leu Val
        355                 360                 365

Asn Ala Gly Ile Lys Val Leu Ser Trp Asn Gly Asp Gln Leu Ser Leu
    370                 375                 380
```

```
Gly Met Gly Ser Ala Arg Cys Met Ser Met Pro Leu Tyr Arg Asp Pro
385                 390                 395                 400

Ile Lys Lys Gly
```

<210> SEQ ID NO 44
<211> LENGTH: 401
<212> TYPE: PRT
<213> ORGANISM: Mycoplasma opalescens

<400> SEQUENCE: 44

```
Met Ser Lys Ile Asn Val Tyr Ser Glu Ile Gly Thr Leu Lys Glu Val
1               5                   10                  15

Leu Val His Thr Pro Gly Asp Glu Ile Arg Arg Val Ala Pro Ala Arg
                20                  25                  30

Leu Asp Glu Leu Leu Phe Ser Ala Ile Leu Glu Pro Asn His Ala Ile
            35                  40                  45

Ala Glu His Lys Ala Phe Ile Lys Ile Leu Glu Asp Asn Gly Ile Lys
        50                  55                  60

Val Ile Gln Leu Asp Glu Leu Val Val Gln Thr Trp Asn Gln Val Asp
65                  70                  75                  80

Glu Ala Thr Arg Lys Ala Phe Val Thr Lys Trp Leu Asp Glu Cys Glu
                85                  90                  95

Pro Lys Leu Glu Ser Asn Val Arg Val Glu Val Glu Lys Tyr Ile Tyr
            100                 105                 110

Ser Leu Ala Lys Glu Pro Lys Lys Met Val Arg Thr Met Met Ala Gly
        115                 120                 125

Ile Ser Lys Glu Glu Leu Pro Leu Asn Val Asn Arg Pro Leu Val Val
130                 135                 140

Asp Pro Met Pro Asn Leu Tyr Phe Thr Arg Asp Pro Phe Ala Ser Val
145                 150                 155                 160

Gly Thr Gly Ile Ser Leu His His Met Lys Tyr Val Thr Arg Gln Arg
                165                 170                 175

Glu Thr Ile Phe Ala Gln Phe Val Phe Asp Asn His Lys Asp Tyr Asn
            180                 185                 190

Thr Val Pro Arg Trp Phe Asp Asn Lys Asp Gln Gly Arg Ile Glu Gly
        195                 200                 205

Gly Asp Val Phe Ile Tyr Asn Thr Lys Thr Leu Val Ile Gly Val Ser
210                 215                 220

Glu Arg Thr Asp Lys Asp Ala Ile Lys Ile Met Ala Lys Lys Ile Gln
225                 230                 235                 240

Ala Asp Lys Asn Cys Lys Phe Glu Lys Ile Phe Ala Ile Asn Val Pro
                245                 250                 255

Pro Met Pro Asn Leu Met His Leu Asp Thr Trp Leu Thr Met Val Asp
            260                 265                 270

Arg Asn Lys Phe Leu Tyr Ser Pro Asn Met Leu Ser Val Leu Lys Val
        275                 280                 285

Trp Glu Ile Asp Leu Lys Asp Ala Ser Leu Ala Trp Lys Glu Ile Glu
290                 295                 300

Gly Ser Leu Ser Gln Ile Leu Glu Lys Ile Gly Glu Lys Pro Ile
305                 310                 315                 320

Leu Ile Pro Ile Ala Gly Glu Asn Ala Ser Gln Leu Asp Ile Asp Ile
                325                 330                 335

Glu Thr His Phe Asp Gly Thr Asn Tyr Leu Thr Ile Ala Pro Gly Val
            340                 345                 350
```

```
Val Val Gly Tyr Ser Arg Asn Val Lys Thr Glu Gln Ala Leu Lys Ala
        355                 360                 365

Ala Gly Val Lys Val Leu Ser Phe Glu Gly Asn Gln Leu Ser Leu Gly
    370                 375                 380

Met Gly Ser Ala Arg Cys Met Ser Met Pro Leu Ile Arg Glu Asp Leu
385                 390                 395                 400

Lys

<210> SEQ ID NO 45
<211> LENGTH: 425
<212> TYPE: PRT
<213> ORGANISM: Mycoplasma moatsii

<400> SEQUENCE: 45

Met Lys Lys Asn Ala Ile Asn Val Tyr Ser Glu Ile Gly Lys Leu Lys
1               5                   10                  15

Lys Val Leu Val His Arg Pro Gly Asp Glu Leu Lys Tyr Val Thr Pro
            20                  25                  30

Gln Arg Met Asp Glu Leu Leu Met Ser Ala Ile Ile Glu Leu Glu Gln
        35                  40                  45

Ala Lys Glu Glu His Asp Ala Phe Thr Lys Ile Leu Arg Asp Asn Gly
    50                  55                  60

Val Glu Val Ile Glu Leu Ala Asp Leu Thr Ala Glu Met Tyr Asp Ser
65                  70                  75                  80

Leu Thr Pro Ser Glu Lys Asp Ala Phe Leu Asn Gln Trp Val Lys Glu
                85                  90                  95

Ala Ser Trp Gly Lys Lys Ser Ser Ile Asp Ala Leu Lys Ile Lys Lys
            100                 105                 110

Asn Leu Ser Lys Lys Val Phe Asp Tyr Val Lys Ser Ile Lys Pro Thr
        115                 120                 125

Arg Lys Met Ile Asp Lys Leu Met Ala Gly Val Leu Leu Ser Glu Ile
    130                 135                 140

Gly Glu Lys Ser Ile Ile Leu Asn Lys Asp Lys Lys Asn Glu Met Val
145                 150                 155                 160

Ile Asp Leu Val Val Asp Pro Met Pro Asn Leu Tyr Phe Thr Arg Asp
                165                 170                 175

Pro Phe Ala Ser Val Gly Asn Gly Ile Thr Leu His Asn Met Lys Tyr
            180                 185                 190

Pro Thr Arg Lys Arg Glu Thr Ile Phe Ala Gln Trp Ile Phe Asn Lys
        195                 200                 205

His Pro Glu Tyr Lys Asp Val Pro Gln Phe Ile Ser Lys Arg Asp Gly
    210                 215                 220

Lys Glu Thr Ile Glu Gly Gly Asp Val Phe Ile Tyr Thr Lys Asp Val
225                 230                 235                 240

Leu Ala Ile Gly Val Ser Glu Arg Thr Asn Met Glu Ala Ile Leu Arg
                245                 250                 255

Ile Ala Thr Asn Ile Lys Lys Asp Lys Asn Cys Glu Phe Lys Lys Ile
            260                 265                 270

Val Ala Ile Asn Val Pro Pro Met Gly Asn Leu Met His Leu Asp Thr
        275                 280                 285

Trp Leu Thr Met Leu Asp Lys Asp Leu Phe Leu Tyr Ser Gly Asn Ile
    290                 295                 300

Lys Ser Ala Leu Lys Val Trp Glu Ile Asp Leu Thr Lys Pro Ile Thr
305                 310                 315                 320
```

```
Pro Lys Ser Pro Lys Leu Ser Thr Ala Lys Leu Ala Asp Ile Leu Ala
            325                 330                 335

Lys Ile Val Gly Lys Lys Val Arg Met Ile Pro Ile Gly Gly Lys Asp
            340                 345                 350

Gly Asn Gln Met Asp Ile Asp Ile Glu Thr His Phe Asp Gly Thr Asn
            355                 360                 365

Tyr Leu Ala Ile Ala Pro Gly Val Val Gly Tyr His Arg Asn Arg
        370                 375                 380

Lys Thr Gln Lys Ala Leu Glu Glu Ala Gly Val Lys Val Leu Ala Phe
385                 390                 395                 400

Gln Gly Asn Gln Leu Ser Leu Gly Met Gly Ser Ala Arg Cys Met Ser
            405                 410                 415

Met Pro Leu Val Arg Glu Glu Val Lys
            420                 425

<210> SEQ ID NO 46
<211> LENGTH: 399
<212> TYPE: PRT
<213> ORGANISM: Mycoplasma elephantis

<400> SEQUENCE: 46

Met Ser Gln Ile Asn Val Phe Ser Glu Ile Gly Gln Leu Lys Glu Val
1               5                   10                  15

Leu Val His Thr Pro Gly Asp Glu Ile Arg Arg Ile Ser Pro Lys Arg
            20                  25                  30

Tyr Asn Glu Leu Leu Phe Ser Ala Ile Leu Glu Ala Asp Val Ala Ile
        35                  40                  45

Lys Glu His Lys Ser Phe Val Lys Ile Leu Glu Glu Asn Asn Val Lys
    50                  55                  60

Val Ile Gln Leu Lys Asp Ile Leu Leu Glu Thr Trp Asn Ile Cys Ser
65              70                  75                  80

Lys Glu Ala Lys Asn Ile Phe Ile Asn Lys Trp Ile Glu Glu Ala Gln
            85                  90                  95

Pro Val Ile His Ser Ser Leu Lys Glu Lys Ile Lys Leu Phe Leu
            100                 105                 110

Lys Ser Lys Thr Pro Leu Glu Ile Ile Asp Ile Met Met Lys Gly Ile
        115                 120                 125

Leu Lys Gln Glu Leu Gly Ile Glu Tyr Lys His Glu Leu Ile Ile Asp
    130                 135                 140

Pro Met Pro Asn Leu Tyr Phe Thr Arg Asp Pro Phe Thr Ser Met Gly
145                 150                 155                 160

Ser Gly Ile Thr Ile Asn Asn Met Lys Tyr Gln Thr Arg Lys Arg Glu
            165                 170                 175

Thr Ile Phe Ser Glu Phe Ile Phe Asn Asn His Pro Lys Tyr Lys Asn
        180                 185                 190

Thr Pro Arg Trp Phe Asp Arg Phe Asp Ser Gly Asn Ile Glu Gly Gly
    195                 200                 205

Asp Leu Phe Val Tyr Thr Lys Glu Thr Ile Val Val Gly Val Ser Glu
210                 215                 220

Arg Thr Lys Lys Lys Ala Ile Leu Lys Ile Ala Lys Asn Ile Gln Glu
225                 230                 235                 240

Asn Asn Asn Ser Phe Lys Lys Ile Val Ile Lys Val Pro Ile Met
            245                 250                 255

Gln Asn Leu Met His Leu Asp Thr Trp Ile Val Met Val Asp Phe Asp
```

```
            260                 265                 270
Lys Phe Ile Tyr Ser Pro Asn Val Thr Lys Ser Leu Lys Phe Trp Glu
            275                 280                 285
Ile Asp Leu Thr Lys Lys Pro Lys Phe Ile Gln Leu Lys Asn Glu Thr
            290                 295                 300
Leu Glu Asp Val Leu Tyr Arg Val Ile Gly Lys Lys Pro Ile Leu Ile
305                 310                 315                 320
Pro Val Ala Gly Glu Asn Ala Asn Gln Ile Asp Ile Asp Val Glu Thr
                    325                 330                 335
His Phe Asp Ala Thr Asn Tyr Leu Thr Ile Arg Pro Gly Val Val Val
            340                 345                 350
Gly Tyr Ser Arg Asn Lys Lys Thr Glu Glu Ala Leu Ile Asn Ala Gly
            355                 360                 365
Val Lys Val Tyr Ala Phe Glu Gly Asn Gln Leu Ser Leu Gly Met Gly
            370                 375                 380
Ser Ala Arg Cys Met Ser Met Pro Leu Ile Arg Glu Asp Ile Ile
385                 390                 395

<210> SEQ ID NO 47
<211> LENGTH: 399
<212> TYPE: PRT
<213> ORGANISM: Mycoplasma testudinis

<400> SEQUENCE: 47

Met Lys Asn Ile Asn Val Tyr Ser Glu Val Gly Lys Leu Lys Glu Val
1               5                   10                  15
Val Val His Thr Pro Gly Glu Glu Leu His Asn Val Ala Pro Ser Arg
                20                  25                  30
Leu Gln Glu Leu Leu Thr Ser Ala Val Leu Glu Pro Glu Val Ala Arg
            35                  40                  45
Lys Glu His Leu Lys Phe Ile Lys Ile Leu Asn Asp Tyr Gly Val Lys
        50                  55                  60
Val Ile Gln Ile Val Asp Leu Ile Thr Glu Thr Tyr Glu Ala Val Asp
65                  70                  75                  80
Ser Asn Lys Lys Glu Ala Phe Ile Asn Asn Trp Leu Asp Asn Ser Val
                85                  90                  95
Pro Lys Leu Thr Asp Lys Asn Arg Met Ile Leu Arg Asn Tyr Leu Thr
            100                 105                 110
Gln Phe Ser Thr Lys Ala Met Ile Arg Lys Met Ile Ser Gly Ile Arg
        115                 120                 125
Ala Lys Glu Leu Asn Leu Lys Thr Pro Ser Ala Leu Leu Val Asp Pro
130                 135                 140
Met Pro Asn Leu Cys Phe Ala Arg Asp Thr Phe Ala Cys Val Gly Ser
145                 150                 155                 160
Ala Ile Ser Leu Ser Thr Met Lys His Pro Thr Arg Arg Arg Glu Ala
                165                 170                 175
Leu Leu Thr Glu Phe Ile Phe Gln Asn His Pro Lys Tyr Lys Asp Val
            180                 185                 190
Ile Lys Tyr Phe Asp Ser Lys Asn Ser Lys Ala Thr Ile Glu Gly Gly
        195                 200                 205
Asp Ile Phe Val Tyr Asn Pro Lys Thr Leu Val Val Gly Asn Ser Glu
210                 215                 220
Arg Thr Asn Met Gln Ala Cys Leu Leu Leu Ala Lys Lys Ile Gln Ser
225                 230                 235                 240
```

-continued

Asn Pro Asn Asn Lys Phe Glu Lys Ile Val Ile Val Asn Val Pro Pro
                245                 250                 255

Leu Pro His Leu Met His Leu Asp Thr Trp Leu Thr Met Val Asp Tyr
            260                 265                 270

Asp Lys Phe Ile Tyr Ser Pro Asn Ile Leu His Thr Leu Lys Phe Trp
            275                 280                 285

Val Ile Asp Leu Lys Lys Arg Lys Leu Glu Ala Val Glu Lys His Asn
    290                 295                 300

Thr Leu Lys Ala Met Leu Arg Met Ile Ile Lys Glu Pro Ile Leu
305                 310                 315                 320

Ile Pro Val Gly Asp Val Gly Ala Asp Gln Leu Asp Ile Asp Leu Glu
                325                 330                 335

Thr His Phe Asp Ala Thr Asn Tyr Leu Ala Leu Ala Pro Gly Val Val
            340                 345                 350

Val Gly Tyr Asp Arg Asn Ile Lys Thr Gln Arg Ala Leu Glu Lys Ala
            355                 360                 365

Gly Val Lys Val Leu Ser Phe Ser Gly Asn Gln Leu Ser Leu Ala Met
    370                 375                 380

Gly Ser Ala Arg Cys Leu Ser Met Pro Leu Ile Arg Glu Glu Asn
385                 390                 395

<210> SEQ ID NO 48
<211> LENGTH: 410
<212> TYPE: PRT
<213> ORGANISM: Mycoplasma canadense

<400> SEQUENCE: 48

Met Ser Val Phe Asp Ser Lys Phe Lys Gly Ile His Val Tyr Ser Glu
1               5                   10                  15

Ile Gly Glu Leu Glu Ser Val Leu Val His Glu Pro Gly Arg Glu Ile
                20                  25                  30

Asp Tyr Ile Thr Pro Ala Arg Leu Asp Glu Leu Leu Phe Ser Ala Ile
            35                  40                  45

Leu Glu Ser His Asp Ala Arg Lys Glu His Lys Gln Phe Val Ser Glu
50                  55                  60

Leu Lys Ala Asn Asp Ile Asn Val Val Glu Leu Thr Asp Leu Val Ala
65                  70                  75                  80

Glu Thr Tyr Asp Leu Ala Ser Gln Glu Ala Lys Asp Lys Leu Ile Glu
            85                  90                  95

Glu Phe Leu Glu Asp Ser Glu Pro Val Leu Ser Glu Glu His Lys Ala
            100                 105                 110

Ile Val Arg Lys Tyr Leu Lys Gly Ile Gln Pro Thr Arg Lys Leu Ile
        115                 120                 125

Glu Met Met Met Ala Gly Ile Thr Lys Tyr Asp Leu Gly Ile Glu Ala
    130                 135                 140

Asp His Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
            165                 170                 175

Tyr Lys Val Arg Gln Arg Glu Thr Leu Phe Ser Arg Phe Val Phe Ser
            180                 185                 190

Asn His Pro Lys Leu Val Asn Thr Pro Trp Tyr Tyr Asp Pro Ser Leu
        195                 200                 205

Lys Leu Ser Ile Glu Gly Gly Asp Val Phe Val Tyr Asn Asn Asp Thr
    210                 215                 220

```
Leu Val Val Gly Val Ser Glu Arg Thr Asp Leu Gln Thr Val Thr Leu
225                 230                 235                 240

Leu Ala Lys Asn Ile Val Ala Asn Lys Glu Cys Glu Phe Lys Arg Ile
            245                 250                 255

Val Ala Ile Asn Val Pro Lys Trp Thr Asn Leu Met His Leu Asp Thr
                260                 265                 270

Trp Leu Thr Met Leu Asp Lys Asp Lys Phe Leu Tyr Ser Pro Ile Ala
            275                 280                 285

Asn Asp Val Phe Lys Phe Trp Asp Tyr Asp Leu Val Asn Gly Gly Ser
        290                 295                 300

Glu Pro Gln Pro Val Glu Asn Gly Leu Pro Leu Glu Gly Leu Leu Glu
305                 310                 315                 320

Ser Ile Ile Asn Lys Lys Pro Ile Leu Ile Pro Ile Ala Gly Glu Gly
                325                 330                 335

Ala Ser Gln Met Glu Ile Glu Arg Glu Thr His Phe Asp Gly Thr Asn
            340                 345                 350

Tyr Leu Ala Ile Arg Pro Gly Val Val Ile Gly Tyr Ser Arg Asn Glu
        355                 360                 365

Lys Thr Asn Ala Ala Leu Glu Ala Ala Gly Ile Lys Val Leu Pro Phe
370                 375                 380

His Gly Asn Gln Leu Ser Leu Gly Met Gly Asn Ala Arg Cys Met Ser
385                 390                 395                 400

Met Pro Leu Ser Arg Lys Asp Val Lys Trp
                405                 410

<210> SEQ ID NO 49
<211> LENGTH: 409
<212> TYPE: PRT
<213> ORGANISM: Mycoplasma anseris

<400> SEQUENCE: 49

Met Ser Val Phe Asp Lys Arg Phe Lys Gly Ile His Val Tyr Ser Glu
1               5                   10                  15

Ile Gly Glu Leu Gln Thr Val Leu Val His Glu Pro Gly Arg Glu Ile
            20                  25                  30

Asp Tyr Ile Thr Pro Ala Arg Leu Asp Glu Leu Leu Phe Ser Ala Ile
        35                  40                  45

Leu Glu Ser His Asp Ala Arg Ala Glu His Lys Lys Phe Val Ala Thr
    50                  55                  60

Leu Lys Glu Gln Gly Ile Asn Thr Val Glu Leu Thr Asp Leu Val Ala
65                  70                  75                  80

Glu Thr Tyr Asp Leu Ala Ser Gln Glu Ala Arg Asp Asn Leu Leu Glu
                85                  90                  95

Glu Phe Leu Asp Asp Ser Ala Pro Val Leu Ser Glu Glu His Lys Glu
            100                 105                 110

Ile Val Arg Thr Tyr Leu Lys Gly Ile Lys Gly Thr Arg Lys Leu Ile
        115                 120                 125

Glu Thr Met Met Ala Gly Ile Thr Lys Tyr Asp Leu Gly Ile Glu Ala
    130                 135                 140

Glu Gln Glu Leu Ile Val Asp Pro Met Pro Asn Leu Tyr Phe Thr Arg
145                 150                 155                 160

Asp Pro Phe Ala Ser Val Gly Asn Gly Val Thr Ile His Tyr Met Arg
                165                 170                 175

Tyr Lys Val Arg Gln Arg Glu Thr Leu Phe Ser Arg Phe Ile Phe Ser
```

```
                    180                 185                 190
Asn His Pro Gln Leu Val Asn Thr Pro Trp Tyr Tyr Asn Pro Ala Glu
            195                 200                 205

Gly Leu Ser Ile Glu Gly Gly Asp Val Phe Ile Tyr Asn Asn Asp Thr
    210                 215                 220

Leu Val Val Gly Val Ser Glu Arg Thr Asp Leu Gln Thr Ile Thr Leu
225                 230                 235                 240

Leu Ala Lys Asn Ile Lys Ala Asn Glu Glu Cys Glu Phe Lys Arg Ile
                245                 250                 255

Val Ala Ile Asn Val Pro Lys Trp Thr Asn Leu Met His Leu Asp Thr
            260                 265                 270

Trp Leu Thr Met Leu Asp Thr Asn Lys Phe Leu Tyr Ser Pro Ile Ala
            275                 280                 285

Asn Asp Val Phe Lys Phe Trp Asp Tyr Asp Leu Val Asn Gly Gly Asp
            290                 295                 300

Glu Pro Gln Pro Val Asp Asn Gly Leu Pro Leu Asn Glu Leu Leu Lys
305                 310                 315                 320

Ser Ile Ile Gly Glu Glu Pro Ile Leu Ile Pro Ile Ala Gly Asp Gly
                325                 330                 335

Ala Thr Gln Ile Glu Ile Glu Arg Glu Thr His Phe Asp Gly Thr Asn
            340                 345                 350

Tyr Leu Ala Ile Ala Pro Gly Val Val Ile Gly Tyr Ser Arg Asn Glu
            355                 360                 365

Lys Thr Asn Ala Ala Leu Glu Ala Ala Gly Ile Lys Val Leu Pro Phe
            370                 375                 380

Lys Gly His Gln Leu Ser Leu Gly Met Gly Asn Ala Arg Cys Met Ser
385                 390                 395                 400

Met Pro Leu Tyr Arg Lys Asp Val Lys
                405

<210> SEQ ID NO 50
<211> LENGTH: 401
<212> TYPE: PRT
<213> ORGANISM: Mycoplasma meleagridis

<400> SEQUENCE: 50

Met Ser Lys Ile Asn Val Tyr Ser Glu Ile Gly Val Leu Lys Glu Val
1               5                   10                  15

Leu Val His Thr Pro Gly Asp Glu Ile Arg Arg Ile Ser Pro Ser Arg
            20                  25                  30

Leu Asp Glu Leu Leu Phe Ser Ala Ile Leu Gln Pro Glu Gln Ala Ile
        35                  40                  45

Lys Glu His Gln Ser Phe Val Lys Ile Leu Gln Asp Arg Gly Ile Lys
    50                  55                  60

Val Ile Gln Leu Ser Asp Leu Val Ala Glu Thr Tyr Val Lys Tyr Ala
65                  70                  75                  80

Thr Ser Lys Glu Lys Glu Ser Phe Ile Glu Lys Trp Leu Asp Glu Ala
                85                  90                  95

Thr Pro Ala Leu Asn Ser Glu Asn Arg Ala Arg Val Lys Asn Tyr Ile
            100                 105                 110

Thr Ala Met Gln Gly Gln Pro Val Lys Met Val Arg Ala Met Met Ala
        115                 120                 125

Gly Val Ser Lys Gln Glu Leu Asn Ile Glu Ser Asp Val Glu Leu Ile
    130                 135                 140
```

Val Asp Pro Met Pro Asn Leu Tyr Phe Thr Arg Asp Pro Phe Ala Ser
145                 150                 155                 160

Ala Gly Asn Gly Ile Ser Leu Asn Asn Met Lys Tyr Val Val Arg Lys
            165                 170                 175

Arg Glu Thr Ile Phe Ala Glu Phe Ile Phe Ser Ile His Pro Glu Tyr
            180                 185                 190

Lys Gln Thr Pro His Trp Phe Asp Arg Leu Asp Lys Gly Asn Ile Glu
        195                 200                 205

Gly Gly Asp Val Phe Ile Tyr Asn Lys Asp Thr Leu Val Ile Gly Val
    210                 215                 220

Ser Glu Arg Thr Asn Lys Glu Ala Ile Leu Thr Ile Ala Glu His Ile
225                 230                 235                 240

Lys Asn Asn Lys Glu Ala Lys Phe Lys Lys Ile Val Ala Ile Asn Val
                245                 250                 255

Pro Pro Met Pro Asn Leu Met His Leu Asp Thr Trp Leu Thr Met Val
            260                 265                 270

Asp Lys Asn Lys Phe Leu Tyr Ser Pro Asn Met Leu Ser Val Leu Lys
        275                 280                 285

Ile Trp Glu Ile Asp Leu Ser Lys Glu Ile Lys Met Val Glu Thr Ser
    290                 295                 300

Lys Pro Leu Ala Asp Val Leu Glu Ser Ile Ile Gly Glu Lys Pro Ile
305                 310                 315                 320

Leu Ile Pro Ile Ala Gly Glu Asn Ala Ser Gln Leu Asp Ile Asp Ile
                325                 330                 335

Glu Thr His Phe Asp Gly Thr Asn Tyr Leu Thr Ile Ala Pro Gly Val
            340                 345                 350

Val Val Gly Tyr Ser Arg Asn Val Lys Thr Glu Ala Ala Leu Lys Ala
        355                 360                 365

Ala Gly Val Thr Val Tyr Ser Phe Asp Gly Asn Gln Leu Ser Leu Gly
    370                 375                 380

Met Gly Ser Gly Arg Cys Met Ser Met Pro Leu Val Arg Glu Asp Val
385                 390                 395                 400

Lys

<210> SEQ ID NO 51
<211> LENGTH: 404
<212> TYPE: PRT
<213> ORGANISM: Mycoplasma alvi

<400> SEQUENCE: 51

Met Ser Ile Lys Glu Asn Gly Ile His Val Tyr Ser Glu Ile Gly Lys
1               5                   10                  15

Leu Arg Asp Val Leu Val His Arg Pro Gly Arg Glu Leu Asn Phe Leu
            20                  25                  30

Asp Pro Ser Arg Leu Asp Glu Leu Leu Phe Ala Ala Thr Leu Glu Pro
        35                  40                  45

Glu Thr Ala Arg Leu Glu His Asp Asn Phe Thr Thr Val Leu Lys Asn
    50                  55                  60

Gln Gly Val Asn Val Ile Glu Leu Ala Asp Leu Val Ser Gln Thr Tyr
65                  70                  75                  80

Ser Lys Val Asp Ser Lys Val Lys Glu Phe Ile Asp Gln Tyr Leu
                85                  90                  95

Asn Glu Ala Thr Pro Lys Leu Ser Glu Leu Ser Lys Lys Val Tyr
            100                 105                 110

```
Asp Phe Leu Thr Lys Gln Lys Ser Asn Arg Glu Met Val Asp Phe Met
            115                 120                 125
Met Gly Gly Ile Leu Ser Ser Asp Leu Asn Ile Lys Gly Gln Pro Tyr
130                 135                 140
Leu Ile Val Glu Pro Met Pro Asn Leu Tyr Phe Thr Arg Asp Pro Phe
145                 150                 155                 160
Ala Ser Val Gly Asn Gly Ala Thr Ile His Trp Met Lys His Asn Val
                165                 170                 175
Arg Arg Arg Glu Val Leu Phe Ala Asn Phe Ile Phe Lys Tyr Asn Glu
            180                 185                 190
Arg Phe Gln Asn Thr Pro Lys Tyr Ile Thr Pro Thr Lys Gly Leu Asp
        195                 200                 205
Ile Glu Gly Gly Asp Val Phe Val Tyr Asn Lys Lys Thr Leu Val Val
210                 215                 220
Gly Val Ser Glu Arg Thr Lys Met Glu Thr Ile Lys Glu Leu Ala Lys
225                 230                 235                 240
Asn Ile Ser Lys Asn Lys Glu Cys Thr Phe Thr Lys Ile Tyr Ala Ile
                245                 250                 255
Asn Val Pro Lys Met Pro Asn Leu Met His Leu Asp Thr Trp Leu Thr
            260                 265                 270
Met Leu Asp Tyr Asn Lys Phe Leu Tyr Ser Pro Asn Met Leu Ser Val
        275                 280                 285
Leu Lys Val Trp Glu Ile Asn Ile Ser Asn Asn Lys Val Ser Ala Pro
290                 295                 300
Lys Glu Leu Asn Val Asn Leu Glu Lys Ala Leu Ser Met Ile Ile Gly
305                 310                 315                 320
Lys Lys Pro Ile Leu Ile Pro Val Ala Gly Ala Asn Ala Ser Gln Ile
                325                 330                 335
Asp Ile Asn Ile Glu Thr Asn Phe Asp Ala Thr Asn Tyr Leu Val Ile
            340                 345                 350
Glu Pro Gly Val Val Gly Tyr Ser Arg Asn Lys Lys Thr Glu Glu
        355                 360                 365
Ala Leu Val Lys Ala Gly Ile Lys Val Leu Pro Phe His Gly Asn Gln
370                 375                 380
Leu Ser Leu Gly Met Gly Ser Ala Arg Cys Met Ser Met Pro Leu Tyr
385                 390                 395                 400
Arg Glu Asp Val

<210> SEQ ID NO 52
<211> LENGTH: 410
<212> TYPE: PRT
<213> ORGANISM: Mycoplasma penetrans

<400> SEQUENCE: 52

Met Ser Ser Ile Asp Lys Asn Ser Leu Gly Asn Gly Ile Asn Val Tyr
1               5                   10                  15
Ser Glu Ile Gly Glu Leu Lys Glu Val Leu His Thr Pro Gly Asp
            20                  25                  30
Glu Ile Arg Tyr Thr Ala Pro Ser Arg Leu Glu Glu Leu Leu Phe Ser
        35                  40                  45
Ala Val Leu Lys Ala Asp Thr Ala Ile Glu Glu His Lys Gly Phe Val
50                  55                  60
Lys Ile Leu Gln Asn Asn Gly Ile Lys Val Ile Gln Leu Cys Asp Leu
65                  70                  75                  80
```

Val Ala Glu Thr Tyr Glu Leu Cys Ser Lys Glu Val Arg Asn Ser Phe
            85                  90                  95

Ile Glu Gln Tyr Leu Asp Glu Ala Leu Pro Val Leu Lys Lys Glu Ile
            100                 105                 110

Arg Pro Val Val Lys Asp Tyr Leu Leu Ser Phe Pro Thr Val Gln Met
            115                 120                 125

Val Arg Lys Met Met Ser Gly Ile Leu Ala Asn Glu Leu Asn Ile Lys
            130                 135                 140

Gln Asp Asn Pro Leu Ile Ile Asp Gly Met Pro Asn Leu Tyr Phe Thr
145                 150                 155                 160

Arg Asp Pro Phe Ala Ser Met Gly Asn Gly Val Ser Ile Asn Cys Met
            165                 170                 175

Lys Tyr Pro Thr Arg Lys Arg Glu Val Ile Phe Ser Arg Phe Val Phe
            180                 185                 190

Thr Asn Asn Pro Lys Tyr Lys Asn Thr Pro Arg Tyr Phe Asp Ile Val
            195                 200                 205

Gly Asn Asn Gly Thr Ile Glu Gly Gly Asp Ile Phe Ile Tyr Asn Ser
            210                 215                 220

Lys Thr Leu Val Ile Gly Asn Ser Glu Arg Thr Asn Phe Ala Ala Ile
225                 230                 235                 240

Glu Ser Val Ala Lys Asn Ile Gln Ala Asn Lys Asp Cys Thr Phe Glu
            245                 250                 255

Arg Ile Val Val Ile Asn Val Pro Pro Met Pro Asn Leu Met His Leu
            260                 265                 270

Asp Thr Trp Leu Thr Met Leu Asp Tyr Asp Lys Phe Leu Tyr Ser Pro
            275                 280                 285

Asn Met Met Asn Val Leu Lys Ile Trp Glu Ile Asp Leu Asn Val Lys
            290                 295                 300

Pro Val Lys Phe Val Glu Lys Lys Gly Thr Leu Glu Glu Val Leu Tyr
305                 310                 315                 320

Ser Ile Ile Asp Lys Lys Pro Ile Leu Ile Pro Ile Ala Gly Lys Gly
            325                 330                 335

Ala Asn Gln Leu Asp Ile Asp Ile Glu Thr His Phe Asp Gly Thr Asn
            340                 345                 350

Tyr Leu Thr Ile Ala Pro Gly Val Val Gly Tyr Glu Arg Asn Glu
            355                 360                 365

Lys Thr Gln Lys Ala Leu Val Glu Ala Gly Ile Lys Val Leu Ser Phe
            370                 375                 380

Asn Gly Ser Gln Leu Ser Leu Gly Met Gly Ser Ala Arg Cys Met Ser
385                 390                 395                 400

Met Pro Leu Ile Arg Glu Asn Leu Lys Lys
            405                 410

<210> SEQ ID NO 53
<211> LENGTH: 404
<212> TYPE: PRT
<213> ORGANISM: Mycoplasma fermentans

<400> SEQUENCE: 53

Met Lys Lys Ile Asn Val Tyr Ser Glu Tyr Gly Lys Leu Lys Glu Val
1               5                   10                  15

Leu Val His Thr Pro Gly Asp Glu Ile Arg Arg Ile Ala Pro Ser Arg
            20                  25                  30

Leu Asp Glu Leu Leu Phe Ser Ala Ile Leu Glu Pro Asp Ser Ala Ile
            35                  40                  45

```
Ala Glu His Lys Arg Phe Val Gln Leu Leu Lys Asp Asn Gly Ile Lys
         50                  55                  60

Val Ile Gln Leu Asp Glu Leu Phe Ala Lys Thr Phe Asp Leu Val Ser
 65                  70                  75                  80

Glu Ser Val Lys Gln Ser Phe Ile Glu Arg Trp Leu Asp Glu Cys Glu
                 85                  90                  95

Pro Lys Leu Asp Ala Thr Leu Arg Ala Lys Val Lys Glu Tyr Ile Leu
            100                 105                 110

Glu Leu Lys Ala Lys Ser Ser Lys Met Val Arg Val Met Met Ala
        115                 120                 125

Gly Ile Asp Lys Lys Glu Leu Gly Ile Glu Leu Asp Arg Asp Leu Val
        130                 135                 140

Val Asp Pro Met Pro Asn Leu Tyr Phe Thr Arg Asp Pro Phe Ala Ser
145                 150                 155                 160

Val Gly Asn Gly Ile Ser Leu His His Met Lys Tyr Val Thr Arg Gln
                165                 170                 175

Arg Glu Thr Ile Phe Ser Glu Phe Ile Phe Asp Asn Asn Leu Asp Tyr
            180                 185                 190

Asn Thr Val Pro Arg Trp Phe Asp Arg Lys Asp Glu Gly Arg Ile Glu
        195                 200                 205

Gly Gly Asp Val Phe Ile Tyr Ser Ala Asp Thr Leu Val Val Gly Val
210                 215                 220

Ser Glu Arg Thr Asn Lys Glu Ala Ile Asn Val Met Ala Arg Lys Ile
225                 230                 235                 240

Ala Ala Asp Lys Glu Val Lys Phe Lys Arg Ile Tyr Ala Ile Asn Val
                245                 250                 255

Pro Pro Met Pro Asn Leu Met His Leu Asp Thr Trp Leu Thr Met Leu
            260                 265                 270

Asp Lys Asn Lys Phe Leu Tyr Ser Pro Asn Met Leu Ser Val Leu Lys
        275                 280                 285

Val Trp Arg Ile Asp Leu Asn Asp Pro Asp Phe Val Trp His Glu Ile
290                 295                 300

Glu Gly Ser Leu Glu Glu Ile Leu Glu Gln Ile Ile Gly Met Lys Pro
305                 310                 315                 320

Ile Leu Ile Pro Ile Ala Gly Lys Gly Ala Ser Gln Leu Asp Ile Asp
                325                 330                 335

Ile Glu Thr His Phe Asp Gly Thr Asn Tyr Leu Thr Ile Ala Pro Ser
            340                 345                 350

Val Val Val Gly Tyr Ser Arg Asn Glu Lys Thr Glu Lys Ala Leu Lys
        355                 360                 365

Ala Ala Lys Val Lys Val Leu Ser Phe Glu Gly Asn Gln Leu Ser Leu
370                 375                 380

Gly Met Gly Ser Ala Arg Cys Met Ser Met Pro Leu Ile Arg Glu Asp
385                 390                 395                 400

Ile Lys Lys Lys

<210> SEQ ID NO 54
<211> LENGTH: 404
<212> TYPE: PRT
<213> ORGANISM: Mycoplasma pneumoniae

<400> SEQUENCE: 54

Met Lys Tyr Asn Ile Asn Val His Ser Glu Ile Gly Gln Leu Gln Thr
 1               5                  10                  15
```

Val Leu Val His Thr Pro Gly Asn Glu Ile Arg Arg Ile Ser Pro Arg
            20                  25                  30

Arg Leu Asp Asp Leu Leu Phe Ser Ala Val Ile Glu Pro Asp Thr Ala
        35                  40                  45

Ile Gln Glu His Gln Thr Phe Cys Gln Leu Leu Gln Glu Gln Asn Ile
 50                  55                  60

Glu Val Val Gln Leu Thr Asp Leu Thr Ala Thr Thr Phe Asp Lys Ala
 65                  70                  75                  80

Asn Ala Thr Ala Gln Asn Gln Phe Ile Glu Thr Trp Leu Asp Gln Ala
                85                  90                  95

Glu Pro Lys Leu Thr Pro Glu His Arg Lys Val Ala Lys Gln Tyr Leu
            100                 105                 110

Leu Glu Gln Lys Ala Lys Ser Thr Leu Ser Met Val Arg Ser Met Met
        115                 120                 125

Gly Gly Ile Asp Lys Arg Lys Val Ala Ala Asn Thr Ile Asn Gly
130                 135                 140

Asp Phe Leu Val Asp Pro Met Pro Asn Leu Tyr Phe Thr Arg Asp Pro
145                 150                 155                 160

Phe Ala Ser Ile Gly His Gly Ile Ser Ile Asn Arg Met Lys Tyr Leu
                165                 170                 175

Thr Arg Arg Arg Glu Thr Leu Phe Ala Ser Phe Ile Phe Ala Asn His
            180                 185                 190

Pro Ile Ile Ala Ala Arg Lys Phe Tyr Phe Lys Pro Ile Asp Met Gly
        195                 200                 205

Thr Ile Glu Gly Gly Asp Ile Phe Val Tyr Asp Gln Gln Thr Val Val
 210                 215                 220

Met Gly Leu Ser Glu Arg Thr Thr Glu Ala Ala Ile Asn Val Leu Ala
225                 230                 235                 240

Lys Lys Ile Gln Gln Asp Ser Ser Thr Ser Phe Lys Arg Ile Phe Val
                245                 250                 255

Ile Asn Val Pro Gln Leu Pro Asn Leu Met His Leu Asp Thr Trp Leu
            260                 265                 270

Thr Met Leu Asp Arg Asn Lys Phe Leu Tyr Ser Pro Asn Met Leu Ala
        275                 280                 285

Val Leu Lys Ala Trp Arg Ile Asp Phe Thr Asp Pro Ala Leu Lys Trp
 290                 295                 300

Asn Glu Ile Ala Gly Asp Leu Ser Thr Ile Leu His Thr Ile Gly
305                 310                 315                 320

Gln Lys Pro Met Leu Ile Pro Ile Ala Gly Ala Asp Ala Asn Gln Thr
                325                 330                 335

Glu Ile Asp Ile Glu Thr His Phe Asp Gly Thr Asn Tyr Leu Thr Ile
            340                 345                 350

Ala Pro Ser Val Val Gly Tyr Ala Arg Asn Lys Leu Thr His Gln
        355                 360                 365

Thr Leu Glu Ala Ala Gly Val Lys Val Ile Ala Phe Lys Gly Asn Gln
 370                 375                 380

Leu Ser Leu Gly Met Gly Ser Ala Arg Cys Met Ser Met Pro Leu Val
385                 390                 395                 400

Arg Lys Pro Leu

<210> SEQ ID NO 55
<211> LENGTH: 414
<212> TYPE: PRT

<213> ORGANISM: Mycoplasma sp. CAG:877

<400> SEQUENCE: 55

```
Met Glu Lys Ile His Val Thr Ser Glu Ile Gly Pro Leu Lys Lys Val
1               5                   10                  15

Leu Leu His Arg Pro Gly Asn Glu Leu Leu Asn Leu Thr Pro Asp Thr
            20                  25                  30

Leu Ser Arg Leu Leu Phe Asp Asp Ile Pro Tyr Leu Pro Asp Ala Ile
        35                  40                  45

Lys Glu His Asp Glu Phe Ala Asp Ala Leu Arg Ala Asn Gly Val Glu
    50                  55                  60

Val Val Tyr Leu Glu Asn Leu Met Ala Asp Val Leu Asp Leu Ser Asp
65                  70                  75                  80

Glu Ile Arg Asp Lys Phe Ile Lys Gln Phe Ile Tyr Glu Ala Gly Ile
                85                  90                  95

Arg Thr Pro Lys Tyr Lys Tyr Leu Val Phe Asp Tyr Leu Asp Gln Ile
            100                 105                 110

Thr Asn Ser Lys Lys Leu Val Leu Lys Thr Met Glu Gly Ile Gln Ile
        115                 120                 125

Ser Asp Ile Pro Arg Arg Lys Arg Glu Ile Glu Lys Ser Leu Val Asp
    130                 135                 140

Leu Ile Glu Thr Glu Asp Glu Phe Ile Ala Asp Pro Met Pro Asn Leu
145                 150                 155                 160

Tyr Phe Thr Arg Asp Pro Phe Ala Ser Val Gly Gly Ile Ser Leu
                165                 170                 175

Asn Lys Met Tyr Ser Val Thr Arg Asn Arg Glu Thr Ile Tyr Ala Glu
            180                 185                 190

Tyr Ile Phe Lys Tyr His Pro Asp Tyr Lys Asp Gln Ala Arg Leu Tyr
        195                 200                 205

Tyr Asp Arg Tyr Asn Pro Tyr His Ile Glu Gly Gly Asp Val Leu Asn
    210                 215                 220

Ile Asn Asp His Val Leu Ala Ile Gly Ile Ser Gln Arg Thr Thr Ala
225                 230                 235                 240

Glu Ala Ile Asp Gln Ile Ala Lys Asn Leu Phe Lys Asp Pro Glu Cys
                245                 250                 255

Lys Ile Asp Thr Ile Leu Ala Phe Asn Ile Pro Glu Ser Arg Ala Phe
            260                 265                 270

Met His Leu Asp Thr Val Phe Thr Gln Val Asp Tyr Asp Lys Phe Thr
        275                 280                 285

Tyr His Pro Gly Ile Met Gly Thr Leu Gln Val Phe Glu Ile Thr Glu
    290                 295                 300

Gly Asp Asp Pro Asn Ser Asp Glu Asp Leu Thr Val Thr Glu Ile Asn
305                 310                 315                 320

Ala Pro Leu Glu Glu Ile Leu Thr Lys Tyr Val Gly Arg Lys Val Thr
                325                 330                 335

Leu Ile Pro Cys Ala Gly Gly Asp Lys Val Ser Ala Glu Arg Glu Gln
            340                 345                 350

Trp Asn Asp Gly Ser Asn Thr Leu Cys Ile Ala Pro Gly Val Val Val
        355                 360                 365

Val Tyr Asp Arg Asn Asn Leu Thr Asn Ala Val Leu Arg Ser Tyr Gly
    370                 375                 380

Leu Lys Val Ile Glu Ile His Gly Ala Glu Leu Ser Arg Gly Arg Gly
385                 390                 395                 400
```

```
Gly Pro Arg Cys Met Ser Met Pro Leu Val Arg Glu Asp Ile
                405                 410

<210> SEQ ID NO 56
<211> LENGTH: 408
<212> TYPE: PRT
<213> ORGANISM: Mycoplasma sp. CAG:472

<400> SEQUENCE: 56

Met His Val Thr Ser Glu Ile Lys Lys Leu Lys Val Leu Val His
1               5                   10                  15

Arg Pro Gly Lys Glu Leu Leu Asn Leu Thr Pro Asp Thr Leu Gly Arg
                20                  25                  30

Leu Leu Phe Asp Asp Ile Pro Tyr Leu Lys Asp Ala Ile Leu Glu His
            35                  40                  45

Asp Glu Phe Cys Gln Ile Leu Arg Asp Asn Asp Val Glu Val Val Tyr
        50                  55                  60

Leu Glu Asp Leu Met Ala Glu Thr Leu Asp Glu Asn Pro Gln Val Lys
65                  70                  75                  80

Pro Ser Phe Ile Arg Gln Phe Ile Tyr Glu Ala Gly Val Arg Thr Pro
                85                  90                  95

Lys Tyr Lys Asp Leu Leu Phe Asp Tyr Leu Met Ser Tyr Thr Asn Asn
                100                 105                 110

Lys Glu Leu Val Leu Lys Thr Met Glu Gly Ile Lys Val Ser Glu Val
            115                 120                 125

His Arg Asn Lys Gln Asp Ser Glu Tyr Ser Leu Val Asp Gln Ile Ser
        130                 135                 140

Glu Glu Thr Lys Phe Leu Ala Glu Pro Met Pro Asn Leu Tyr Phe Thr
145                 150                 155                 160

Arg Asp Pro Phe Ala Ser Val Gly Asp Gly Ile Ile Leu Asn Lys Met
                165                 170                 175

His Ser Val Thr Arg Ser Arg Glu Thr Ile Tyr Ala Tyr Tyr Ile Phe
                180                 185                 190

Asn Tyr His Pro Asp Tyr Met Asp Lys Val Pro Lys Tyr Tyr Asp Arg
            195                 200                 205

Glu Asn Pro Phe Ser Ile Glu Gly Gly Asp Val Leu Asn Leu Asn Glu
        210                 215                 220

His Thr Leu Ala Ile Gly Ile Ser Gln Arg Thr Ser Ala Glu Ala Ile
225                 230                 235                 240

Asp Leu Val Ala Lys Asn Met Phe Asn Asp Glu Lys Cys Asn Ile Asp
                245                 250                 255

Thr Ile Leu Ala Phe Lys Ile Pro Glu Cys Arg Ala Phe Met His Leu
                260                 265                 270

Asp Thr Val Phe Thr Gln Ile Asp Ile Asp Lys Phe Thr Tyr His Pro
            275                 280                 285

Gly Ile Met Asp Thr Leu Glu Val Phe Glu Ile Thr Lys Asn Glu Asp
        290                 295                 300

Asp Leu Asp Glu Val Arg Val Ile Lys Lys Glu Gly Ser Leu Glu Asn
305                 310                 315                 320

Ile Leu Glu Glu Tyr Leu Gly Ile Asp Ile Thr Leu Ile Pro Cys Ala
                325                 330                 335

Gly Gly Asp Lys Ile Ala Ser Glu Arg Glu Gln Trp Asn Asp Gly Thr
                340                 345                 350

Asn Thr Leu Cys Ile Ala Pro Gly Val Val Val Tyr Asn Arg Asn
            355                 360                 365
```

```
Asn Ile Thr Asn Glu Val Leu Arg Glu Lys Gly Ile Lys Val Ile Glu
    370             375             380

Met Asn Ser Ala Glu Leu Ser Arg Gly Arg Gly Gly Pro Arg Cys Met
385             390             395             400

Ser Met Pro Leu Glu Arg Glu Asp
                405
```